US010221425B2

(12) United States Patent
Chu et al.

(10) Patent No.: US 10,221,425 B2
(45) Date of Patent: Mar. 5, 2019

(54) BG1 COMPOSITIONS AND METHODS TO INCREASE AGRONOMIC PERFORMANCE OF PLANTS

(71) Applicant: INSTITUTE OF GENETICS AND DEVELOPMENTAL BIOLOGY, CHINESE ACADEMY OF SCIENCES, Beijing (CN)

(72) Inventors: Chengcai Chu, Beijing (CN); Linchuan Liu, Beijing (CN); Hongning Tong, Beijing (CN); Bin Hu, Beijing (CN); Chengzhen Liang, Beijing (CN); Ronghui Che, Beijing (CN); Fan Xu, Beijing (CN)

(73) Assignee: INSTITUTE OF GENETICS AND DEVELOPMENTAL BIOLOGY, CHINESE ACADEMY OF SCIENCES, Beijing (CN)

( * ) Notice: Subject to any disclaimer, the term of this patent is extended or adjusted under 35 U.S.C. 154(b) by 289 days.

(21) Appl. No.: 14/910,437

(22) PCT Filed: Aug. 8, 2014

(86) PCT No.: PCT/CN2014/083982
§ 371 (c)(1),
(2) Date: Feb. 5, 2016

(87) PCT Pub. No.: WO2015/018359
PCT Pub. Date: Feb. 12, 2015

(65) Prior Publication Data
US 2016/0251673 A1 Sep. 1, 2016

(30) Foreign Application Priority Data
Aug. 8, 2013 (CN) .......................... 2013 1 0343713

(51) Int. Cl.
*C12N 15/82* (2006.01)
*C07K 14/415* (2006.01)
*C12Q 1/6895* (2018.01)

(52) U.S. Cl.
CPC ........ *C12N 15/8261* (2013.01); *C07K 14/415* (2013.01); *C12Q 1/6895* (2013.01); *C12Q 2600/13* (2013.01); *C12Q 2600/156* (2013.01); *Y02A 40/146* (2018.01)

(58) Field of Classification Search
None
See application file for complete search history.

(56) References Cited

U.S. PATENT DOCUMENTS

2006/0123505 A1* 6/2006 Kikuchi ............... C07K 14/415
800/278
2017/0037426 A1* 2/2017 Alexandrov ......... C07K 14/415

FOREIGN PATENT DOCUMENTS

CN 101161675 A 4/2008
CN 103408648 A 11/2013

OTHER PUBLICATIONS

Tanaka et al. (Genbank Sequence No. NP_001049135.1, Published Jun. 8, 2010).*
Smith et al. (Nature Biotechnology, 15:1222-1223, 1997).*
Bork et al. (TIG, 12:425-427, 1996).*
Doerks et al., (TIG, 14:248-250, 1998).*
Nishimura et al. (Plant Cell Physiol., 41 (5):583-590, 2000).*
Wells, Biochemistry 29:8509-8517, 1990, see pp. 8511-8512, tables 1-2.*
Ngo et al., (The Protein Folding Problem and Tertiary Structure Prediction, K. Merz., and S. Le Grand (eds.) pp. 492-495,1994).*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Yang et al. (PNAS, 98:11438-11443, 2001).*
Liu et al. (PNAS, 112:11102-11107; Published Sep. 1, 2015).*
International Search Report and Written Opinion for International Application No. PCT/CN2014/083982, dated Nov. 19, 2014.
Genbank accession NP001146458, 2015.
Genbank accession NP001049135, 2010.
Genbank accession DAA43664.1, 2012.
Qi, Peng, et al, "The novel quantitive trait locus GL3.1 controls rice grain size and yield by regulating Cyclin-T1;3" Cell Research, 2012, vol. 22:1666-1680.
Wang, Shaokui, et al, "Control of grain size, shape and quality of OsSPL16 in rice" Nature Genetics, 2012, vol. 44:8, 950-955.
Zhang, Xiaojun, et al, "Rare allele of OsPPKL1 associate with grain length causes extra-large grain and a significant yield increase in rice" PNA, 2012, vol. 109:52, 21534-21639.
Zuo, Jianru, et al, "Molecular Genetic Dissection of Quantitive Trait Loci Regulating Rice Grain Size" Annut. Rev. Genet., 2014, 48:99-118.

* cited by examiner

*Primary Examiner* — Vinod Kumar
(74) *Attorney, Agent, or Firm* — McNeill Baur PLLC

(57) ABSTRACT

Methods and compositions that affect yield and other agronomic characteristics in plants are disclosed. Methods of transgenic modulation and marker-assisted breeding methods improve grain size and grain yield in rice are also disclosed. Increased expression of BG1 results in increased grain size and yield.

9 Claims, 17 Drawing Sheets

Figure 1:
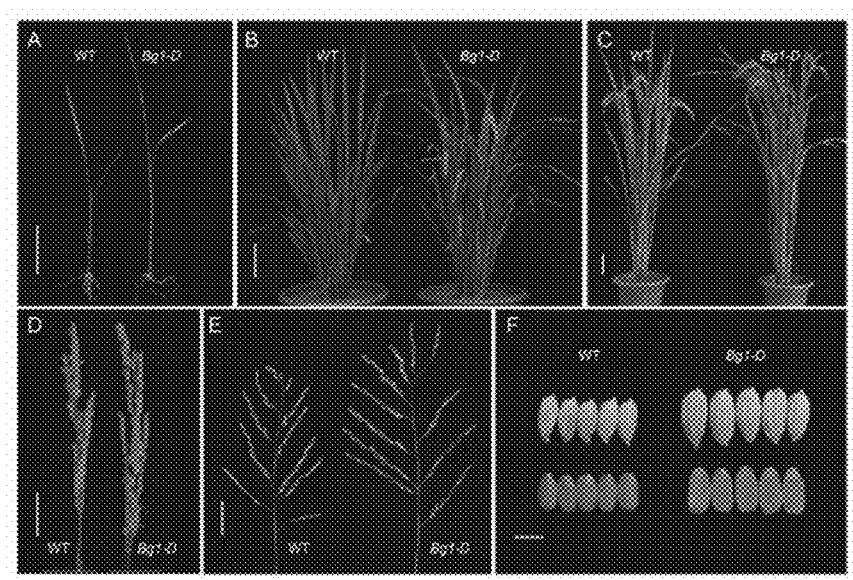

Specification includes a Sequence Listing.

BG1 COMPOSITIONS AND METHODS TO INCREASE AGRONOMIC PERFORMANCE OF PLANTS

CROSS REFERENCE

This utility application claims the benefit of priority of Chinese Application No. 201310343713.3, filed Aug. 8, 2013, which is incorporated herein by reference.

FIELD

The disclosure relates generally to the field of molecular biology.

BACKGROUND

The domestication of many plants has correlated with dramatic increases in yield. Most phenotypic variation occurring in natural populations is continuous and is effected by multiple gene influences. The identification of specific genes responsible for the dramatic differences in yield, in domesticated plants, has become an important focus of agricultural research.

Rice is a major dietary component for over half of the world's population. Simultaneous improvement of yield and end-use quality of rice remains a challenge. Grain size is a prime breeding target, as it affects both yield and quality. Genetic control of this trait has been extensively investigated over the last decade. However, many of the genetic determinants for grain size are currently explained only by quantitative trait loci (QTLs), without a detailed understanding of the nature of the encoded gene product. The present disclosure provides methods and compositions to improve grain size, shape and quality.

SUMMARY

The present disclosure provides polynucleotides, related polypeptides and all conservatively modified variants of a novel gene, OsBG1 that has been shown to affect grain yield and other agronomic parameters in rice. In an embodiment, BIG GRAIN1 (BG1) controls the elongation of both grains and internodes. In an embodiment, transgenic plants over-expressing BG1 had increased seed size and panicle length, whereas knockdown of BG1 by RNAi led to smaller seed size. BG1 can be induced by auxin and Bg1-D mutant showed increased sensibility to IAA and enhanced polar auxin transport, which altered endogenous IAA distribution. Use of BG1 in molecular breeding of rice and other plants are disclosed.

Methods of improving an agronomic characteristic of a plant, the method includes modulating the expression of (i) a polynucleotide encoding an amino acid sequence comprising SEQ ID NO: 1 or an amino acid sequence that is at least 95% identical to one of SEQ ID NO: 1 (ii) a polynucleotide that hybridizes under stringent hybridization conditions to a fragment of polynucleotide comprising SEQ ID NO: 2, wherein the fragment comprises at least 100 contiguous nucleotides of SEQ ID NO: 2 (iii) a polynucleotide that encodes an amino acid sequence that is at least 90% identical to SEQ ID NO: 1, (iv) a polynucleotide encoding a polypeptide comprising one or more deletions or insertions or substitutions of amino acids compared to SEQ ID NO: 1.

In an embodiment, the expression of the polynucleotide encoding a polypeptide having at least 95% identity to SEQ ID NO: 1 is increased by transforming the plant with a recombinant polynucleotide operably linked to a heterologous promoter. In an embodiment, the expression of an endogenous polynucleotide encoding a polypeptide having at least 95% identity to SEQ ID NO: 1 is increased by upregulating a regulatory element operably associated with the endogenous polynucleotide. In an embodiment, the expression of the polynucleotide is increased by expressing the polynucleotide under a regulatory element of SEQ ID NO: 3.

In an embodiment, the agronomic characteristic is selected from the group consisting of (i) an increase in grain size, (ii) an increase in grain weight, (iii) an increase in panicle length, (iv) an increase in grain yield (v) an increase in grain filling rate, (vi) an increase in biomass. The increase in agronomic characteristic is measured with respect to a control plant that does not exhibit elevated levels of BG1 (or a variant or an ortholog/homolog thereof). In an embodiment, the agronomic performance is an increase in plant biomass. In an embodiment, the grain weight is increased in relation to a control plant not having an increased expression of the polynucleotide.

In an embodiment, the plant is a monocot. In an embodiment, the plant is rice or maize. In an embodiment, the plant is a dicot. In an embodiment, the plant is soybean.

In an embodiment, methods of improving yield of a plant include increasing the expression of a polynucleotide that encodes a polypeptide comprising the amino acid sequence selected from the group consisting of SEQ ID NOS: 1, 4-27 or an allelic variant thereof.

In an embodiment, methods of improving rice grain yield include the expression of a polynucleotide that encodes a polypeptide comprising the amino acid sequence of SEQ ID NO: 1 or a variant thereof.

In an embodiment, methods of marker assisted selection of a plant or identifying a native trait associated with increased yield, include:

a. performing marker-assisted selection of plants that have one or more variations in genomic regions encoding a protein comprising SEQ ID NO: 1 or a variant thereof or a regulatory sequence thereof; and b. identifying the plant that exhibits higher yield.

In an embodiment, methods of identifying one or more alleles in a population of rice plants that are associated with increased grain yield includes:

a. evaluating in a population of rice plants for one or more allelic variations in (i) a genomic region, the genomic region encoding a polypeptide or (ii) the regulatory region controlling the expression of the polypeptide, wherein the polypeptide comprises the amino acid sequence of SEQ ID NO: 1 or a sequence that is 95% identical to SEQ ID NO: 1;

b. obtaining phenotypic values of increased yield for the one or more rice plants in the population;

c. associating the allelic variations in the genomic region with the phenotype; and d. identifying the one or more alleles that are associated with increased yield.

In an embodiment, an isolated polynucleotide includes for example, (i) encoding an amino acid sequence comprising one of SEQ ID NOS: 1, 4-27 or an amino acid sequence that is at least 95% identical to one of SEQ ID NOS: 1, 4-27 (ii) hybridizing under stringent hybridization conditions to a fragment of polynucleotide selected from the group consisting of SEQ ID NO: 2, wherein the fragment comprises at least 100 contiguous nucleotides of SEQ ID NO: 2 (iii) that encodes an amino acid sequence that is at least 90% identical to SEQ ID NO: 1, (iv) a polynucleotide encoding a polypeptide comprising one or more deletions or insertions or substitution of amino acids compared to SEQ ID NO: 1, wherein the polynucleotide encodes a polypeptide involved in the regulation of grain width, weight or yield.

In an embodiment, a recombinant expression cassette includes the polynucleotide that is operably linked to a regulatory element, wherein the expression cassette is functional in a plant cell. In an embodiment, a host cell includes the expression cassette. In an embodiment, a transgenic plant includes the recombinant expression cassette.

In an embodiment, a transgenic plant part includes a plant regulatory element that operably regulates the expression of a polynucleotide encoding a polypeptide comprising the amino acid sequence of SEQ ID NO: 1 or a variant or an ortholog thereof, wherein the regulatory element is heterologous to the polynucleotide.

In an embodiment, the polynucleotide that regulates the expression comprises a sequence selected from the group consisting of SEQ ID NOS: 7-8 or a functional promoter fragment thereof.

In an embodiment, methods of marker assisted selection of a maize plant for improved yield, includes:
a. detecting one or more genetic variations in a genomic region comprising a polynucleotide encoding a protein selected from the group consisting of SEQ ID NOS: 12-14 or a variant thereof or in a regulatory sequence controlling the expression of the polynucleotide thereof, in a plurality of maize plants; and
b. associating the one or more variations with increased yield and thereby selecting the maize plant that has the one or more variations associated with higher yield.

In an embodiment, methods of identifying one or more alleles associated with increased yield in a population of maize plants, the method comprising:
a. evaluating in a population of maize plants one or more genetic variations in (i) a genomic region encoding a polypeptide or (ii) a regulatory region controlling the expression of the polypeptide, wherein the polypeptide comprises the amino acid sequence selected from the group consisting of SEQ ID NOS: 12-14 or a sequence that is 95% identical to SEQ ID NOS: 12-14;
b. obtaining yield data for one or more maize plants in the population;
c. associating the one or more genetic variations in the genomic region encoding the polypeptide or in the regulatory region controlling the expression of the polypeptide with yield, thereby identifying one or more alleles associated with increased yield.

In an embodiment, the one or more genetic variations is in the coding region of the polynucleotide. In an embodiment, the regulatory region is a promoter element. In an embodiment, the yield is grain yield A method of improving grain width, weight or yield of a plant includes the steps of modulating the expression of (i) a polynucleotide encoding an amino acid sequence comprising one of SEQ ID NOS: 1, 4-27 or an amino acid sequence that is at least 95% identical to one of SEQ ID NOS: 1, 4-27 (ii) a polynucleotide that hybridizes under stringent hybridization conditions to a fragment of a polynucleotide encoding a polypeptide selected from the group consisting of SEQ ID NOS: 1, 4-27, wherein the fragment comprises at least 100 contiguous nucleotides of a polynucleotide encoding a polypeptide selected from the group consisting of SEQ ID NOS: 1, 4-27 (iii) a polynucleotide that encodes an amino acid sequence that is at least 90% identical to SEQ ID NO: 1, (iv) a polynucleotide encoding a polypeptide comprising one or more deletions or insertions or substitution of amino acids compared to SEQ ID NO: 1, wherein the polynucleotide encodes a polypeptide involved in the regulation of grain width, weight or yield.

In an embodiment, the polynucleotide that comprises a fragment of SEQ ID NO: 2, is sufficient to up-regulate the endogenous expression of the polynucleotide that encodes a polypeptide. In an embodiment, the modulation of the expression is achieved through RNA interference.

In an embodiment, the modulation of the expression is achieved through mutagenesis. In an embodiment, the modulation of the expression is achieved through microRNA mediated gene silencing. In an embodiment, the modulation of the expression is achieved through promoter-mediated gene suppression. In an embodiment, the modulation of the expression is achieved through targeted mutagenesis of an endogenous regulatory element.

In an embodiment, the grain weight is increased in relation to a control plant not expressing the polynucleotide.

In an embodiment, the modulation of expression is performed in a monocot. In an embodiment, the plant is rice. In an embodiment, the plant is a dicot.

A method of improving the length to width aspect of rice grain includes the steps of modulating the expression of a polynucleotide that encodes a polypeptide comprising the amino acid sequence of SEQ ID NO: 1 or an allelic variant thereof.

A method of improving rice grain yield, the method includes modulating the expression of a polynucleotide that encodes a polypeptide comprising the amino acid sequence of SEQ ID NO: 1 or a variant thereof.

A method of marker assisted selection of a plant for improved grain size or yield, the method includes the steps of: performing marker-assisted selection of plants that have one or more variations in genomic regions encoding a protein comprising SEQ ID NO: 1 or a variant thereof or a regulatory sequence thereof; and identifying the plant that produces grains with improved grain quality and/or higher yield.

A method of identifying alleles in rice plants or rice germplasm that are associated with improved grain quality and/or increased yield, the method includes the steps of obtaining a population of rice plants, wherein one or more plants exhibit improved grain quality and/or increased yield; evaluating allelic variations with respect to the polynucleotide sequence encoding a protein comprising a polypeptide comprising: SEQ ID NO: 1 or in the genomic region that regulates the expression of the polynucleotide encoding the protein; obtaining phenotypic values of improved grain quality and/or increased yield for a plurality of rice plants in the population; associating the allelic variations in the genomic region associated with the polynucleotide with the phenotype; and identifying the alleles that are associated with improved grain quality and/or increased yield.

In an embodiment, the polynucleotides described herein encode a polypeptide involved in the regulation of grain width, weight or yield.

In an embodiment, a host cell includes the recombinant polynucleotides disclosed herein. In an embodiment, a transgenic plant includes the recombinant expression cassette disclosed herein.

An isolated polynucleotide that operably regulates the expression of a polynucleotide that encodes a polypeptide comprising the amino acid sequence of SEQ ID NO: 1 or a variant thereof. In an embodiment, the polynucleotide that regulates the expression comprises a sequence of SEQ ID NO: 3 or a functional promoter fragment thereof.

TABLE 1

Sequence Description

| SEQ ID NO: | Polynucleotide/ polypeptide | Identity | Description |
|---|---|---|---|
| SEQ ID NO: 1 | polypeptide | OsBG1 protein | *Oryza sativa* |
| SEQ ID NO: 2 | polynucleotide | OsBG1- cDNA | *Oryza sativa* |
| SEQ ID NO: 3 | polynucleotide | OsBG1 promoter | *Oryza sativa* |
| SEQ ID NO: 4 | polypeptide | AT1G54200 | *Arabidopsis thaliana* |
| SEQ ID NO: 5 | polypeptide | AT3G13980 | *Arabidopsis thaliana* |
| SEQ ID NO: 6 | polypeptide | AT5G12050 | *Arabidopsis thaliana* |
| SEQ ID NO: 7 | polypeptide | AT3G42800 | *Arabidopsis thaliana* |
| SEQ ID NO: 8 | polypeptide | Bra037972 | *Brassica rapa* |
| SEQ ID NO: 1 | polypeptide | Bra030898 | *Brassica rapa* |
| SEQ ID NO: 10 | polypeptide | Os03g0175800 | *Oryza sativa* |
| SEQ ID NO: 11 | polypeptide | Os10g0397600 | *Oryza sativa* |
| SEQ ID NO: 12 | polypeptide | GRMZM2G007134 | *Zea mays* |
| SEQ ID NO: 13 | polypeptide | GRMZM2G438606 | *Zea mays* |
| SEQ ID NO: 14 | polypeptide | GRMZM2G178852 | *Zea mays* |
| SEQ ID NO: 15 | polypeptide | Sb01g023080 | *Sorghum bicolor* |
| SEQ ID NO: 16 | polypeptide | Sb01g045450 | *Sorghum bicolor* |
| SEQ ID NO: 17 | polypeptide | Bradi1g72920 | *Brachypodium distachyon* |
| SEQ ID NO: 18 | polypeptide | Medtr5g049030 | *Medicago truncatula* |
| SEQ ID NO: 19 | polypeptide | Medtr3g139450 | *Medicago truncatula* |
| SEQ ID NO: 20 | polypeptide | POPTR_0003s06210 | *Populus trichocarpa* |
| SEQ ID NO: 21 | polypeptide | POPTR_0001s17050 | *Populus trichocarpa* |
| SEQ ID NO: 22 | polypeptide | Glyma04g05780 | *Glycine max* |
| SEQ ID NO: 23 | polypeptide | Glyma07g04110 | *Glycine max* |
| SEQ ID NO: 24 | polypeptide | Glyma16g00820 | *Glycine max* |
| SEQ ID NO: 25 | polypeptide | Si036603m | *Setaria italica* |
| SEQ ID NO: 26 | polypeptide | Si036624m | *Setaria italica* |
| SEQ ID NO: 27 | polypeptide | GSVIVG01016780001 | *Vitis vinifera* |
| SEQ ID NO: 28 | oligo | SF1 | Site-Finding PCR primer |
| SEQ ID NO: 29 | oligo | SFP1 | Site-Finding PCR primer |
| SEQ ID NO: 30 | oligo | SFP2 | Site-Finding PCR primer |
| SEQ ID NO: 31 | oligo | GSP1 | Site-Finding PCR primer |
| SEQ ID NO: 32 | oligo | GSP2 | Site-Finding PCR primer |
| SEQ ID NO: 33 | oligo | GeneRacer 5' primer | RACE primer |
| SEQ ID NO: 34 | oligo | GeneRacer RNA Oligo | RACE primer |
| SEQ ID NO: 35 | oligo | Sequence | RACE primer |
| SEQ ID NO: 36 | oligo | BG1-1R | RACE primer |
| SEQ ID NO: 37 | oligo | BG1-2R | RACE primer |
| SEQ ID NO: 38 | oligo | BG1-3R | RACE primer |
| SEQ ID NO: 39 | oligo | BG1-F | Real-time PCR primer |
| SEQ ID NO: 40 | oligo | BG1-R | Real-time PCR primer |
| SEQ ID NO: 41 | oligo | Ubiquitin-F | Real-time PCR primer |
| SEQ ID NO: 42 | oligo | Ubiquitin-R | Real-time PCR primer |
| SEQ ID NO: 43 | oligo | Actin-F | Real-time PCR primer |
| SEQ ID NO: 44 | oligo | Actin-R | Real-time PCR primer |
| SEQ ID NO: 45 | oligo | CDKA1-F | Real-time PCR primer |
| SEQ ID NO: 46 | oligo | CDKA1-R | Real-time PCR primer |
| SEQ ID NO: 47 | oligo | E2F2-F | Real-time PCR primer |
| SEQ ID NO: 48 | oligo | E2F2-R | Real-time PCR primer |
| SEQ ID NO: 49 | oligo | H1-F | Real-time PCR primer |
| SEQ ID NO: 50 | oligo | H1-R | Real-time PCR primer |
| SEQ ID NO: 51 | oligo | CYCD1; 1-F | Real-time PCR primer |
| SEQ ID NO: 52 | oligo | CYCD1; 1-R | Real-time PCR primer |
| SEQ ID NO: 53 | oligo | CYCT1-F | Real-time PCR primer |
| SEQ ID NO: 54 | oligo | CYCT1-R | Real-time PCR primer |
| SEQ ID NO: 55 | oligo | OsEXPA5-F | Real-time PCR primer |
| SEQ ID NO: 56 | oligo | OsEXPA5-R | Real-time PCR primer |
| SEQ ID NO: 57 | oligo | OsEXPA10-F | Real-time PCR primer |
| SEQ ID NO: 58 | oligo | OsEXPA10-R | Real-time PCR primer |
| SEQ ID NO: 59 | oligo | OsEXPBS-F | Real-time PCR primer |
| SEQ ID NO: 60 | oligo | OsEXPBS-F | Real-time PCR primer |
| SEQ ID NO: 61 | oligo | OsEXPB4-R | Real-time PCR primer |
| SEQ ID NO: 62 | oligo | OsEXPB4-F | Real-time PCR primer |
| SEQ ID NO: 63 | oligo | OsEXPB7-F | Real-time PCR primer |
| SEQ ID NO: 64 | oligo | OsEXPB7-R | Real-time PCR primer |
| SEQ ID NO: 65 | oligo | BG1OX-F | Vector Primer |
| SEQ ID NO: 66 | oligo | BG1OX-F | Vector Primer |
| SEQ ID NO: 67 | oligo | BG1RNAi-F | Vector Primer |
| SEQ ID NO: 68 | oligo | BG1RNAi-R | Vector Primer |
| SEQ ID NO: 69 | oligo | BG1GUS-F | Vector Primer |
| SEQ ID NO: 70 | oligo | BG1GUS-R | Vector Primer |
| SEQ ID NO: 71 | oligo | BG1EGFP-F | Vector Primer |
| SEQ ID NO: 72 | oligo | BG1EGFP-R | Vector Primer |

TABLE 1-continued

Sequence Description

| SEQ ID NO: | Polynucleotide/ polypeptide | Identity | Description |
|---|---|---|---|
| SEQ ID NO: 73 | oligo | BG1DNAOX-F | Vector Primer |
| SEQ ID NO: 74 | oligo | BG1DNAOX-R | Vector Primer |
| SEQ ID NO: 75 | oligo | BG1 RNAi fragment | dsRNA |

In another aspect, the present disclosure relates to a recombinant expression cassette comprising a nucleic acid as described. Additionally, the present disclosure relates to a vector containing the recombinant expression cassette. Further, the vector containing the recombinant expression cassette can facilitate the transcription and translation of the nucleic acid in a host cell. The present disclosure also relates to the host cells able to express the polynucleotide of the present disclosure. A number of host cells could be used, such as but not limited to, microbial, mammalian, plant or insect.

In yet another embodiment, the present disclosure is directed to a transgenic plant or plant cells, containing the nucleic acids of the present disclosure. Preferred plants containing the polynucleotides of the present disclosure include but are not limited to maize, soybean, sunflower, sorghum, canola, wheat, alfalfa, cotton, rice, barley, tomato and millet. In another embodiment, the transgenic plant is a maize plant or plant cells. Another embodiment is the transgenic seeds from the transgenic nitrate uptake-associated polypeptide of the disclosure operably linked to a promoter that drives expression in the plant. The plants of the disclosure can have improved grain quality as compared to a control plant.

DETAILED DESCRIPTION OF THE DRAWINGS

FIG. 1 shows the phenotype of the Bg1-D mutant. (A). 10-day-old seedlings grown on ½ MS medium. Scale bar, 5 cm. (B and C). Growth phenotype of 2-month-old (B) and 4-month-old (C) plants grown in a paddy field. Scale bar, 10 cm. (D and E). The young panicles (D) and harvested panicles (E) showed an increased length for Bg1-D. Scale bar, 5 cm. (F). The mature seed showed an increased size for Bg1-D. Scale bar, 10 mm.

Figure 2:
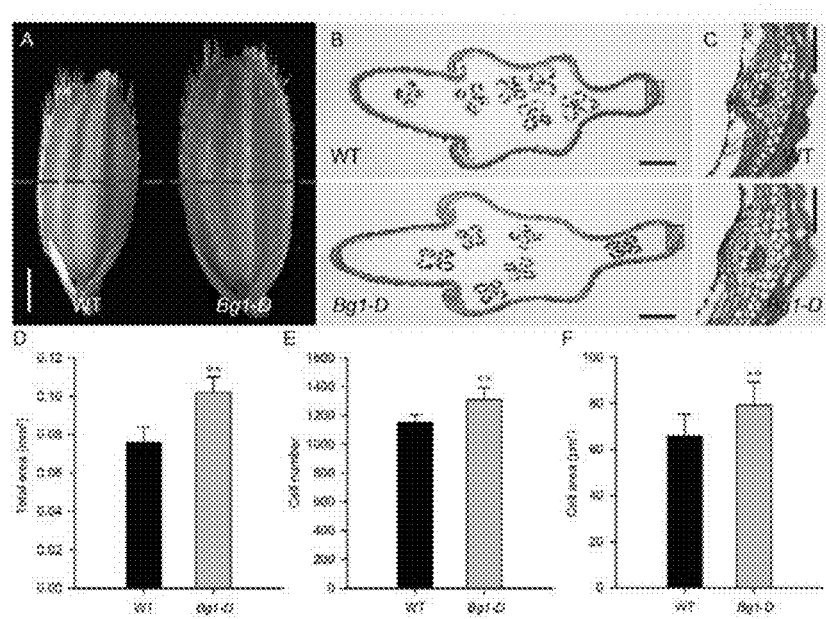

FIG. 2 shows the histological analyses of spikelet hulls before heading. (A). Spikelets of WT and Bg1-D plants. Scale bar, 2 mm. (B). Cross-sections of spikelet hulls. Dashed line indicates the position of cross-section. Scale bar, 0.5 mm. (C). Magnified view of the cross-section boxed in B. Scale bar, 0.1 mm. (D-F). Total area (D), cell number (E) and cell area (F) in the outer parenchyma layer of the spikelet hulls formed by WT and Bg1-D plants. All data are given as means±S.D. (n=15). A Students t-test was used to generate the P values. **P<0.01.

Figure 3:
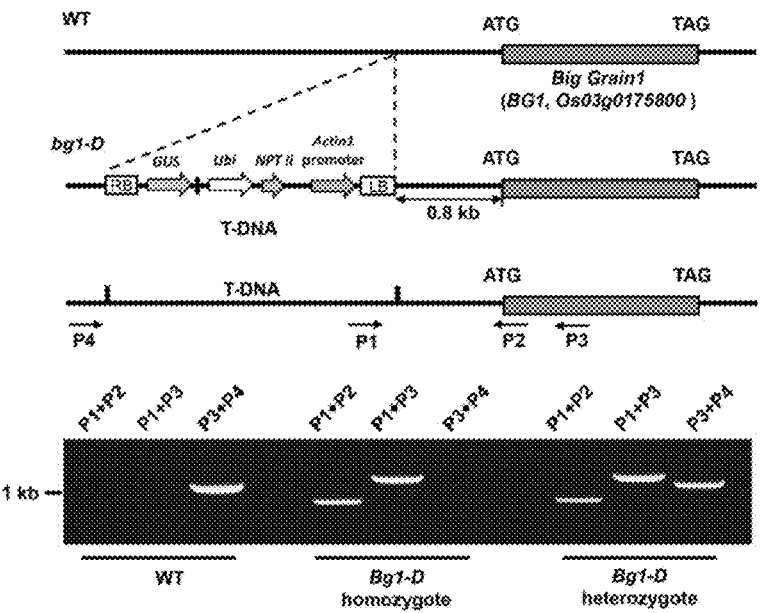
Figure 3:
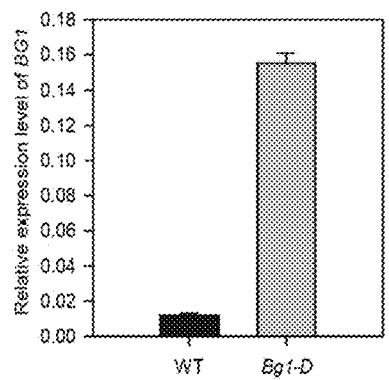

FIG. 3 shows identification of BG1 gene. (A). Schematic map of the T-DNA flanking region of the Bg1-D mutant. A candidate for the ORF responsible for the phenotype (Os03g0175800, which encodes a novel protein with unknown function, colored blue), referred to as BG1, is located 0.8-kb downstream of the T-DNA insertion. The rice Actin1 promoter is shown by the green arrow, LB and RB are left and right borders of the T-DNA. (B). The expression level of BG1 mRNA in the wild-type and Bg1-D plants. Data were obtained from three independent replicates. Values are showed as means±S.D.

Figure 4:
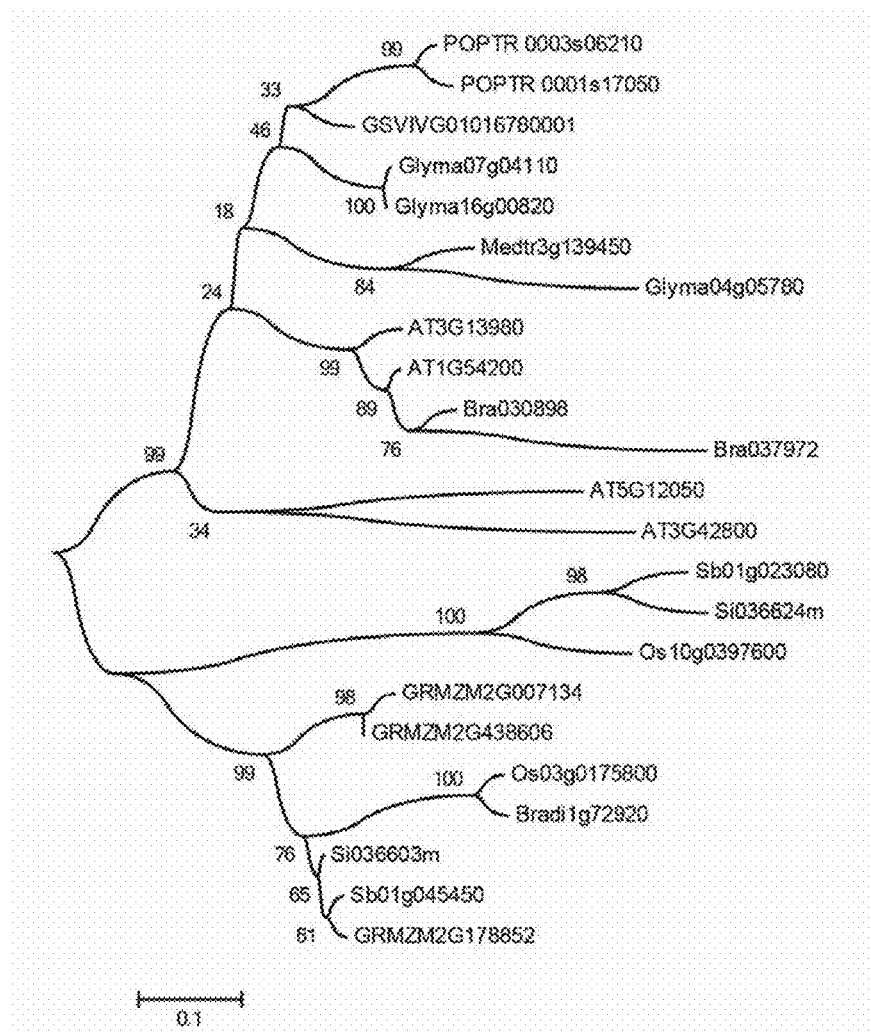

FIG. 4 shows the phylogenetic analysis of BG1.MEGA4 Neighbor-Joining tree was inferred from the amino acid sequences of the BG1 (Os03g0175800) homologs among green plants. Bootstrap values are based on 1000 replications and are indicated in their respective nodes. The scale bar indicates genetic distance based on branch length. SEQ ID NOS: 1, 4-27 represent the sequences shown in the phylogeny of BG1.

Figure 5:
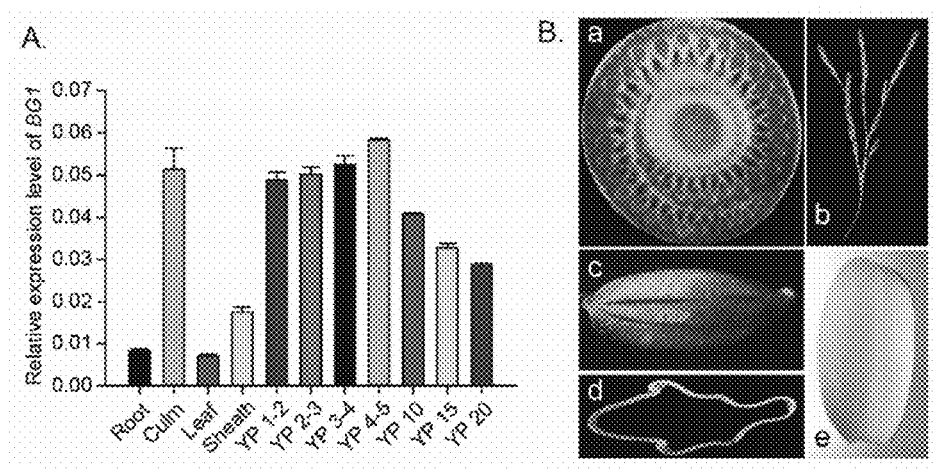

FIG. 5 shows the expression pattern of BG1. (A). Expression of BG1 in various organs analyzed by quantitative RT-PCR analysis. Root, culm, leaf and sheath were harvested in 2-month-old wild-type (Nipponpare) plants. Different length of young panicles (YP) were used for analysis, number indicates the length in centimeters. Data were obtained from three independent replicates. (B). GUS staining of PROBG1:GUS transgenic line tissues. (a) Microscopic observation of a cross-section of young culm. (b) young spikelet. (c) Developing hull. (d) Cross-section of the hull. (e) mature grain.

Figure 6:
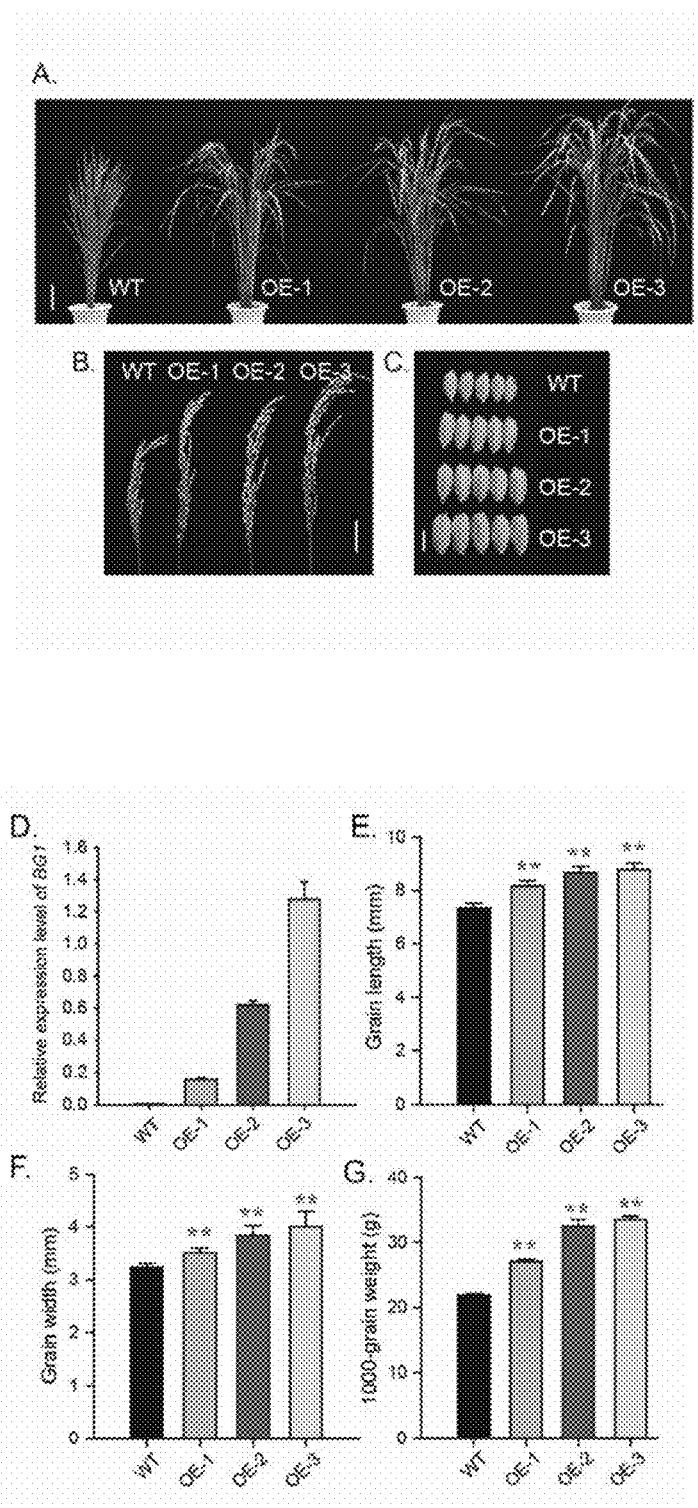

FIG. 6 shows increased grain size and weight in transgenic rice plants overexpressing BG1. (A). Gross morphology of wild-type (WT), OE-1, OE-2 and OE-3 transgenic plants. Scale bar, 20 cm. (B). Comparison of panicle length of the wild-type and transgenic plants is shown. Scale bar, 5 cm. (C). The grain morphologies of wild-type and transgenic plants are shown. Scale bar, 5 mm. (D) Relative expression level of BG1 mRNA in wild-type and transgenic plants. Data were obtained from three independent replicates. (E-F). Comparison of the grain length (E), grain width (F), and 1000-grain weight (G) of wild-type and transgenic plants are shown. (A-E). OE-1, OE-2, OE-3 indicate three representative transgenic lines of BG1 overexpression. (E-G) Values are showed as means±S.D. (n=20 in E and F, n=5 in G). **P<0.01 (t-test).

Figure 7:
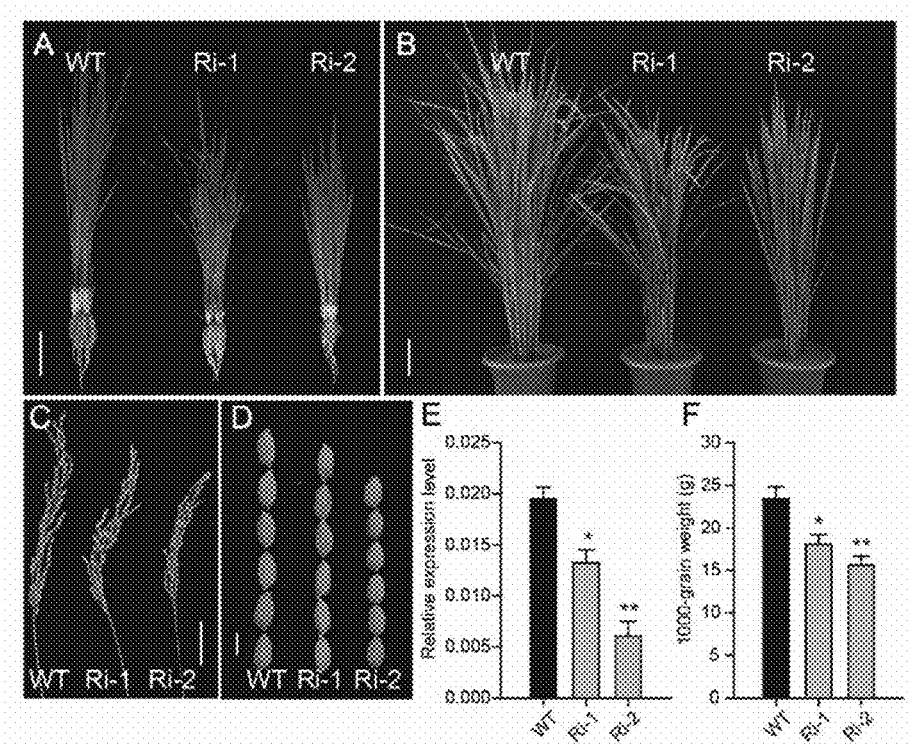

FIG. 7 shows phenotypes BG1-RNAi plants (Ri). (A and B). Overall morphology of wild-type (WT) and BG1-RNAi plants are shown. 60-day-old (A), Scale bar, 10 cm. 100-day-old (B). Scale bar, 10 cm. (C) Comparison of panicle length of the wild-type and BG1-RNAi plants. Scale bar, 5 cm. (D). The grain morphologies of wild-type and BG1-RNAi plants are shown. Scale bar, 5 mm. (E) Relative expression level of BG1 mRNA in wild-type and BG1-RNAi plants. Data were obtained from three independent replicates. (F). Comparison of 1000-grain weight of the wild-type and BG1-RNAi plants. Values are showed as means±S.D. (n=5). *P<0.05, **P<0.01 (t-test). (A-F). Ri-1, Ri-2 indicate two representative transgenic lines of BG1-RNAi plants.

Figure 8:
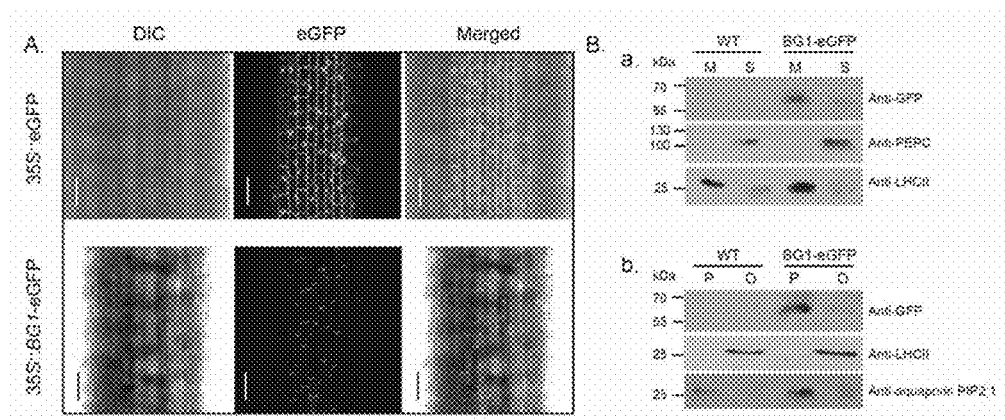

FIG. 8 shows that BG1 localizes primarily to the plasma membrane. (A). Confocal micrographs of rice root showed plasma membrane targeting of BG1. Rice transformed with pCambia 35S::eGFP (upper panel) and pCambia 35S::BG1-eGFP (lower panel) plasmids are shown. Bar, 50 μM. DIC indicates the differential interference contrast phase, eGFP indicates the enhanced green fluorescence of proteins, and merged indicates the merging of eGFP and DIC. (B). Immunoblot analysis of BG1 in the protein extracts of seedlings. (a). Microsomal pellet (P) and soluble (S) fraction were isolated in 7-day-old young seedlings. (b). Fractions of two-phase membrane partitioning, plasma membrane (P) and other membrane (O). PEPC (phosphoenolpyruvate carboxylase) was used as cytosolic control, LHCII and aquaporin PIP2;1 were used as other membrane and plasma membrane control.

Figure 9:
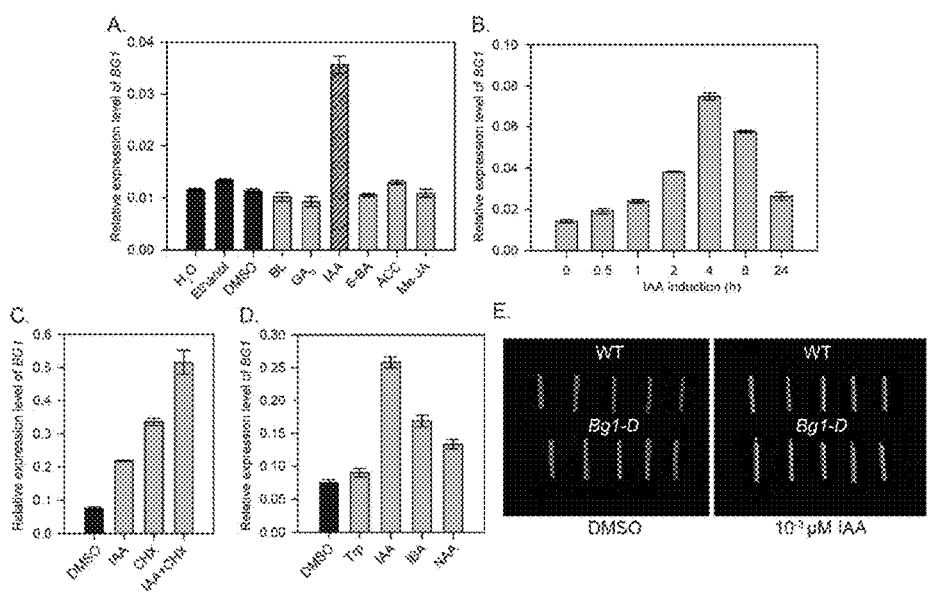

FIG. 9 shows that BG1 is an auxin response gene. Relative expression level of BG1 under different phytohormone treatments. (B) Time course of BG1 response to 10 μM IAA treatment. (C) Cycloheximide leads to increased expression level of BG1. (D) BG1 response to different auxin compounds. (A-D) Data were obtained from three independent replicates. Bars represent means±SD (n=3) (E) BG1 gene promote auxin-induced growth in the elongating leaf sheath.

Figure 10:
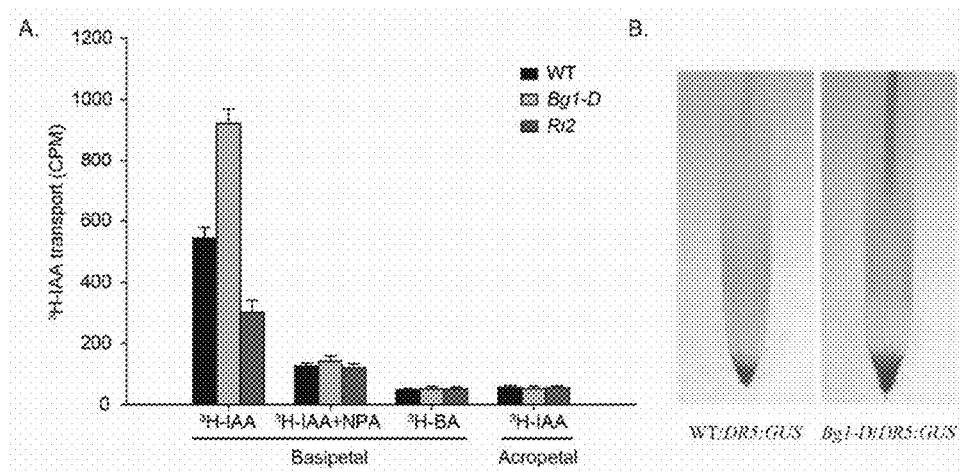

FIG. 10 shows that Bg1-D displayed enhanced polar auxin transport (PAT).

Comparison of PAT between wild-type, Bg1-D and BG1-RNAi (Ri2) plants in dark-grown coleoptiles. Bars represent means±SD (n=5). Asterisks indicate the significance of differences determined by Student's t-test: ** $0.001 \leq P < 0.01$.

Figure 11:
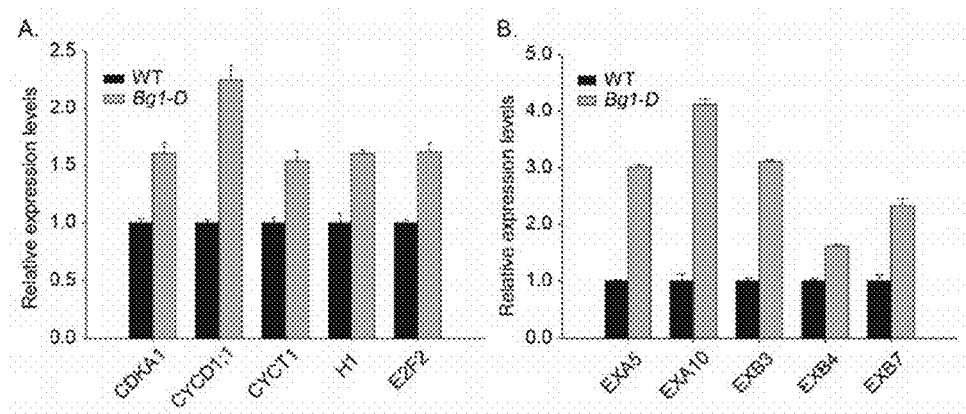

FIG. 11 shows the expression level of genes involved in cell cycle and cell expansion in WT and Bg1-D. (A) Genes involved in cell cycle G1 to S phase were upregulated in Bg1-D. (B) Expansion gene involved in cell expansion were upregulated in Bg1-D. Bars represent means±SD (n=3).

Figure 12:
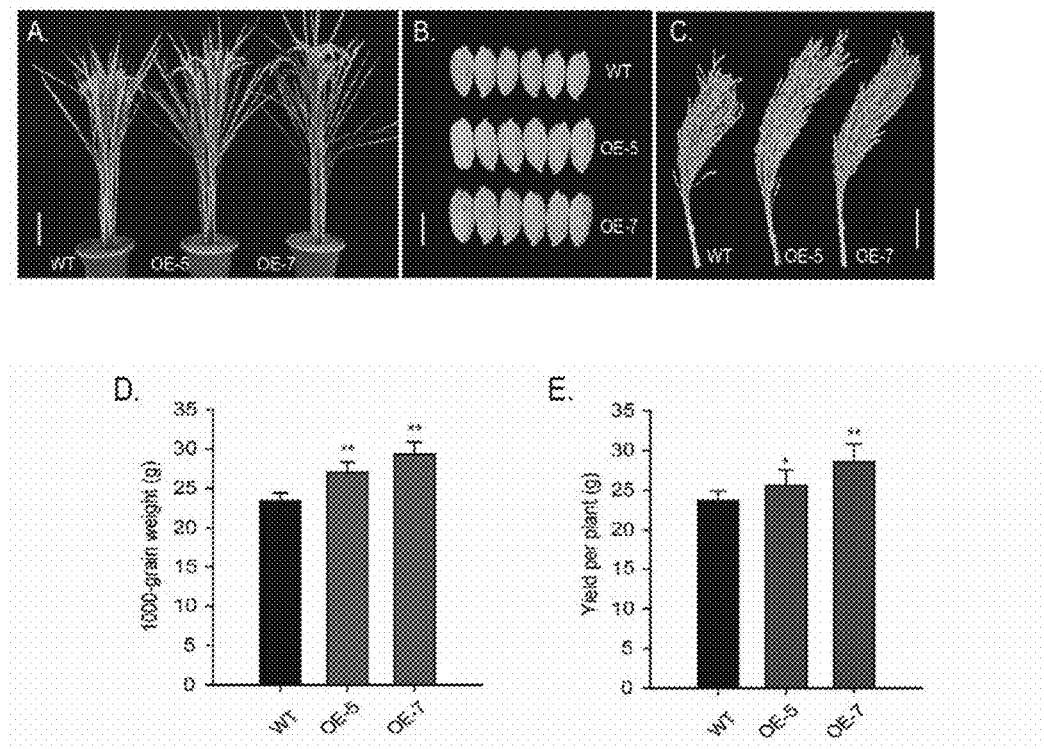

FIG. 12 shows increased grain yield in transgenic rice plants overexpressing BG1 by its native promoter. (A). Gross morphology of wild-type (WT), OE-5 and OE-7 transgenic plants. Scale bar, 20 cm. (B). The grain morphologies of wild-type and transgenic plants. Scale bar, 5 mm. (C). Comparison of the total panicles per plant harvested in the wild-type and transgenic plants. Scale bar, 5 cm. (D and E). Comparison of the 1000-grain weight (D) and yield per plant of wild-type and transgenic plants (E). (A-E). OE-5, OE-7 indicate two representative transgenic lines of BG1 overexpression driven by BG1 native promoter. (D-E) Values are showed as means±S.D. (n=10 in D and n=25 in G). *$0.01 \leq P < 0.05$, ** $0.001 \leq P < 0.01$ (student's t-test).

Figure 13:
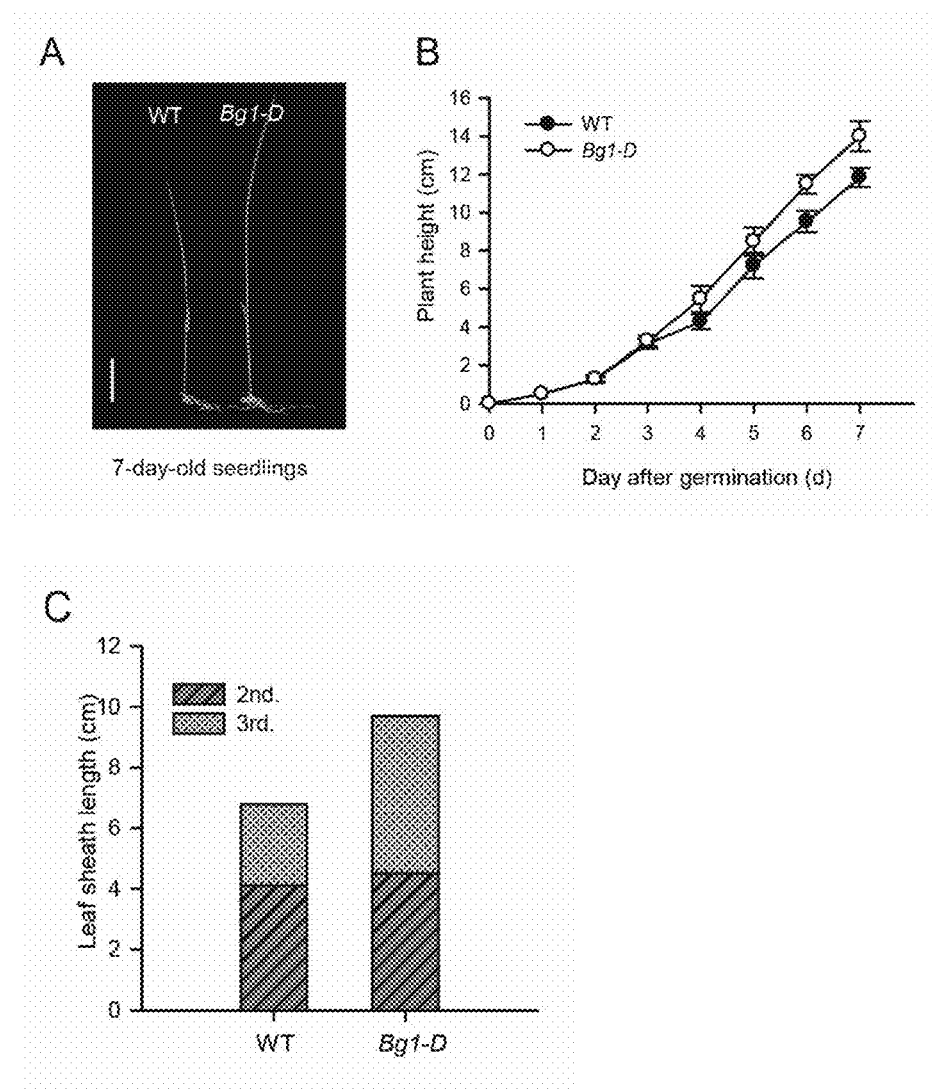

FIG. 13 shows accelerated growth of Bg1-D seedlings. (A) 7-day-old seedlings of wild-type and Bg1-D plants. Scale bar, 2 cm. (B) Comparison of plant height between wild-type and Bg1-D plants after seed germination in a week. (C) Comparison of length of leaf sheath between wild-type and Bg1-D plants in 7-day-old seedlings. Data are given as mean±S.E. (n=20).

Figure 14:
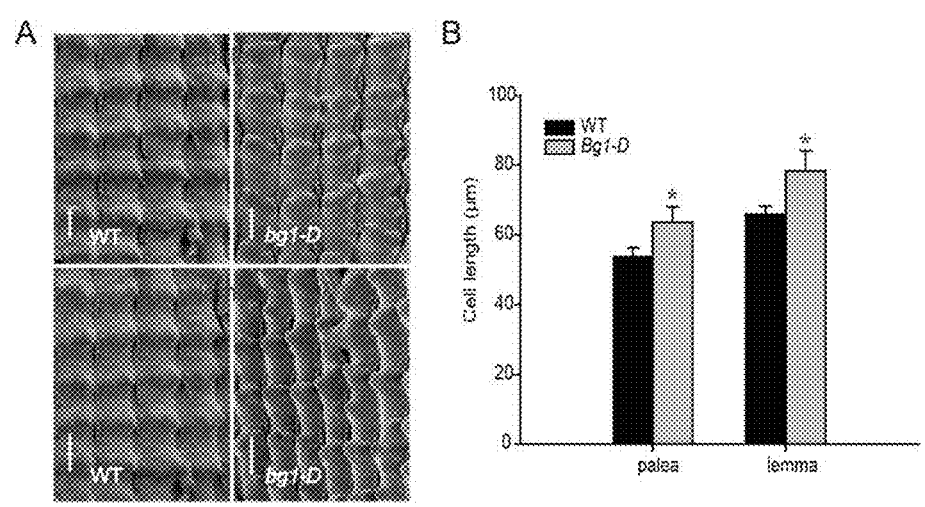

FIG. 14 shows increased cell length in the spikelet hull of Bg1-D. (A) Close-up view of longitudinal sections of spikelet hull. Scale bar, 50 μm. (B) Comparison of cell length of palea and lemma cell layer between wild-type and Bg1-D plants. Data are given as mean±SE (n=15). A Student's t-test was used to generate the P values. ** $0.001 \leq P < 0.01$.

Figure 15:
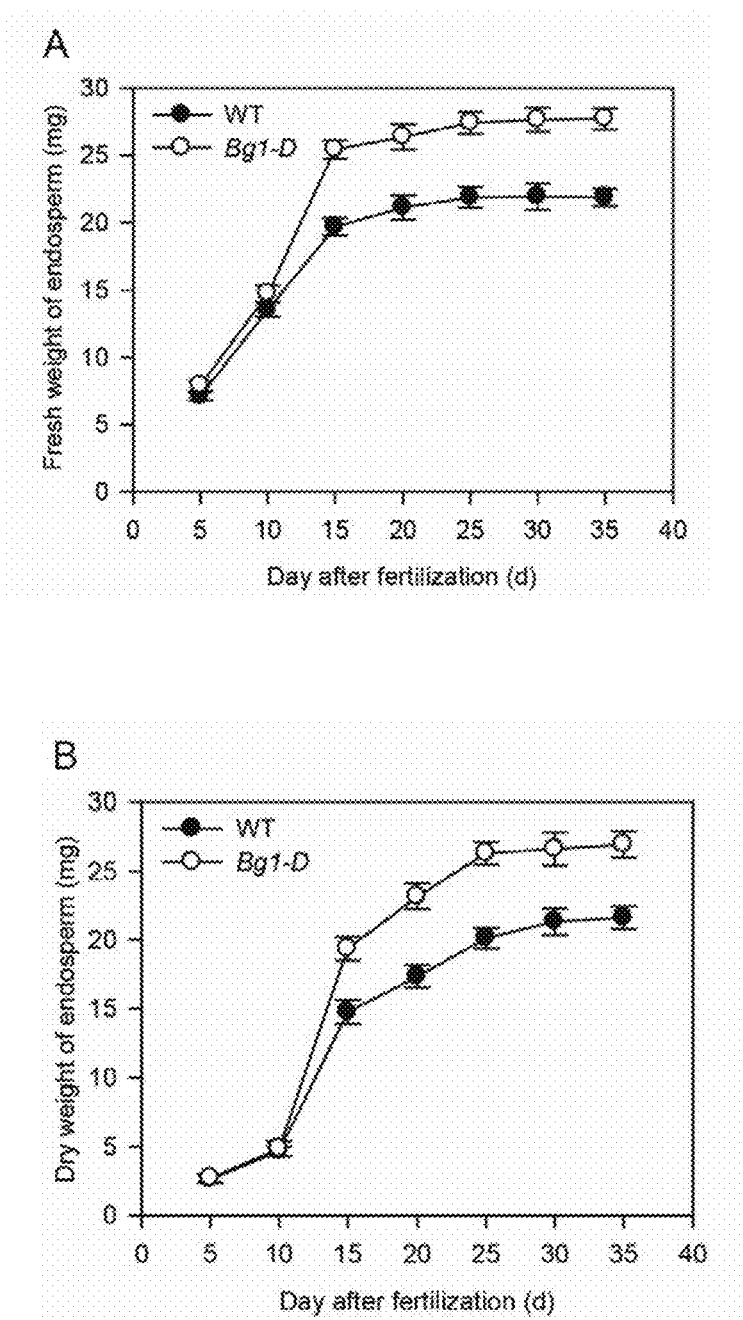

FIG. 15 demonstrates that Bg1-D showed increased grain filling rate. (A) Comparison of fresh weight of endosperm in WT and Bg1-D after fertilization. (B) Comparison of dry weight of endosperm in WT and Bg1-D after fertilization. Data are given as mean±SE (n=40).

Figure 16:
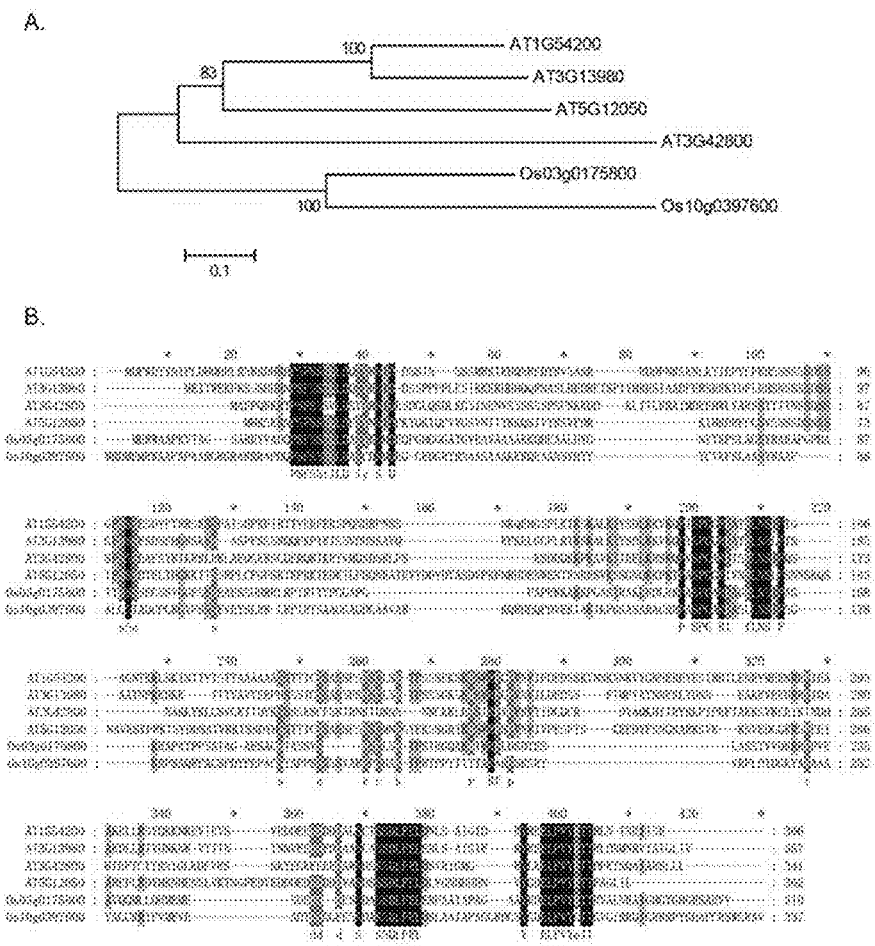

FIG. 16 shows phylogenetic and amino acid sequences analysis of BG1 in rice and Arabidopsis. (A) Phylogenetic relationships of BG1 (SEQ ID NOS: 4, 5, 7, 10 or 1, and 11 in that order). Conserved amino acids are highlighted in shades of black and gray: white letters with black background (100% identity), white letters with gray background (80% identity), and black letters with gray background (60% identity). See also Global Identity (Table 2) and Global Similarity (Table 3) disclosed herein.

Figure 17:
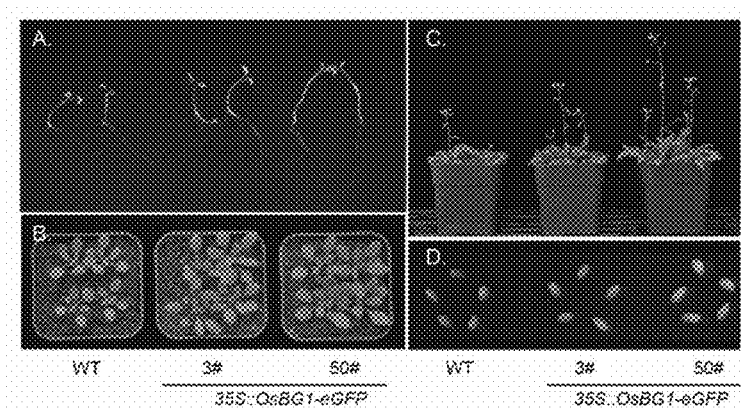

FIG. 17 shows that overexpression of OsBG1 leads to increased organ size in Arabidopsis. (A) Elongated hypocotyls of 5-day-old seedlings overexpressing OsBG1 (B-D) OsBG1 promotes increased leaf size (B), stem length (C) and seed size (D). 3# and 50# indicate two representative transgenic lines of OsBG1 overexpression in Arabidopsis driven by 35S promoter.

Figure 18:
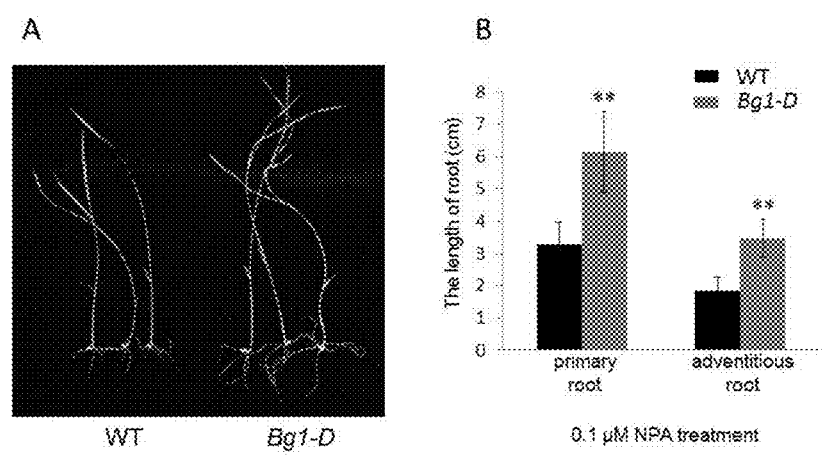

FIG. 18 shows that Activation of BG1 led to increased polar auxin transport (PAT) (A) Phenotypes of 7-day-old seedlings treated with 0.1 μM NAA. (B) Comparison of the length of root between WT and Bg1-D plants. Data are given as mean±SE (n=20). A Student's t-test was used to generate the P values. ** $0.001 \leq P < 0.01$.

Figure 19:
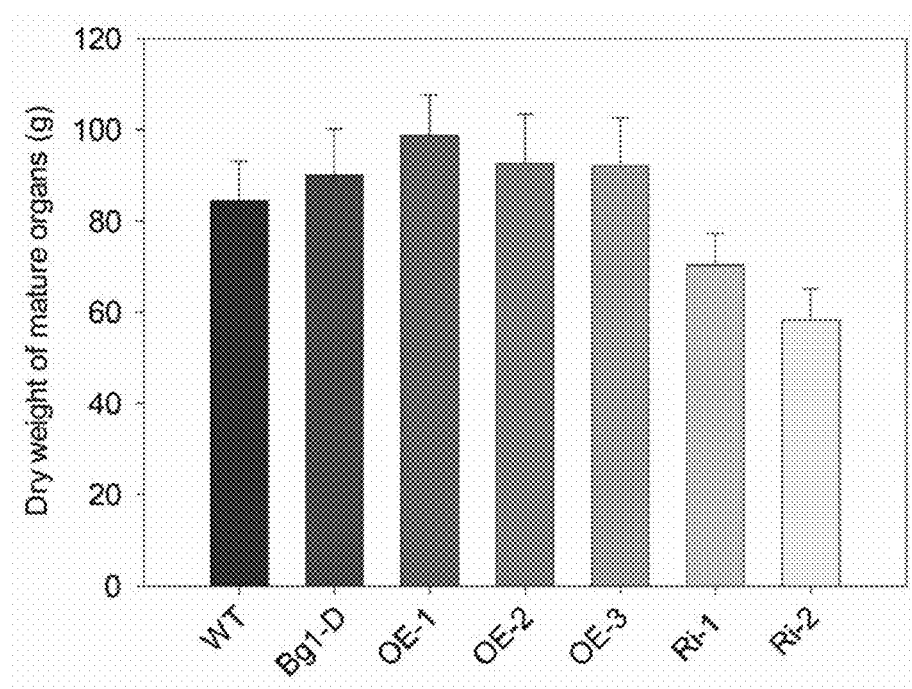

FIG. 19 demonstrates that activation of BG1 leads to increased biomass. The biomass was calculated by the dry weight of mature organs. OE-1, OE-2 and OE-3 indicated three independent transgenic lines. Ri-1 and Ri-2 indicated two representative transgenic plants of BG1-RNAi. Bars represent means±SD (n=20).

DETAILED DESCRIPTION

Grain size is a desirable component of grain yield for example, in rice and has been under selection since cereals were first domesticated.

A method of producing a seed, the method comprising: (a) crossing a first plant with a second plant, wherein at least one of the first plant and the second plant comprises a recombinant DNA construct, wherein the recombinant DNA construct comprises a polynucleotide operably linked to at least one heterologous regulatory element, wherein the polynucleotide encodes a polypeptide having an amino acid sequence of at least 70%, 75%, 80%, 85%, 90%, 91%, 92%, 93%, 94%, 95%, 96%, 97%, 98%, 99% or 100% sequence identity, based on the Clustal V or the Clustal W method of alignment, using the respective default parameters, when compared to SEQ ID NOS: 1, 4-27; and (b) selecting a seed of the crossing of step (a), wherein the seed comprises the recombinant DNA construct. A plant grown from the seed may exhibit at least one trait selected from the group consisting of: increased nitrogen stress tolerance, increased yield, increased biomass, and altered root architecture, when compared to a control plant not comprising the recombinant DNA construct. The polypeptide may be over-expressed in at least one tissue of the plant, or during at least one condition of abiotic stress, or both. The plant may be selected from the group consisting of: maize, soybean, sunflower, sorghum, canola, wheat, alfalfa, cotton, rice, barley, millet, sugar cane and switchgrass.

A method of producing a plant that exhibits an increase in at least one trait selected from the group consisting of: increased nitrogen stress tolerance, increased yield, increased biomass, and altered root architecture, wherein the method comprises growing a plant from a seed comprising a recombinant DNA construct, wherein the recombinant DNA construct comprises a polynucleotide operably linked to at least one heterologous regulatory element, wherein the polynucleotide encodes a polypeptide having an amino acid sequence of at least 70%, 75%, 80%, 85%, 90%, 91%, 92%, 93%, 94%, 95%, 96%, 97%, 98%, 99% or 100% sequence identity, based on the Clustal V or the Clustal W method of alignment, using the respective default parameters, when compared to SEQ ID NOS: 1, 4-27, wherein the plant exhibits at least one trait selected from the group consisting of: increased nitrogen stress tolerance, increased yield, increased biomass, and altered root architecture, when compared to a control plant not comprising the recombinant DNA construct. The polypeptide may be over-expressed in at least one tissue of the plant, or during at least one condition of abiotic stress, or both. The plant may be selected from the group consisting of: maize, soybean, sunflower, sorghum, canola, wheat, alfalfa, cotton, rice, barley, millet, sugar cane and switchgrass.

The practice of the present disclosure will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, (1982) *Botany: Plant Biology and Its Relation to Human Affairs*, John Wiley; *Cell Culture and Somatic Cell Genetics of Plants*, vol. 1, Vasil, ed. (1984); Stanier, et al., (1986) *The Microbial World*, 5$^{th}$ ed., Prentice-Hall; Dhringra and Sinclair, (1985) *Basic Plant Pathology Methods*, CRC Press; Maniatis, et al., (1982) *Molecular Cloning: A Laboratory Manual*; *DNA Cloning*, vols. I and II, Glover, ed. (1985); *Oligonucleotide Synthesis*, Gait, ed. (1984); *Nucleic Acid Hybridization*, Hames and Higgins, eds. (1984) and the series *Methods in Enzymology*, Colowick and Kaplan, eds, Academic Press, Inc., San Diego, Calif.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS) and strand displacement amplification (SDA). See, e.g., *Diagnostic Molecular Microbiology: Principles and Applications*, Persing, et al., eds., American Society for Microbiology, Washington, D.C. (1993). The product of amplification is termed an amplicon.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N terminal and C terminal portions of the polypeptide molecule would also not be expected to alter the activity of the polypeptide. Each of the proposed modifications is well within the routine skill in the art, as is determination of retention of biological activity of the encoded products.

The protein disclosed herein may also be a protein which comprises an amino acid sequence comprising deletion, substitution, insertion and/or addition of one or more amino acids in an amino acid sequence selected from the group consisting of SEQ ID NO: 1 or variants thereof. The substitution may be conservative, which means the replacement of a certain amino acid residue by another residue having similar physical and chemical characteristics. Non-limiting examples of conservative substitution include replacement between aliphatic group-containing amino acid residues such as Ile, Val, Leu or Ala, and replacement between polar residues such as Lys-Arg, Glu-Asp or Gln-Asn replacement.

Proteins derived by amino acid deletion, substitution, insertion and/or addition can be prepared when DNAs encoding their wild-type proteins are subjected to, for example, well-known site-directed mutagenesis (see, e.g., Nucleic Acid Research, Vol. 10, No. 20, p. 6487-6500, 1982, which is hereby incorporated by reference in its entirety). As used herein, the term "one or more amino acids" is intended to mean a possible number of amino acids which may be deleted, substituted, inserted and/or added by site-directed mutagenesis.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages, and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

Techniques for allowing deletion, substitution, insertion and/or addition of one or more amino acids in the amino acid sequences of biologically active peptides such as enzymes while retaining their activity include site-directed mutagenesis mentioned above, as well as other techniques such as those for treating a gene with a mutagen, and those in which a gene is selectively cleaved to remove, substitute, insert or add a selected nucleotide or nucleotides, and then ligated.

The protein disclosed herein may also be a protein which is encoded by a nucleic acid comprising a nucleotide sequence comprising deletion, substitution, insertion and/or addition of one or more nucleotides in a nucleotide sequence selected from the group consisting of sequences encoding SEQ ID NOS: 1, 4-27. Nucleotide deletion, substitution, insertion and/or addition may be accomplished by site-directed mutagenesis or other techniques as mentioned above.

The protein disclosed herein may also be a protein which is encoded by a nucleic acid comprising a nucleotide sequence hybridizable under stringent conditions with the complementary strand of a nucleotide sequence selected from the group consisting of sequences encoding SEQ ID NOS: 1, 4-27.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system. Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Yamao, et al., (1985) *Proc. Natl. Acad. Sci. USA* 82:2306-9) or the ciliate *Macronucleus*, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present disclosure may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species or, if from the same species, is substantially modified from its native form in composition and/or genomic locus by deliberate human intervention. Heterologous may also indicate that a particular nucleic acid is foreign to its location in the genome as compared to its native location in the genome. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the disclosure, which contains a vector and supports the replication and/or expression of the expression vector. Host cells may be prokaryotic cells such as *E. coli*, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, canola, barley, millet and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "nitrate uptake-associated nucleic acid" means a nucleic acid comprising a polynucleotide ("nitrate uptake-associated polynucleotide") encoding a full length or partial length nitrate uptake-associated polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) *Guide To Molecular Cloning Techniques*, from the series *Methods in Enzymology*, vol. 152, Academic Press, Inc., San Diego, Calif.; Sambrook, et al., (1989) *Molecular Cloning: A Laboratory Manual*, 2$^{nd}$ ed., vols. 1-3; and *Current Protocols in Molecular Biology*, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter, and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the disclosure, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly preferred plant is *Zea mays*.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions. Suitable constitutive promoters include for example, Ubiquitin promoters, actin promoters, and GOS2 promoter (de Pater et al (1992), The Plant Journal, 2: 837-844).

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed and a promoter.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG® programs (Accelrys, Inc., San Diego, Calif.).). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65 and Pearson, et al., (1994) *Meth. Mol. Biol.* 24:307-31. The preferred program to use for optimal global alignment of multiple sequences is PileUp (Feng and Doolittle, (1987) *J. Mol. Evol.*, 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences. See, *Current Protocols in Molecular Biology*, Chapter 19, Ausubel et al., eds., Greene Publishing and Wiley-Interscience, New York (1995).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Variant Nucleotide Sequences in the Non-Coding Regions

The nitrate uptake-associated nucleotide sequences are used to generate variant nucleotide sequences having the nucleotide sequence of the 5'-untranslated region, 3'-untranslated region or promoter region that is approximately 70%, 75%, 80%, 85%, 90% and 95% identical to the original nucleotide sequence of the corresponding SEQ ID NO: 1. These variants are then associated with natural variation in the germplasm for component traits related to grain quality and/or grain yield. The associated variants are used as marker haplotypes to select for the desirable traits.

Variant Amino Acid Sequences of OsBG1-Associated Polypeptides

Variant amino acid sequences of OsBG1-associated polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using a protein alignment, an appropriate amino acid can be changed. Once the targeted amino acid is identified, the procedure outlined herein is followed. Variants having about 70%, 75%, 80%, 85%, 90% and 95% nucleic acid sequence identity are generated using this method. These variants are then associated with natural variation in the germplasm for component traits related to grain quality and/or grain yield. The associated variants are used as marker haplotypes to select for the desirable traits.

Synthetic Methods for Constructing Nucleic Acids

The isolated nucleic acids of the present disclosure can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20):1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68 and the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present disclosure provides 5' and/or 3' UTR regions for modulation of translation of heterologous coding sequences.

Plant Transformation Methods

Numerous methods for introducing foreign genes into plants are known and can be used to insert a nitrate uptake-associated polynucleotide into a plant host, including biological and physical plant transformation protocols. See, e.g., Miki, et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch et al., (1985) *Science* 227:1229-31), electroporation, microinjection and biolistic bombardment.

Expression cassettes and vectors and in vitro culture methods for plant cell or tissue transformation and regeneration of plants are known and available. See, e.g., Gruber et al., "Vectors for Plant Transformation," in *Methods in Plant Molecular Biology and Biotechnology*, supra, pp. 89-119.

The isolated polynucleotides or polypeptides may be introduced into the plant by one or more techniques typically used for direct delivery into cells. Such protocols may vary depending on the type of organism, cell, plant or plant cell, i.e., monocot or dicot, targeted for gene modification. Suitable methods of transforming plant cells include microinjection (Crossway, et al., (1986) *Biotechniques* 4:320-334 and U.S. Pat. No. 6,300,543), electroporation (Riggs, et al., (1986) *Proc. Natl. Acad. Sci. USA* 83:5602-5606, direct gene transfer (Paszkowski, et al., (1984) *EMBO J.* 3:2717-2722) and ballistic particle acceleration (see, for example, Sanford, et al., U.S. Pat. No. 4,945,050; WO 91/10725 and McCabe, et al., (1988) *Biotechnology* 6:923-926). Also see, Tomes, et al., "Direct DNA Transfer into Intact Plant Cells Via Microprojectile Bombardment". pp. 197-213 in *Plant Cell, Tissue and Organ Culture, Fundamental Methods.* eds. Gamborg and Phillips. Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839 and Gordon-Kamm, et al., (1990) *Plant Cell* 2:603-618 (maize); Hooydaas-Van Slogteren and Hooykaas (1984) *Nature* (London) 311:763-764; Bytebierm, et al., (1987) *Proc. Natl. Acad. Sci. USA* 84:5345-5349 (Liliaceae); De Wet, et al., (1985) *In The Experimental Manipulation of Ovule Tissues*, ed. Chapman, et al., pp.

197-209. Longman, N.Y. (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl MicrobioL* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185), all of which are herein incorporated by reference.

*Agrobacterium*-Mediated Transformation

The most widely utilized method for introducing an expression vector into plants is based on the natural transformation system of *Agrobacterium. A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion or via a binary system where the vir gene is present on a separate vector. Such systems, vectors for use therein, and methods of transforming plant cells are described in U.S. Pat. No. 4,658,082; U.S. Patent Application Serial Number 913,914, filed Oct. 1, 1986, as referenced in U.S. Pat. No. 5,262,306, issued Nov. 16, 1993 and Simpson, et al., (1986) *Plant Mol. Biol.* 6:403-15 (also referenced in the '306 patent), all incorporated by reference in their entirety.

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra; and U.S. Patent Application Ser. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206 and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731 and Christou, et al., (1987) *Proc. Natl. Acad. Sci. USA* 84:3962. Direct uptake of DNA into protoplasts using $CaCl_2$ precipitation, polyvinyl alcohol or poly-L-ornithine has also been reported. See, e.g., Hain, et al., (1985) *Mol. Gen. Genet.* 199:161 and Draper, et al., (1982) *Plant Cell Physiol.* 23:451.

Electroporation of protoplasts and whole cells and tissues has also been described. See, e.g., Donn, et al., (1990) *Abstracts of the VIIth Int'l. Congress on Plant Cell and Tissue Culture IAPTC*, A2-38, p. 53; D'Halluin, et al., (1992) *Plant Cell* 4:1495-505 and Spencer, et al., (1994) *Plant Mol. Biol.* 24:51-61.

1. Polynucleotide-Based Methods:

In some embodiments of the present disclosure, a plant is transformed with an expression cassette that is capable of expressing a polynucleotide that inhibits the expression of OsBG1 of the disclosure. The term "expression" as used herein refers to the biosynthesis of a gene product, including the transcription and/or translation of said gene product. For example, for the purposes of the present disclosure, an expression cassette capable of expressing a polynucleotide that inhibits the expression of at least one nitrate uptake-associated polypeptide is an expression cassette capable of producing an RNA molecule that inhibits the transcription and/or translation of at least one nitrate uptake-associated polypeptide of the disclosure. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of OsBG1 are given below.

i. Sense Suppression/Cosuppression

In some embodiments of the disclosure, inhibition of the expression of OsBG1 may be obtained by sense suppression or cosuppression. For cosuppression, an expression cassette is designed to express an RNA molecule corresponding to all or part of a messenger RNA encoding OsBG1 in the "sense" orientation. Over expression of the RNA molecule can result in reduced expression of the native gene. Accordingly, multiple plant lines transformed with the cosuppression expression cassette are screened to identify those that show the greatest inhibition of nitrate uptake-associated polypeptide expression.

The polynucleotide used for cosuppression may correspond to all or part of the sequence encoding the nitrate uptake-associated polypeptide, all or part of the 5' and/or 3' untranslated region of OsBG1 transcript or all or part of both the coding sequence and the untranslated regions of a transcript encoding OsBG1. In some embodiments where the polynucleotide comprises all or part of the coding region for the nitrate uptake-associated polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763 and U.S. Pat. Nos. 5,034,323, 5,283,184 and 5,942,657, each of which is herein incorporated by reference. The efficiency of cosuppression may be increased by including a poly-dT region in the expression cassette at a position 3' to the sense sequence and 5' of the polyadenylation signal. See, U.S. Patent Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323, herein incorporated by reference.

ii. Antisense Suppression

In some embodiments of the disclosure, inhibition of the expression of the nitrate uptake-associated polypeptide may be obtained by antisense suppression. For antisense suppression, the expression cassette is designed to express an RNA molecule complementary to all or part of a messenger RNA encoding the nitrate uptake-associated polypeptide. Over expression of the antisense RNA molecule can result in reduced expression of the native gene. Accordingly, multiple plant lines transformed with the antisense suppression expression cassette are screened to identify those that show the greatest inhibition of nitrate uptake-associated polypeptide expression.

iii. Double-Stranded RNA Interference

In some embodiments of the disclosure, inhibition of the expression of OsBG1 may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743 and WO 99/49029, WO 99/53050, WO 99/61631 and WO 00/49035, each of which is herein incorporated by reference.

iv. Hairpin RNA Interference and Intron-Containing Hairpin RNA Interference

In some embodiments of the disclosure, inhibition of the expression of OsBG1 may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited and an antisense sequence that is fully or partially complementary to the sense sequence. Alternatively, the base-paired stem region may correspond to a portion of a promoter sequence controlling expression of the gene to be inhibited. Thus, the base-paired stem region of the molecule generally determines the specificity of the RNA interference. hpRNA molecules are highly efficient at inhibiting the expression of endogenous genes and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini et al., *BMC Biotechnology* 3:7, and U.S. Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295 and U.S. Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904; Mette, et al., (2000) *EMBO J* 19:5194-5201; Matzke, et al., (2001) *Curr. Opin. Genet. Devel.* 11:221-227; Scheid, et al., (2002) *Proc. Natl. Acad. Sci., USA* 99:13659-13662; Aufsaftz, et al., (2002) *Proc. Natl. Acad. Sci.* 99(4): 16499-16506; Sijen, et al., *Curr. Biol.* (2001) 11:436-440), herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the nitrate uptake-associated polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

vi. Ribozymes

In some embodiments, the polynucleotide expressed by the expression cassette of the disclosure is catalytic RNA or has ribozyme activity specific for the messenger RNA. This method is described, for example, in U.S. Pat. No. 4,987,071, herein incorporated by reference.

vii. Small Interfering RNA or Micro RNA

In some embodiments of the disclosure, inhibition of the expression of OsBG1 may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of nitrate uptake-associated expression, the 22-nucleotide sequence is selected from a nitrate uptake-associated transcript sequence and contains 22 nucleotides of said nitrate uptake-associated sequence in sense orientation and 21 nucleotides of a corresponding antisense sequence that is complementary to the sense sequence. miRNA molecules are highly efficient at inhibiting the expression of endogenous genes and the RNA interference they induce is inherited by subsequent generations of plants.

2. Polypeptide-Based Inhibition of Gene Expression

In one embodiment, the polynucleotide encodes a zinc finger protein that binds to a gene encoding OsBG1, resulting in reduced expression of the gene. In particular embodiments, the zinc finger protein binds to a regulatory region of a nitrate uptake-associated gene. In other embodiments, the zinc finger protein binds to a messenger RNA encoding OsBG1 and prevents its translation. Methods of selecting sites for targeting by zinc finger proteins have been described, for example, in U.S. Pat. No. 6,453,242 and methods for using zinc finger proteins to inhibit the expression of genes in plants are described, for example, in U.S. Patent Application Publication Number 2003/0037355, each of which is herein incorporated by reference.

3. Polypeptide-Based Inhibition of Protein Activity

In some embodiments of the disclosure, the polynucleotide encodes an antibody that binds to polypeptide of the disclosure. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present disclosure, the activity of OsBG1 is reduced or eliminated by disrupting the gene encoding the nitrate uptake-associated polypeptide. The gene encoding the nitrate uptake-associated polypeptide may be disrupted by any method known in the art. For example, in one embodiment, the gene is disrupted by transposon tagging. In another embodiment, the gene is disrupted by mutagenizing plants using random or targeted mutagenesis and selecting for plants that have reduced nitrogen utilization activity.

i. Transposon Tagging

In one embodiment of the disclosure, transposon tagging is used to reduce or eliminate the nitrate uptake-associated activity of one or more nitrate uptake-associated polypeptide. Transposon tagging comprises inserting a transposon within an endogenous nitrate uptake-associated gene to reduce or eliminate expression of the nitrate uptake-associated polypeptide. "nitrate uptake-associated gene" is intended to mean the gene that encodes OsBG1 according to the disclosure.

In this embodiment, the expression of one or more nitrate uptake-associated polypeptide is reduced or eliminated by inserting a transposon within a regulatory region or coding region of the gene encoding the nitrate uptake-associated polypeptide. A transposon that is within an exon, intron, 5' or 3' untranslated sequence, a promoter or any other regulatory sequence of a nitrate uptake-associated gene may be used to reduce or eliminate the expression and/or activity of the encoded nitrate uptake-associated polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS MicrobioL Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540 and U.S. Pat. No. 5,962,764, each of which is herein incorporated by reference.

ii. Mutant Plants with Reduced Activity

Additional methods for decreasing or eliminating the expression of endogenous genes in plants are also known in the art and can be similarly applied to the instant disclosure. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) *Virology* 243:472-481; Okubara, et al., (1994) *Genetics* 137:867-874 and Quesada, et al., (2000) *Genetics* 154:421-436, each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant disclosure. See, McCallum, et al., (2000) *Nat. Biotechnol.* 18:455-457, herein incorporated by reference.

Mutations that impact gene expression or that interfere with the function (enhanced nitrogen utilization activity) of the encoded protein are well known in the art. Insertional mutations in gene exons usually result in null-mutants. Mutations in conserved residues are particularly effective in inhibiting the activity of the encoded protein. Conserved residues of plant nitrate uptake-associated polypeptides suitable for mutagenesis with the goal to eliminate nitrate uptake-associated activity have been described. Such mutants can be isolated according to well-known procedures, and mutations in different nitrate uptake-associated loci can be stacked by genetic crossing. See, for example, Gruis, et al., (2002) *Plant Cell* 14:2863-2882.

In another embodiment of this disclosure, dominant mutants can be used to trigger RNA silencing due to gene inversion and recombination of a duplicated gene locus. See, for example, Kusaba, et al., (2003) *Plant Cell* 15:1455-1467.

The disclosure encompasses additional methods for reducing or eliminating the activity of one or more nitrate uptake-associated polypeptide. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleobases.

Such vectors and methods of use are known in the art. See, for example, U.S. Pat. Nos. 5,565,350; 5,731,181; 5,756,325; 5,760,012; 5,795,972 and 5,871,984, each of which are herein incorporated by reference. See also, WO 98/49350, WO 99/07865, WO 99/25821 and Beetham, et al., (1999) *Proc. Natl. Acad. Sci. USA* 96:8774-8778, each of which is herein incorporated by reference.

vi. Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant in which the activity or level of the nitrate uptake-associated polypeptide has not been modulated. "Modulating floral development" further includes any alteration in the timing of the development of a plant's reproductive tissue (i.e., a delayed or an accelerated timing of floral development) when compared to a control plant in which the activity or level of the nitrate uptake-associated polypeptide has not been modulated. Macroscopic alterations may include changes in size, shape, number, or location of reproductive organs, the developmental time period that these structures form or the ability to maintain or proceed through the flowering process in times of environmental stress. Microscopic alterations may include changes to the types or shapes of cells that make up the reproductive organs.

In general, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" or engineered endonucleases such as meganucleases produced to modify plant genomes (see e.g., WO 2009/114321; Gao et al. (2010) Plant Journal 1:176-187). Another site-directed engineering is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. A transcription activator-like (TAL) effector-DNA modifying enzyme (TALE or TALEN) is also used to engineer changes in plant genome. See e.g., U.S. 20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The CRISPR/Cas system allows targeted cleavage of genomic DNA guided by a customizable small noncoding RNA. Based on the disclosure of the BG1 coding sequences, polypeptide sequences of the orthologs/homologs and the genomic DNA sequences, site-directed mutagenesis can be readily performed to generate plants expressing a higher level of the endogenous BG1 polypeptide or an ortholog thereof.

Antibodies to a BG1 polypeptide disclosed herein or the embodiments or to variants or fragments thereof are also encompassed. The antibodies of the disclosure include polyclonal and monoclonal antibodies as well as fragments thereof which retain their ability to bind to BG1 polypeptide disclosed herein. An antibody, monoclonal antibody or fragment thereof is said to be capable of binding a molecule if it is capable of specifically reacting with the molecule to thereby bind the molecule to the antibody, monoclonal antibody or fragment thereof. The term "antibody" (Ab) or "monoclonal antibody" (Mab) is meant to include intact molecules as well as fragments or binding regions or domains thereof (such as, for example, Fab and F(ab).sub.2 fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, et al., Monoclonal Antibodies, Hybridoma: A New Dimension in Biological Analyses, Plenum Press, N.Y. (1980) and Campbell, "Monoclonal Antibody Technology," In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. PtIP-50 polypeptide or PtIP-65 polypeptide antibodies or antigen-binding portions thereof can be produced by a variety of techniques, including conventional monoclonal antibody methodology, for example the standard somatic cell hybridization technique of Kohler and Milstein, (1975) Nature 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing a BG1 polypeptide disclosed herein as antigens.

A kit for detecting the presence of a BG1 polypeptide disclosed herein or detecting the presence of a nucleotide sequence encoding a BG1 polypeptide disclosed herein, in a sample is provided. In one embodiment, the kit provides antibody-based reagents for detecting the presence of a BG1 polypeptide disclosed herein in a tissue sample. In another embodiment, the kit provides labeled nucleic acid probes useful for detecting the presence of one or more polynucleotides encoding BG1 polypeptide disclosed herein. The kit is provided along with appropriate reagents and controls for carrying out a detection method, as well as instructions for use of the kit.

As discussed above, one of skill will recognize the appropriate promoter to use to modulate floral development of the plant. Exemplary promoters for this embodiment include constitutive promoters, inducible promoters, shoot-preferred promoters and inflorescence-preferred promoters.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases and those involved in housekeeping, such as heat shock proteins. More specific categories of transgenes, for example, include genes encoding important traits for agronomics, insect resistance, disease resistance, herbicide resistance, sterility, grain characteristics and commercial products. Genes of interest include, generally, those involved in oil, starch, carbohydrate, or nutrient metabolism as well as those affecting kernel size, sucrose loading, and the like.

In certain embodiments the nucleic acid sequences of the present disclosure can be used in combination ("stacked") with other polynucleotide sequences of interest in order to create plants with a desired phenotype.

This disclosure can be better understood by reference to the following non-limiting examples. It will be appreciated by those skilled in the art that other embodiments of the disclosure may be practiced without departing from the spirit and the scope of the disclosure as herein disclosed and claimed.

EXAMPLES

Example 1—Bg1-D Mutant Exhibits Increased Grain Size Phenotype

To gain more insight into the genetic networks controlling grain size in rice, a number of mutants with various seed size were found in a large population of T-DNA rice mutants which were obtained by transforming rice (*Oryza sativa* L. cv. Nipponbare) by Agrobacterium-mediated transformation (Ma et al., 2009, J. Genet. Genomics, 36, 267-276). One of them, big grain1 (bg1-D), a dominant rice mutant with significantly increased grain size and grain weight was identified and characterized. Compared with wild-type Nipponbare (*Oryza Sativa* L. spp. *Japonica*), bg1-D showed increased plant stature and enlarged organ size during both the vegetative and reproductive stages (FIG. 1). In the seventh day after germination, an accelerated growth was observed in bg1-D mutant which has significantly elongated leaf sheath compared with the wild-type plants (FIG. 1A and FIG. 13). The morphological differences between wild-type and bg1-D become more apparent after they enter the state of reproductive and vegetative phase. The leaves of bg1-D were larger than those of wild-type plants and bg1-D mutant showed an altered internode elongation which resulted in increased plant height (FIGS. 1. B and C). Interestingly, bg1-D displayed longer panicle and larger grain phenotype (FIGS. 1D, E and F), which traits are closely linked with rice yield. Examination of the cross-section of rice hull before flowering revealed that an increasing number and volume of parenchyma cells appeared in the bg1-D (FIG. 2), giving rise to an increased grain width. Longitudinal sections of spikelet hull observed by scanning electron microscopy (SEM) showed the epidermis cells in bg1-D was longer than that of wild-type (FIG. 14). Further, grain filling rate by measuring fresh and dry weights was also compared. Both fresh and dry weight of bg1-D was significantly higher than those of wild-type at 15 d after fertilization, and the differences reached a maximum at about 25 d after fertilization (FIG. 15). Based on these results, it is likely that the increase in grain size and grain weight in bg1-D mutant mainly resulted from increases in grain width, length and grain filling rate. Agronomic traits were compared between mature plants between bg1-D and wild-type plants are presented Table A1.

Plant Materials and Growth Conditions:

The Bg1-D mutant was initially identified from our T-DNA insertion population in Nipponbare (ssp *japonica*) background. All mature plants were grown in a paddy field in Beijing or Hainan under natural conditions. For plant hormone treatment, germinated seeds were placed on bottomless 96-well plates floating on ½ MS and moved to growth chambers (28° C.) with 12 h light/12 h dark cycle. Seedlings were sampled and treated after 7 d.

TABLE A1

The agronomic traits of wild-type and Bg1-D plants.

| Agronomic traits | Wild-Type | bg1-D |
|---|---|---|
| Plant height (cm) | 94.3 ± 3.8 | 110.5 ± 5.3*** |
| Tiller number | 12.0 ± 2.0 | 11.0 ± 3.0 |
| Panicle length (cm) | 19.6 ± 0.9 | 23.2 ± 1.2*** |

TABLE A1-continued

The agronomic traits of wild-type and Bg1-D plants.

| Agronomic traits | Wild-Type | bg1-D |
|---|---|---|
| Grain No. per panicle | 105.9 ± 11.7 | 109.3 ± 10.8 |
| Grain length (mm) | 7.4 ± 0.2 | 8.1 ± 0.2** |
| Grain width (mm) | 3.2 ± 0.1 | 3.5 ± 0.1** |
| 1000-grain weight (g) | 21.9 ± 0.3 | 29.3 ± 0.4*** |

Agronomic traits analyses were done on mature plants. Results represent means±SD of populations of the size indicated in parentheses, (n=30). Asterisks indicate the significance of differences between wild-type and Bg1-D plants determined by Student's t test. $0.001 \leq P < 0.01$, *$P < 0.001$.

TABLE A2

Yield test in a paddy is shown below.

| Traits | NP | OE-5 (NP) | OE-7 (NP) |
|---|---|---|---|
| Pannicles per plot | 3450.3 ± 59.4 | 3223.6 ± 41.5 | 3159.5 ± 34.1 |
| Grains per panicle | 87.4 ± 4.6 | 83.7 ± 3.5 | 82.2 ± 4.3 |
| 1000-grain weight (g) | 22.3 ± 0.4 | 27.3 ± 0.6 | 29.2 ± 0.5 |
| Theoretical yield per plot (kg) | 6.7 ± 0.7 | 7.4 ± 0.5 | 7.6 ± 0.6 |
| Actual yield per plot (kg) | 5.3 ± 0.5 | 6.1 ± 0.4 | 6.4 ± 0.5 |

The planting density was 20 cm×20 cm, the area per plot was 15 m². Data were calculated from plants in block region with three replications under natural condition in Beijing, China.

Example 2—Molecular Cloning and Characterization of BG1

By genetics analysis, the phenotype of bg1-D co-segregated with the T-DNA insertion, and the segregation ratio of T1 generation is approximately 3:1, reflecting T-DNA inserted at a single locus in bg1-D mutant. In addition, the progeny of bg1-D showed big grain phenotype weather the bg1-D acted as male parent or female parent, suggesting Bg1 is a dominant mutant through activation of BG1 (Table S1).

The T-DNA 3'-flanking sequence was cloned by Site-Finding PCR method based on thermal asymmetric interlaced PCR (TAIL-PCR) using known methods. Sequence analysis revealed that a gene, Os03g0175800, is located 0.8 kb downstream of the T-DNA insertion. The expression level of Os03g0175800 increased at about 10 times more than the level in the wild-type plants (FIG. 3). The relative expression level of adjacent genes of T-DNA insertion site and no significant difference existed between wild-type and bg1-D mutant. Based on these results, it was hypothesized that Os03g0175800 is the gene responsible for the bg1-D mutant and designated this gene as BG1. The full-length cDNA for BG1 was cloned by 5' and 3' RACE kit. It is showed that the BG1 full-length cDNA is 1162 by long and contains a 933 by open reading frame (ORF) which encodes 330 amino acid. BLAST search of the protein databases reveals that BG1 has similarity to proteins from other higher plants. Phylogenetic analysis showed that BG1 and its 22 structural homologs can be classified into two subgroups: BG1 dicot-specific groups and BG1 monocot-specific groups.

In Arabidopsis, there are four BG1-like proteins displaying high sequence similarity with BG1, some residues are highly conserved in the N-terminus and C-terminus region of BG1 between rice and Arabidopsis (FIG. 16). In monocot, BG1 is closely related to Bradi1g72920 from Brachypodium, GRMZM2G007134 and GRMZM2G438606 from maize, suggesting BG1 is evolutionarily conserved across plant species. BG1 may function as a novel plant specific regulator for grain size.

The expression pattern of BG1 was examined by real-time PCR and promoter GUS assay, the result showed that BG1 was ubiquitously expressed in all tissues, including root, culm, leaf, sheath and panicles. But it was strongly expressed in the young panicles (1-5 cm length) and culm, and the expression level gradually decreased as the panicles matured. Histochemical analysis of BG1PRO:GUS transgenic plants revealed that GUS activity was preferentially detected in the vascular tissues of the tissues examined (FIG. 5).

Cloning of the BG1 Gene:

Rice genomic DNA was isolated using known techniques. The 3'-flanking region of the T-DNA insertion in Bg1-D was identified by means of SiteFinding PCR method based on thermal asymmetric interlaced PCR (TAIL-PCR). The primers used for SiteFinding PCR were listed in Table S2. Full-length cDNA of BG1 was amplified by Invitrogen 5' and 3' RACE system.

TABLE S1

Phenotypic measurements of transgenic positive and negative plants in the T1 generation of Bg1-D
Bg1(+) and Bg1(−) represent transgenic positive and negative plants in T₁ generation, respectively. Values are means ± SE.

| Genotype | Number of plants | Plant height (cm) | Grain length (mm) | Grain width (mm) | 1000-grain weight (g) |
|---|---|---|---|---|---|
| Wild-type | 20 | 94.3 ± 3.8 | 7.35 ± 0.18 | 3.23 ± 0.08 | 21.90 ± 0.3 |
| Bg1-D (T₂) | 20 | 110.5 ± 5.3 | 8.47 ± 0.25 | 3.78 ± 0.17 | 29.3 ± 0.40 |
| Bg1-D(+) | 53 | 105.1 ± 8.5 | 8.16 ± 0.51 | 3.64 ± 0.35 | 26.89 ± 0.55 |
| Bg1-D(−) | 16 | 95.2 ± 5.4 | 7.43 ± 0.15 | 3.34 ± 0.13 | 22.34 ± 0.5 |

TABLE S2

Primer used for Site-Finding PCR and RACE
(SEQ ID NOS: 28-38, in consecutive order below).

| Primer name | Sequence (5'-3') |
|---|---|
| SF1 | CACGACACGCTACTCAACACACCACCTCGC ACAGCGTCCTANNNNNNNGCATG |
| SFP1 | CACGACACGCTACTCAACAC |
| SFP2 | ACTCAACACACCACCTCGCACAGC |
| GSP1 | ACAATGCTGAGGGATTCAAATTCTACCCA |
| GSP2 | TACTGAATTAACGCCGAATTGAATTC |
| GeneRacer 5' primer | CGACTGGAGCACGAGGACACTGA |
| GeneRacer RNA Oligo | CGACUGGAGCACGAGGACACUGAC |
| Sequence | AUGGACUGAAGGAGUAGAAA |
| BG1-1R | CTTGGCCGCCGCAGCCACCGCCTCCA |
| BG1-2R | AGAACCCGCCGTAGCTAGAACACT |
| BG1-3R | GCGAAGATGGAGTTGAGGAA |

RNA Extraction and Quantitative Real-Time RT-PCR:

Total RNAs were isolated from various rice tissues using the TRIzol reagent (Invitrogen). After RNase free DNase (Promega) treatment, 2 µg RNA was reverse transcribed using oligo (dT) primer and AMV reverse transcriptase (Promega). Quantitative real-time PCR (qRT-PCR) experiments were performed by using SsoFast EvaGreen Supermix (Biorad) with Bio Rad CFX96 real-time PCR machine. The rice ACTIN1 gene (OsACT1) was used as the internal control. Gene-specific primers used in qRT-PCR are listed in Table S3.

Vector Construction and Plant Transformation

BG1 full-length coding sequences were amplified from cDNA of WT plants and cloned into pCAMBIA 2300-Actin to generate pCAMBIA 2300-Actin:BG1 overexpression constructs. A 3.6 kb genomic fragment containing a 2 kb native promoter and the entire BG1 coding region with 3' UTR were cloned into pCAMBIA 2300 vector to create pCAMBIA 2300-ProBG1:BG1 overexpression constructs. To generate BG1-RNAi construct, a 440 by gene-specific fragment (SEQ ID NO: 75) of BG1 coding sequence was amplified and cloned into pCAMBIA 2300-Actin vector by the method described previously (Lin et al., 2012, Plant Physiol. 158, 451-464). For promoter-GUS assay, a 2-kb genomic fragment upstream of the BG1 gene translation start codon was amplified and cloned into the pCAMBIA2391Z. For subcellular localization, BG1 was in-frame fused with C-terminal GFP tag driven by 35S promoter. Upon sequence confirmation, all of the resulting constructs were transformed into the rice genome by known Agrobacterium tumefaciens-mediated transformation methods. The transgenic plants were then transferred to the field for normal growth and seed harvesting. The primer sequences for vector construction are listed in Table S4.

TABLE S3

Primers used for real-time PCR (SEQ ID NOS: 39-64, in consecutive order, with the forward and reverse primers for each of the gene indicated below).

| Gene | Forward primer (5'-3') | Reverse primer (5'-3') |
| --- | --- | --- |
| BG1 | GATGGAGAGCGACGAGGAC | GCAATGGCGGCGAAGTTC |
| Ubiquitin | ACCACTTCGACCGCCACTACT | ACGCCTAAGCCTGCTGGTT |
| Actin | TGGCATCTCTCAGCACATTCC | TGCACAATGGATGGGTCAGA |
| CDKA1 | GGTTTGGACCTTCTCTCTAAAATGC | AGAGCCTGTCTAGCTGTGATCCTT |
| E2F2 | TGTTGGTGGCTGCCGATAT | CGCCAGGTGCACCCTTT |
| H1 | GCAAGGCACCTGCAGCTT | AGGCAGCCTTTGTACAGATCCT |
| CYCD1; 1 | CCGTCGCTCGCATTCGTA | TCATGTGCCTGGTGGTGA |
| CYCT1 | GCTTCTTTCAGAGGGTCAT | GCATTTCAAGTACACGAGGT |
| OsEXPA5 | AAGGCTGTGGCTTGATTGACA | TTAGGCCCAATTTTGCTATTTTG |
| OsEXPA10 | TGACCAACTACAACGTGGTCCC | GCCAGTGTATGTTTTGCCGAAG |
| OsEXPB3 | CTTTGAGTGGTTGGAGTGGTGG | GCAGCCTTCTTGGAGATGGA |

TABLE S3 -continued

Primers used for real-time PCR (SEQ ID NOS: 39-64, in consecutive order, with the forward and reverse primers for each of the gene indicated below).

| Gene | Forward primer (5'-3') | Reverse primer (5'-3') |
| --- | --- | --- |
| OsEXPB4 | GTCGGTCTGTGTTGCGATTTG | CCTCCATTTCCCACACAGCTT |
| OsEXPB7 | ACGGTGATCATCACGGACAT | TCGAAGTGGTACAGCGACACT |

TABLE S4

Primers used for vector construction.
(SEQ ID NOS: 65-74, in consecutive order, with the forward and reverse primers as indicated below)
(Labeled sequence indicates enzyme cleavage site).

| Gene | Forward primer (5'-3') | Reverse primer (5'-3') |
| --- | --- | --- |
| BG1OX | TCTAGAATGGAGAGGTGGGCGGCGCCCAAG | CTGCAGTCAGACAACTCTGGCGCTCCGT |
| BG1RNAi | CTCGAGCAGCCGTCTTTCTCATCCAC | GGATCCGCGAAGATGGAGTTGAGGAA |
| BG1GUS | GGATCCGCTTGTCATTGCTGTACATG | GAATTCAGGAAACAAACGCCAAGAAG |
| BG1EGFP | TCTAGAATGGAGAGGTGGGCGGCGCCCAAG | ACTAGTGACAACTCTGGCGCTCCGTCCAT |
| BG1DNAOX | GAATTCGCTTGTCATTGCTGTACATGCTGT | GGATCCCACACACATGTTCCCATTAGGTTT |

Histological Analysis and Microscopy Observation:

Cross-sections of spikelet hulls were analyzed by light microscopy (BX51; Olympus). Spikelet hulls were fixed with formalin:glacial acetic acid:70% ethanol (1:1:18) and then dehydrated in a graded ethanol series. Fixed tissues were embedded in Paraplast Plus chips (Sigma), and cut using a microtome into 10 µm thick sections and then affixed to poly-Lys-coated slides (Sigma), followed by dewaxed in xylene, gradely rehydrated and dried before toluidine blue staining for light microscopy. Cells number and cell area in the outer parenchyma layer of the spikelet hulls were measured by Olympus stream software. Longitudinal sections of spikelet hull were analyzed by scanning electron microscopy (S-3000N; Hitachi), The sample pretreatment was done as described previously (Li et al., 2010, Cell Res. 20, 838-849). Cell lengths were measured both in WT and in Bg1-D.

Example 3—BG1 is a Novel Positive Regulator Controlling Grain Size

To further validate BG1's function as a regulator of grain size and whether overexpression of BG1 is necessary for the increased grain size phenotype, we transformed wild-type rice with an expression vector that drives BG1 cDNA under the control of the rice ACTIN1 promoter. As show in FIG. 6, the BG1 overexpressed plants showed various degrees of grain size increasing phenotypes and of panicle elongation (FIGS. 6A, B, C). The magnitude of the change in the phenotypes was apparently correlated with the level of BG1 expression (FIG. 6D). The 1000-grain weight of BG1-overexpression lines increased dramatically, resulting from the increase of grain length and grain width in transgenic plants compared with the wild-type (FIGS. 6E, F, G). On the contrary, suppression of BG1 by RNAi led to obvious phenotypes in rice. The plant height is shorter and the length of panicle and grain size were greatly decreased (FIGS. 7A, B, C, D), which lead to 1000-grain weight reduction compared with the wild-type plants. (FIG. 7F). All these phenotype, to some extent, was consistent with the result that BG1 is strongly expressed in culm and panicles. It was concluded that BG1 is the gene responsible for the bg1-D dominant mutant. In addition, transformed wild-type Arabidopsis (Col-0) expressing OsBG1 driven by cauliflower mosaic virus (CaMV) 35S promoter showed that overexpression of OsBG1 in Arabidopsis also result in increased seed size, indicating OsBG1 may share some common regulatory mechanism between monocots and dicots (FIG. 17).

Example 4—BG1 Localized to the Plasma Membrane

To study the function of BG1 on grain size regulation, the subcellular localization of BG1 was investigated. Prediction by web-based tools described previously showed that BG1 protein contains no putative sequence motifs that define a specific subcellular localization or extracellular secretion. Then, the ORF of BG1 was fused with enhanced green fluorescent protein (BG1-eGFP) to generate pC2300-35S:BG1-eGFP vector. The transgenic plants showed the same phenotype as the bg1-D mutant, such as increased grain size and plant height, indicating that the fused BG1-eGFP did have the same function as the BG1 alone. Transgenic young seedling's root was observed and the fluorescent of BG1-eGFP is predominantly localized to the plasma membrane (FIG. 8A), consisting with our transient expression assay of BG1-eGFP in rice protoplast. To further confirm this result, the microsome of transgenic plants with BG1-eGFP was separated, it was observed that the BG-eGFP can be detected by GFP antibody in the microsomal pellet, but only very faint signal was detected in the soluble fraction. Two-phase partitioning assay further confirm BG1-GFP protein was highly enriched in the plasma membrane-enriched fractions, but not in the other membrane's fractions (FIG. 8B). All these results indicated the BG1 is a novel protein which predominantly localized to the plasma membrane.

Subcellular Localization of BG1:

The BG1 cDNA sequence was cloned in frame with the eGFP protein under the control the 35S promoter. For confocal microscopy, the localization patterns of BG1:eGFP was examined by imaging root tips of 7-day-old seedlings of BG1:eGFP transgenic lines and rice protoplast using a confocal laser scanning microscope (Leica TCS SP5). eGFP were excited at 488 nm wavelengths, and the emission filters were 500-530 nm. Preparation and efficiency transfection of rice protoplasts were performed according to the method described previously with minor modifications (Zhang et al., 2011, Plant Methods 7.21). Microsomal fractionations and two-phase membrane partitioning experiments were conducted as previously described protocol. Equal amount of proteins of the total microsomal and the PM-enriched upper phase were analyzed by SDS-PAGE and immunoblotting with anti-GFP (Roche), anti-PIP2 (Agrisera), anti-PEPC (Agrisera) and anti-LHCII (Agrisera) antibody Example 5—BG1 is a Primary Auxin Response Gene Phytohormones play a very vital role in the growth and development of plants. To determine whether BG1 can response to exogenous plant hormone, the relative mRNA level of BG1 was investigated by real-time-PCR under different treatment. The result showed that BG1 can by specifically induced by IAA after 2-hour application, but not by other phytohormones (FIG. 9A). Time-course IAA induction in wild-type plants revealed BG1 mRNA level rapidly increased within 30 mins of IAA application and the maximal level is approximately 8-fold greater than the level seen in uninduced plants at 4-hour later, then the expression declined and gradually to the primitive level (FIG. 9B). The induction of BG1 mRNA by IAA occurs in the presence of the protein synthesis inhibitor cycloheximide (CHX), suggesting the accumulation of BG1 transcripts was independent of protein synthesis (FIG. 9C). Moreover, another two auxin compounds, naphthylacetic acid (NAA) and 2,4-dichlorophenoxyacetic acid (2-4-D) can also induce the expression of BG1. However, tryptophan, a molecule that is structurally similar to IAA but without auxin activity, fails to induce BG1 mRNA accumulation (FIG. 9D). These results are consistent with that two auxin responsive element (TGTCTC) were found within 1500 by upstream of the BG1 translational start site. Based on these results, it was predicted that BG1 is novel a primary auxin-response gene. To test the sensitivity of exogenous IAA, leaf sheath of 7-day-old seedlings of WT and Bg1-D were treated with 10-3 μM IAA, Bg1-D mutant showed elongated leaf sheath compared with that of wild-type plants, suggesting the activation of BG1 led to increased IAA sensitivity (FIG. 9E).

Example 6—Bg1-D Mutant Exhibit Altered IAA Distribution and Transport

To further elucidate the mechanisms responsible for the phenotypes conferred by the BG1 overexpression, the effects of the increased BG1 activity on auxin transport was observed. When DR5-GUS plants were crossed to Bg1-D, the expression pattern of GUS was altered in the double mutant. GUS expression was mainly accumulated at the root apex area in wild-type plants. However, in DR5-GUS/Bg1-D double mutant, the GUS expression was more intense and covered a broader area in the root elongation zone (FIG. 10B). Furthermore, when the basipetal IAA was measured directly, it was found that that approximately a 50% increase in basipetal IAA transport was observed in the coleoptile of Bg1-D dark-grown seedlings, indicating that the enhanced basipetal PAT resulted in altered endogenous IAA distribution in the Bg1-D mutant plant (FIG. 10A). Consistently, Bg1-D exhibited enhanced resistance to NPA, an exogenous IAA transport inhibitor, revealing that BG1 can specifically response to IAA coupling with enhanced polar auxin transport (FIG. 18).

Auxin Transport Assay:

The polar auxin transport assays were performed using 5-day-old coleoptiles of dark-grown rice seedlings as described previously with minor modifications (Li et al., 2007, Cell Res. 17, 402-410; Qi et al., 2008, Plant Physiol. 147, 1947-1959), 2.0 cm length apical coleoptile segments (0.2 cm away from the tip was cutted off) were preincubated in ½ MS medium with shaking at 50 rpm for 2 h. The apical ends of coleoptile segment were then submerged in 15 μL of ½ MS liquid medium containing 0.2% phytogel, 500 nM 3H-IAA and 500 nM free IAA in a 1.5 mL microcentrifuge tube in the dark at room temperature for 3 h. NPA and 3H-BA were added as the IAA transport control. After 3 h transport assay, 0.5 cm from the unsubmerged ends of the segments were excised and washed three times in ½ MS liquid medium. The segments were then grouped in sets of five and incubated in 2.0 mL of universal scintillation fluid for 18 h. The radioactivity was counted with a liquid scintillation counter (1450 MicroBeta Trix; Perkin-Elmer). Based on the orientation of the coleoptile segments submerged in the buffer, acropetal auxin transport was also measured as a negative control.

Example 7: Organ Size-Associated Genes was Upregulated in Bg1-D Mutant

Several genes have been characterized in controlling organ size in Arabidopsis, especially the genes responsible for cell proliferation and cell expansion, such as AINEGUMENTA (ANT), AtEXP10, ARGOS, CycD3;1, AtGIF1 and AtGRF1. To investigate the relationship of BG1 with the genes regulating the plant cell proliferation and cell expansion in rice, the transcript levels of core cell cycle and cell expansion regulators were analyzed by using quantitative RT-PCR in both mutant and wild-type plants. Genes regulating G1 to S1 phase of cell cycle and cell expansion genes were upregulated significantly in the young panicles of Bg1-D compared to the wild-type plants (FIG. 11). These results indicated that BG1 may play a new positive regulatory role in the control of cell proliferation and cell expansion by regulating auxin signal transduction or transport.

Example 8—Increased Expression of BG1 Increases Biomass and Grain Yield

Since activation of BG1 in bg1-D leads to increased grain size and grain weight, it was tested whether biomass and grain yield could be improved by BG1 overexpression. When grown in paddy fields, transgenic rice plants overexpressing BG1 showed a significant increase in dry weight of mature organs. In contrast, two independent BG1-RNAi transgenic plant (Ri1 and Ri2) showed decreased biomass (FIG. 19). To avoid the ectopic over-expression of BG1, we overexpressed BG1 in wild-type plants using BG1 genomic DNA driven by its native promoter. Compared to the non-transgenic control plants, the transgenic rice overexpressing BG1 showed increased grain size and larger panicle without other significant penalty trait (FIGS. 12A, B and C). The 1000-grain weight of transgenic lines OE-5, OE-7 increased 15.48% and 25.38%, and the grain yield per plant increased 6.69%, and 16.65% respectively. (FIGS. 12D and E). Yield tests revealed plants with increased BG1 expression have about 15% to 20% increase in grain yield compared with that of Nipponbare (Table A2). Taken together, these results demonstrated that BG1 overexpression in rice is positively correlated with an increase in biomass and grain yield.

Protein Sequence and Phylogenetic Analysis:

BG1 sequence of rice and Arabidopsis were obtained from the Rice Annotation Project Database (http://rapdb.dna.affrc.go.jp/) and the Arabidopsis Information Resource (http://www.arabidopsis.org/index.jsp), respectively. Protein sequences were aligned using ClustalX 1.83, and the conserved residues were displayed by GeneDoc (http://www.nrbsc.org/gfx/genedoc/). For phylogenetic analysis of BG1 homologues in plants, a total of 23 unique protein sequences were obtained through National Center for Biotechnology Information (NCBI) BLAST search and aligned using a ClustalW program. Phylogenetic tree was constructed using MEGA 4.0 based on the neighbor-joining method. Topological robustness was assessed by bootrap analysis with 500 replicates.

TABLE 2

Global Identity
Gap creation penalty: 8 and Gap extension penalty: 2

| SEQ ID NO | 17 | 12 | 14 | 13 | 27 | 22 | 23 | 24 | 19 | 18 | 11 | 21 | 20 | 15 | 16 | 25 | 26 |
|---|---|---|---|---|---|---|---|---|---|---|---|---|---|---|---|---|---|
| 1 | 70 | 62 | 72 | 62 | 29 | 32 | 31 | 32 | 29 | 22 | 51 | 35 | 32 | 47 | 46 | 72 | 50 |
| 17 | — | 55 | 65 | 55 | 28 | 32 | 31 | 33 | 28 | 18 | 44 | 33 | 32 | 44 | 42 | 68 | 46 |
| 12 | — | — | 70 | 99 | 26 | 29 | 28 | 28 | 28 | 21 | 43 | 31 | 29 | 39 | 55 | 66 | 43 |
| 14 | — | — | — | 70 | 29 | 30 | 32 | 31 | 28 | 18 | 46 | 32 | 31 | 44 | 53 | 77 | 48 |
| 13 | — | — | — | — | 27 | 30 | 28 | 29 | 28 | 19 | 43 | 30 | 29 | 38 | 54 | 66 | 43 |
| 27 | — | — | — | — | — | 34 | 38 | 39 | 36 | 19 | 23 | 41 | 43 | 24 | 19 | 27 | 23 |
| 22 | — | — | — | — | — | — | 38 | 38 | 50 | 26 | 25 | 40 | 36 | 25 | 18 | 31 | 24 |
| 23 | — | — | — | — | — | — | — | 94 | 42 | 21 | 21 | 54 | 53 | 25 | 18 | 33 | 27 |
| 24 | — | — | — | — | — | — | — | — | 42 | 20 | 21 | 55 | 55 | 25 | 17 | 32 | 26 |
| 19 | — | — | — | — | — | — | — | — | — | 23 | 23 | 43 | 42 | 23 | 14 | 29 | 24 |
| 18 | — | — | — | — | — | — | — | — | — | — | 21 | 23 | 21 | 19 | 10 | 18 | 21 |
| 11 | — | — | — | — | — | — | — | — | — | — | — | 27 | 21 | 60 | 32 | 48 | 64 |
| 21 | — | — | — | — | — | — | — | — | — | — | — | — | 73 | 26 | 21 | 34 | 29 |
| 20 | — | — | — | — | — | — | — | — | — | — | — | — | — | 21 | 19 | 31 | 27 |
| 15 | — | — | — | — | — | — | — | — | — | — | — | — | — | — | 30 | 48 | 79 |
| 16 | — | — | — | — | — | — | — | — | — | — | — | — | — | — | — | 50 | 37 |
| 25 | — | — | — | — | — | — | — | — | — | — | — | — | — | — | — | — | 49 |
| 26 | — | — | — | — | — | — | — | — | — | — | — | — | — | — | — | — | — |

TABLE 3

Global Similarity

| SEQ ID NO | 17 | 12 | 14 | 13 | 27 | 22 | 23 | 24 | 19 | 18 | 11 | 21 | 20 | 15 | 16 | 25 | 26 |
|---|---|---|---|---|---|---|---|---|---|---|---|---|---|---|---|---|---|
| 1 | 76 | 69 | 77 | 69 | 37 | 48 | 43 | 45 | 43 | 34 | 58 | 47 | 43 | 56 | 50 | 77 | 58 |
| 17 | — | 63 | 71 | 63 | 37 | 46 | 43 | 43 | 39 | 31 | 54 | 46 | 43 | 50 | 47 | 73 | 52 |

TABLE 3-continued

Global Similarity

| SEQ ID NO | 17 | 12 | 14 | 13 | 27 | 22 | 23 | 24 | 19 | 18 | 11 | 21 | 20 | 15 | 16 | 25 | 26 |
|---|---|---|---|---|---|---|---|---|---|---|---|---|---|---|---|---|---|
| 12 | — | — | 76 | 99 | 35 | 45 | 43 | 42 | 39 | 37 | 53 | 43 | 39 | 47 | 59 | 73 | 52 |
| 14 | — | — | — | 76 | 38 | 45 | 45 | 46 | 42 | 31 | 53 | 47 | 42 | 51 | 56 | 80 | 54 |
| 13 | — | — | — | — | 35 | 45 | 42 | 42 | 39 | 34 | 53 | 42 | 39 | 46 | 59 | 73 | 52 |
| 27 | — | — | — | — | — | 44 | 45 | 46 | 43 | 26 | 34 | 48 | 47 | 33 | 27 | 36 | 31 |
| 22 | — | — | — | — | — | — | 48 | 49 | 62 | 39 | 42 | 55 | 50 | 40 | 27 | 47 | 40 |
| 23 | — | — | — | — | — | — | — | 96 | 55 | 30 | 34 | 64 | 65 | 35 | 27 | 44 | 36 |
| 24 | — | — | — | — | — | — | — | — | 55 | 29 | 34 | 65 | 67 | 36 | 26 | 45 | 37 |
| 19 | — | — | — | — | — | — | — | — | — | 39 | 34 | 59 | 56 | 34 | 23 | 43 | 35 |
| 18 | — | — | — | — | — | — | — | — | — | — | 31 | 31 | 32 | 32 | 17 | 31 | 30 |
| 11 | — | — | — | — | — | — | — | — | — | — | — | 39 | 31 | 67 | 39 | 57 | 71 |
| 21 | — | — | — | — | — | — | — | — | — | — | — | — | 78 | 39 | 30 | 48 | 41 |
| 20 | — | — | — | — | — | — | — | — | — | — | — | — | — | 32 | 26 | 41 | 31 |
| 15 | — | — | — | — | — | — | — | — | — | — | — | — | — | — | 37 | 54 | 83 |
| 16 | — | — | — | — | — | — | — | — | — | — | — | — | — | — | — | 53 | 39 |
| 25 | — | — | — | — | — | — | — | — | — | — | — | — | — | — | — | — | 55 |
| 26 | — | — | — | — | — | — | — | — | — | — | — | — | — | — | — | — | — |

The disclosure has been described with reference to various specific and preferred embodiments and techniques. However, it should be understood that many variations and modifications may be made while remaining within the spirit and scope of the disclosure.

---

What is claimed is:

1. A method of improving an agronomic characteristic of a plant, the method comprising:
   (i) transforming plants with a recombinant DNA construct comprising a polynucleotide operably linked to a heterologous promoter, wherein the polynucleotide comprises a nucleic acid sequence:
      (A) a nucleic sequence encoding a polypeptide having an amino acid sequence which has at least 95% amino acid sequence identity to the amino acid sequence as set forth in SEQ ID NO: 1, or
      (B) a nucleic acid sequence which hybridizes to the full length complementary sequence of SEQ ID NO: 2 under high stringency conditions of hybridization, wherein said hybridizing nucleic acid sequence encodes a polypeptide which has the activity of SEQ ID NO: 2, and wherein said high stringency conditions of hybridization comprise hybridization at 65° C. in 0.2×SSC and washing at 65-68° C. in a buffer of 0.2×SSC, 0.1% SDS for 15 minutes after hybridization is complete; and
   (ii) selecting a transformed plant from the transformed plants of step (i) which over-expresses said polypeptide and exhibits improvement in at least one agronomic characteristic: increase in grain size, increase in grain weight, increase in panicle length, increase in grain yield, increase in grain filling rate and/or increase in biomass as compared to a wild-type untransformed plant of the same species lacking said recombinant DNA construct.

2. The method of claim 1, wherein said polynucleotide comprises a nucleic sequence encoding a polypeptide having at least 95% amino acid sequence identity to the amino acid sequence as set forth in SEQ ID NO: 1.

3. The method of claim 1, wherein said polynucleotide comprises a nucleic sequence encoding the polypeptide having the amino acid sequence as set forth in SEQ ID NO: 1.

4. The method of claim 1, wherein said heterologous promoter comprises the regulatory elements as set forth in SEQ ID NO: 3.

5. The method of claim 1, wherein said increase in plant biomass is during vegetative and/or reproductive stages of the selected transformed plant development.

6. The method of claim 1, wherein the selected transformed plant is a monocot.

7. The method of claim 1, wherein the selected transformed plant is rice or maize.

8. The method of claim 1, wherein the selected transformed plant is a dicot.

9. The method of claim 1, wherein the selected transformed plant is soybean.

* * * * *

SEQUENCE LISTING

<160> NUMBER OF SEQ ID NOS: 75

<210> SEQ ID NO 1
<211> LENGTH: 310
<212> TYPE: PRT
<213> ORGANISM: Oryza sativa

<400> SEQUENCE: 1

```
Met Glu Arg Trp Ala Ala Pro Lys Val Thr Ala Gly Ser Ala Arg Arg
1               5                   10                  15

Tyr Val Ala Asp Gln Pro Ser Phe Ser Ser Thr Leu Leu Asp Ala Ile
            20                  25                  30

Tyr Lys Ser Met Asp Glu Gln Pro Gly His Gly Gly Ala Thr Gly
        35                  40                  45

Val Glu Ala Val Ala Ala Ala Lys Lys Gln His Glu Ala Ala Leu
    50                  55                  60

His Tyr Gly Asn Tyr Tyr Lys Pro Ser Leu Ala Gly Ser Tyr Arg Ala
65                  70                  75                  80

Arg Ala Pro Gly Pro His Ala Thr Thr Ser Ser Ser Ser Glu Cys Ser
                85                  90                  95

Ser Tyr Gly Gly Phe Ser Ser Ser Glu Ala Glu Ser Ser His His Arg
            100                 105                 110

Arg Leu Arg Pro Ile Arg Thr Thr Val Pro Gly Gly Ala Pro Gly Pro
        115                 120                 125

Ala Pro Glu Lys Lys Ala Lys Lys Pro Gly Ala Ser Ile Arg Ala Lys
    130                 135                 140

Leu Arg Asp Leu Arg Lys Pro Ala Ser Pro Gly Ala Arg Leu Ala Gly
145                 150                 155                 160

Phe Leu Asn Ser Ile Phe Ala Gly Lys Arg Ala Pro Ala Thr Pro Pro
                165                 170                 175

Ser Ala Thr Ala Gly Ala Glu Ser Ala Cys Ser Thr Ala Ser Ser Tyr
            180                 185                 190
```

```
Ser Arg Ser Cys Leu Ser Lys Thr Pro Ser Thr Arg Gly Gln Ala Lys
        195                 200                 205

Arg Thr Val Arg Phe Leu Asp Ser Asp Thr Glu Ser Leu Ala Ser Ser
    210                 215                 220

Thr Val Val Asp Arg Arg Val Pro Val Glu Ala Val Gln Gln Met
225                 230                 235                 240

Leu Leu Gln Arg Met Glu Met Glu Ser Asp Glu Asp Asp Glu Ser
                245                 250                 255

Ser Asp Ala Ser Ser Asp Leu Phe Glu Leu Glu Asn Phe Ala Ala Ile
            260                 265                 270

Ala Pro Ala Gly Ala Ala Tyr Arg Asp Glu Leu Pro Val Tyr Glu Thr
                275                 280                 285

Thr Arg Val Ala Leu Asn Arg Ala Ile Gly His Gly Tyr Gly His Gly
        290                 295                 300

Arg Ser Ala Arg Val Val
305                 310
```

<210> SEQ ID NO 2
<211> LENGTH: 933
<212> TYPE: DNA
<213> ORGANISM: Oryza sativa

<400> SEQUENCE: 2

```
atggagaggt gggcggcgcc caaggtgacg gctggttcgg cgaggcggta cgtcgccgac      60
cagccgtctt tctcatccac gctgctcgac gcgatataca agtcgatgga cgagcagccg     120
ggtcacggcg gcggcgccac cggggtggag gcggtggctg cggcggccaa gaagcagcac     180
gaggcggccc tgcactatgg gaactactac aagccgtcgc tcgcggggag ctaccgggcg     240
cgcgcgccgg gtccgcacgc cacgacgtcg agctcgtcgg agtgttctag ctacggcggg     300
ttctcgtcgt ccgaggcgga gtcgtcgcac accgacgcc tccgcccat ccgcacgact      360
gtccccggtg gtgcgccggg gcccgcgccg gagaagaagg ccaagaagcc cggggcctcc     420
atacgcgcca agctcaggga cctccgcaag ccggcttccc ccggcgcgcg cctcgcgggc     480
ttcctcaact ccatcttcgc cggcaagcgc gcgccggcca cgccgccctc ggcgacggcc     540
ggggcggagt ccgcgtgctc gacggcgtcg tcctactccc gctcctgcct gagcaagacg     600
ccgtcgacgc gcgggcaggc gaagcggacc gtgcggttct ggacagcga cacggagtcc     660
ctggcgtcgt cgacggtggt cgaccgccgc agggtgcccg tggaggcggt gcagcagatg     720
ctgctccagc ggatggagat ggagagcgac gaggacgacg acgagagcag cgacgcgagc     780
tccgacctgt tcgagctcga gaacttcgcc gccattgctc ccgccggggc cgcgtaccgg     840
gacgagctgc cggtgtacga gacgaccaga gtggcgctga accgcgccat tggccatggg     900
tatggccatg gacggagcgc cagagttgtc tga                                   933
```

<210> SEQ ID NO 3
<211> LENGTH: 2031
<212> TYPE: DNA
<213> ORGANISM: Oryza sativa

<400> SEQUENCE: 3

```
gcttgtcatt gctgtacatg ctgtgctgcc gccgcgctag gagcccgggc gccctgtgcc      60
tgaaaaggac ggcggctgtg ccgcggaggc agcctcgccg tctggtctat tctcgtcgct     120
gtccccggcg accggtggcc atgctcatat tgtcatattg gcacaggtat aagcgtgccc     180
```

```
gcactgtgag atatagtcag atggcccaag tcgacgcttg gaaaaaattc cgcactttt     240
tttttgacaa actagagtag tgtctcggtc ttacaatatc gttacggcgg cggcgttgtc     300
gtgcgtgcgt gcgtgcttcg atccaccgta gcacacacgc acgctgccat cgcactcaac     360
ccccgcgtga acgtgttaat tttgtttcag ggccggggttg ctatcgccga tgcggctgtg    420
cccgctaatc acgcgacaag tgagtcgtgc gtccaaatta acagtacgta accccacacg     480
aaacacacca acaaaaactg gcaatcgatc actaaatttg aaaacaacac acatgtagat     540
gaacagcgag aacatgccag aaaacattct cccggtgacg tgcaatcaaa atcccttccg    600
ttgatctagc taggcgcccg cctaggcggc cacacgctat gaactggtta aatgggagag     660
gaagtaatag tgacaagctg gcgagatagg ataacagtat aacacagctc agctcagtgt     720
gcgttatact acggggggcca gcaatgcgtg tcctaccaag cacaaagata tgtataatcc     780
gtggtaaaga ttaaaattga ttataggaag tatgggaatc tcatgctttg cagcttgcat     840
gcactccctt ttaattagtt gtgagcgagt acgtacggtg cagtgcattt ggaggcgatt     900
agattaagca gatagataca tatatatgca gtgcagtact agcagcaact agtattagca     960
agcaagcagc ttttcgcagc gaaacgccgc accggcttgg ctgcggcccc tgcaggcggc    1020
tacattctcc cactgtttat gtttgtttct cttcattacc agtagtagca actagcaatg    1080
gagattagtg ttttcttttc ccgttttttta tttggtcgat ggagcacgaa gtggctcgag    1140
atcggctcac tgcaccgttc gccacgtcca tccgttttct gtgccatagg caggcccata    1200
gcagcaggtc ggtgtctgtg atcagagcg tgaactccc gtcaccgtca ctgctgcaaa     1260
acgacgcaat acggtgtgtg tatgcagaat gaagcccaaa atggtacgaa acgaaacgga    1320
atactcgcac tagattactg cgctataatt agcactagta ctactactcc cagaagttat    1380
tgccgctgct gcaatgcatg cgtgctcacg ttttgggtgg gtgagggaca gaggcagagg    1440
cgacagtact acatgcgtct cgatcgccag agttaaatct tgcgacgtcg tactctacag    1500
ggggagcagc agcagcgcgc ggtagtatag ttgcgtttgc gtaccccttcg atctttgatg    1560
ggcggaatag aggaacgtct gaaccatcgt aatgtatggt ataggacgac acattcccat    1620
tcacctcggt ctgaaaaaaa aaagaagctg aaattcactc aggtatatgg actgattagc    1680
agaggtcgtg gcagtgtcaa ttgtgaagaa atgataagtt caccggcggt gaggggacga    1740
gaaataagga gagacaggga gagagacggg atggccccat gacccccatc accgtcaccc    1800
gcacgcccaa accgaattag ccgggcgcca caccccgtt tccaccaccc aagcttcccc    1860
ttccaccgct atatcttccg cccgatccct tccctctca cccttctctc ctccacctttt   1920
ccccaacacg taccaccaac tcaccgcgta ccaagccacc ggctcagcag cagcagctgc    1980
catttcacag aggcattggt tgctgctctc tcttcttggc gtttgtttcc t             2031
```

<210> SEQ ID NO 4
<211> LENGTH: 366
<212> TYPE: PRT
<213> ORGANISM: Arabidopsis thaliana

<400> SEQUENCE: 4

Met Asp Pro Trp Asp Thr Tyr Asn Ile Pro Leu Asp His Gln His Arg
1               5                   10                  15

Leu Arg Asn Arg Arg Asp His Arg His Pro Ser Phe Ser Ser Thr Leu
            20                  25                  30

Leu Asp Gln Ile Tyr Arg Ser Ile Asp Asp Ser Ser Thr Asn Ser Ser
        35                  40                  45

-continued

```
Ser Met Arg Lys Thr Lys His Gln Asn Arg Glu Asp Thr Arg Val Ser
    50                  55                  60

Ala Asn Arg Arg Asp Asp Phe Asn Arg Ser Lys Asn Leu Lys Thr Ile
 65                  70                  75                  80

Glu Pro Val Phe Phe Lys His Ser Ser Ser Ser Ser Asp Ser Ser
                 85                  90                  95

Gly Phe Ser Ser Ser Glu Ser Asp Tyr Phe Tyr Arg Arg Ser Lys Ser
                100                 105                 110

Ser Pro Ala Ile Ser His Pro Lys Pro Ile Arg Thr Thr Val Glu Arg
            115                 120                 125

Phe Glu Arg Ser Pro Gln Asn His Arg Pro Asn Ser Ser Asn Lys Gln
130                 135                 140

Glu His Gly Ser Phe Leu Lys Thr Lys Ser Lys Ala Leu Lys Ile Tyr
145                 150                 155                 160

Ser Asp Leu Lys Lys Val Lys Gln Pro Ile Ser Pro Gly Gly Arg Leu
                165                 170                 175

Ala Thr Phe Leu Asn Ser Ile Phe Thr Gly Ala Gly Asn Thr Lys Lys
            180                 185                 190

Leu Asn Lys Ile Asn Thr Thr Val Thr Ser Thr Ala Ala Ala Ala
    195                 200                 205

Ala Ala Ser Ser Thr Thr Thr Cys Ser Ser Ala Ser Ser Phe Ser Arg
210                 215                 220

Ser Cys Leu Ser Lys Thr Pro Ser Ser Ser Glu Lys Ser Lys Arg Ser
225                 230                 235                 240

Val Arg Phe Cys Pro Val Asn Val Ile Phe Asp Glu Asp Ser Ser Lys
                245                 250                 255

Tyr Asn Asn Lys Asn Asn Lys Val Tyr Gly Asn Asn Glu Arg Glu Tyr
            260                 265                 270

Glu Ser Ile Arg His Thr Leu Glu Asn Arg Val Met Glu Glu Asn Arg
    275                 280                 285

Arg Val Ile Glu Ala Ala Lys Glu Leu Leu Arg Ser Tyr Gln Lys Lys
        290                 295                 300

Asn Lys Glu Val Ile Glu Val Ser Val Glu Asp Asp Glu Glu Asp
305                 310                 315                 320

Asp Asp Asp Ala Leu Ser Cys Thr Ser Ser Asp Leu Phe Glu Leu Asp
                325                 330                 335

Asn Leu Ser Ala Ile Gly Ile Asp Arg Tyr Arg Glu Glu Leu Pro Val
            340                 345                 350

Tyr Glu Thr Thr Arg Leu Asn Thr Asn Arg Ile Ile Ser Arg
        355                 360                 365

<210> SEQ ID NO 5
<211> LENGTH: 357
<212> TYPE: PRT
<213> ORGANISM: Arabidopsis thaliana

<400> SEQUENCE: 5

Met Glu Ile Thr Trp Glu Lys Pro Lys Ser Ser His His Arg Asn
  1               5                  10                  15

Pro Ser Phe Ser Ser Thr Leu Leu Asp Gln Ile Tyr Arg Ser Ile Asp
                 20                  25                  30

Asp Ser Ser Pro Pro Pro Leu Glu Ser Ile Lys Lys Lys His
            35                  40                  45

His His Gln Gln Arg Asn Ala Ser Leu His Glu Asp Arg Glu Ile Ser
    50                  55                  60
```

```
Pro Ile Tyr His Arg Arg Ser Ile Ala Ala Asp Phe Glu Arg Ser Arg
 65                  70                  75                  80

Arg Lys Thr Asp Phe Leu Arg His Ser Asn Ser Ser Ser Ser Asp Ser
                 85                  90                  95

Ser Gly Phe Ser Ser Ser Glu Ser Asp Ser His Gly Arg Ser Lys
            100                 105                 110

Ser Ser Ala Ser Pro Pro Ser Ser Arg Gln Gln Pro Lys Pro Ile
        115                 120                 125

Arg Thr Ser Ser Val Asp His Ser Ser Ala Val Gln Lys Pro Lys Glu
        130                 135                 140

Leu Gly Gly Phe Leu Arg Thr Lys Ser Lys Ala Leu Lys Ile Tyr Ser
145                 150                 155                 160

Asp Leu Lys Lys Val Lys Gln Pro Ile Ser Pro Gly Gly Arg Leu Ala
                165                 170                 175

Thr Phe Leu Asn Ser Leu Phe Thr Asn Ala Ala Thr Asn Pro Lys Lys
                180                 185                 190

His Lys Lys Thr Thr Thr Val Ala Val Val Glu Glu Pro His Ser Ser
            195                 200                 205

Ser Thr Cys Ser Ser Ala Ser Ser Phe Ser Arg Ser Cys Leu Ser Lys
        210                 215                 220

Thr Pro Ser Ser Ser Gly Lys Ser Lys Arg Ser Val Arg Phe Cys Pro
225                 230                 235                 240

Val Asn Val Ile Leu Asp Glu Asp Ser Ser Phe Thr Met Pro Tyr Ala
                245                 250                 255

Tyr Asn Asn Glu Arg Leu Tyr Asp Asn Asn Glu Ala Lys Arg Val Glu
            260                 265                 270

Glu His Arg Arg Val Ile Gln Ala Ala Lys Asp Leu Leu Arg Thr Tyr
        275                 280                 285

His Asn Lys Asn Lys Val Thr Thr Thr Asn Ile Asn Asn Val Glu Glu
        290                 295                 300

Asp Asp Glu Asp Asp Ala Ala Ser Cys Ala Ser Ser Asp Leu Phe Glu
305                 310                 315                 320

Leu Glu Asn Leu Ser Ala Ile Gly Ile Glu Arg Tyr Arg Glu Glu Leu
                325                 330                 335

Pro Val Tyr Glu Thr Thr Arg Leu Asp Asn Met Asn Arg Val Ile Ala
            340                 345                 350

Thr Gly Leu Ile Val
        355

<210> SEQ ID NO 6
<211> LENGTH: 362
<212> TYPE: PRT
<213> ORGANISM: Arabidopsis thaliana

<400> SEQUENCE: 6

Met His Lys Ser Lys Arg Asn Pro Ser Phe Ser Ser Thr Leu Leu Asp
  1               5                  10                  15

Glu Ile Tyr Asn Ser Ile Asp Pro Lys Thr Gln Lys Thr Gln Pro Tyr
                 20                  25                  30

Val Gly Ser Val Asn Thr Thr Lys Lys Gln Ser Ile Val Thr Arg
             35                  40                  45

Ser Val Pro Asp Arg Lys Ile His Arg Asp Arg Phe Phe Gly Ser Val
         50                  55                  60

Ser Ser Ser Ser Asp Ser Asn Ser Ser Ile Phe Ser Ser Ser Asp Thr
```

```
                65                  70                  75                  80
        Glu Leu Thr His Gly Lys Lys Thr Thr Ser Ser Arg Pro Leu Cys Phe
                            85                  90                  95

Gly Pro Ser Lys Thr Lys Pro Arg Lys Thr Glu Asp Lys Thr Leu Phe
                        100                 105                 110

His Gln Asn Arg Ala Thr Arg Val Tyr Asp Asp Tyr Asp Tyr Ala Ser
                        115                 120                 125

Asp Val Pro Lys Phe Asn Arg His Asp Glu Asn Trp Glu Asn Thr Arg
                    130                 135                 140

Asn Arg Arg Ser Val Lys Ser Ser Gly Asn Gln Lys Lys Pro Lys Thr
        145                 150                 155                 160

Pro Ala Ser Pro Gly Gly Arg Ile Val Asn Phe Leu Asn Ser Leu Phe
                        165                 170                 175

Ser Asn Asn Ser Lys Gln Ser Asn Ala Val Lys Ser Tyr Pro Arg Lys
                        180                 185                 190

Thr Ser Tyr Asp Asp Ser Ala Tyr Val Arg Lys Thr Ser Asn Asp Tyr
                        195                 200                 205

His Ser Ser Thr Thr Thr Cys Ser Ser Ala Ser Ser Phe Ser Arg Ser
                    210                 215                 220

Cys Met Asn Lys Gly Tyr Glu Lys Ser Ser Gly Arg Ile Lys Arg Ser
        225                 230                 235                 240

Val Arg Phe Ser Pro Val Asn Val Ile Val Pro Glu Ser Phe Thr Ser
                        245                 250                 255

Lys Glu Glu Asp Tyr Phe Ser Asn Gly Asn Ala Arg Lys Ser Val Lys
                        260                 265                 270

Lys Asn Val Glu Asp Gly Gly Arg Arg Ser Val Glu Glu Ile Ala Arg
                    275                 280                 285

Glu Phe Leu Arg Asp Tyr His Lys Asn His Glu Asn Ser Leu Val Lys
                    290                 295                 300

Thr Asn Gly Phe Glu Asp Tyr Glu Asp Asp Glu Asp Asp Asp Asp Asp
        305                 310                 315                 320

Asp Asp Val Ala Ser Asp Ser Ser Asp Leu Phe Glu Leu Asp Leu
                        325                 330                 335

Val Gly Asn His His His Asn Val Tyr Gly Asp Glu Leu Pro Val
                    340                 345                 350

Tyr Glu Thr Thr Phe Ala Gly Leu Ile Leu
                    355                 360

<210> SEQ ID NO 7
<211> LENGTH: 341
<212> TYPE: PRT
<213> ORGANISM: Arabidopsis thaliana

<400> SEQUENCE: 7

Met Ala Phe Pro Gln Arg Lys Arg Thr Pro Ser Phe Ser Ser Ser Val
1               5                   10                  15

Leu Asp Ser Val Tyr Arg Ser Ile Glu Ser Asp Gly Leu Gln Ser
                20                  25                  30

Asp Leu Lys Gly Ser Ile Asn Glu Asn Val Ser Ser Ser Ser Ser
            35                  40                  45

Pro Ser Pro Asn Lys Lys Asp Asp Lys Leu Thr Thr Leu Arg Arg Ala
        50                  55                  60

Ile Met Asp Glu Glu His Trp Leu Tyr Ala Arg Ser Ser Thr Thr Thr
65                  70                  75                  80
```

-continued

```
Thr Asn Ser Ser Asp Ser Ser Phe Ser Ser Glu Ala Glu Ser
                85                  90                  95

Tyr Arg Thr Lys Arg Arg Leu Arg Lys Leu Ala Glu Gln Gly Lys Arg
            100                 105                 110

Ser Gly Asp Glu Arg Gln Arg Thr Lys Arg Thr Val Met Asp Asn Asp
            115                 120                 125

Ser Arg Leu Phe Ser Lys Ser Asp Asp Lys Lys Pro Lys Ala Val
            130                 135                 140

Lys Ile Ile Glu Glu Leu Lys Arg Ser Lys Gln Pro Val Ser Pro Gly
145                 150                 155                 160

Ala Arg Leu Thr Ser Phe Leu Asn Ser Ile Phe Gln Ser Asn Ala Lys
                165                 170                 175

Lys Val Lys Leu Cys Ser Val Gly Lys Thr Thr Asp Val Lys Ser Ser
            180                 185                 190

Ser Ser Lys Ser Cys Phe Ser Arg Thr Arg Asn Lys Thr Asp Asn Asn
            195                 200                 205

Asn Asn Asn Cys Lys Lys Leu Glu Arg Ser Ile Arg Phe Tyr Pro Val
            210                 215                 220

Arg Val Thr Ile Asp Gly Asp Cys Arg Asp Tyr Ala Gln Lys His Ile
225                 230                 235                 240

Thr Arg Val Arg Lys Pro Ile Pro Glu Phe Thr Ala Lys Lys Ser Val
                245                 250                 255

Lys Glu Glu Ile Lys Thr Asn Asp His His Thr Glu Phe Thr Cys Ile
            260                 265                 270

Thr Arg Asn Ile Gly Leu Lys Asp Phe Val Arg Ser Asn Lys Tyr Glu
            275                 280                 285

Gly Lys Glu Glu Glu Glu Asp Ala Trp Ser His Ser Ser Ser Asp Leu
            290                 295                 300

Phe Glu Leu Asp Ser Tyr Arg Ile Gly Met Gly Arg Tyr Leu Lys Glu
305                 310                 315                 320

Leu Pro Val Tyr Glu Thr Thr Asp Phe Lys Thr Asn Gln Ala Ile Ala
                325                 330                 335

Arg Ser Leu Leu Leu
            340

<210> SEQ ID NO 8
<211> LENGTH: 286
<212> TYPE: PRT
<213> ORGANISM: Brassica rapa

<400> SEQUENCE: 8

Met Arg Lys Lys Gln Asn Arg Ala Ala Ser Leu Asp Glu Asn Arg Val
1               5                   10                  15

Cys Leu Glu Lys Ile Leu Leu Asn Arg Arg Lys Thr Ala Asp Asp Phe
                20                  25                  30

Ala Val Asn Arg Arg Lys Thr Ala Glu Ile Asn Thr Val Glu Pro Val
            35                  40                  45

Phe Phe Lys His Ser Ser Ser Ser Ser Asp Ser Ser Gly Phe Ser
        50                  55                  60

Ser Ser Glu Ser Asp Ser Phe Tyr Lys Arg Thr Arg Ser Ser Arg Ser
65                  70                  75                  80

Pro Pro Ala Ile His His His Pro Lys Pro Ile Arg Thr Ala Val Glu
                85                  90                  95

Arg Leu Glu Arg Pro Asn Asn Lys Val Lys Ser Lys Ala Leu Lys Met
            100                 105                 110
```

```
Tyr Ser Asp Leu Lys Lys Val Lys Gln Pro Ile Ser Pro Gly Gly Arg
        115                 120                 125

Leu Ala Thr Phe Leu Asn Ser Leu Phe Thr Gly Asn Thr Lys Lys Pro
130                 135                 140

Asn Lys Thr Val Ser Thr Ala Thr Ser Ser His Thr Thr Cys Ser Ser
145                 150                 155                 160

Ala Ser Ser Phe Ser Arg Ser Cys Leu Ser Lys Thr Thr Ser Ser Ser
            165                 170                 175

Glu Lys Ser Lys Arg Ser Val Arg Phe Cys Pro Val Asn Val Ile Leu
            180                 185                 190

Asp Glu Asp Ser Lys Gln Arg Glu Ser Ile Arg His His Gln Ser Arg
            195                 200                 205

Val Met Glu Glu Asn Arg Arg Val Ile Glu Ala Ala Lys Glu Leu Ile
    210                 215                 220

Arg Thr Tyr Arg Glu Asn Lys Asp Val Glu Glu Asp Asp Asp
225                 230                 235                 240

Asp Asp Asp Ala Ala Ser Cys Ala Ser Ser Asp Leu Phe Glu Leu Asp
                245                 250                 255

Asn Leu Ser Ser Ile Gly Ile Glu Arg Tyr Arg Glu Glu Leu Pro Val
            260                 265                 270

Tyr Glu Thr Thr Arg Leu Thr Thr Asn Arg Ile Ile Ser Arg
        275                 280                 285

<210> SEQ ID NO 9
<211> LENGTH: 306
<212> TYPE: PRT
<213> ORGANISM: Brassica rapa

<400> SEQUENCE: 9

Met Asp Pro Trp Asp Lys Thr Asn Ser Leu Asp His His His Arg
1               5                   10                  15

Arg Gln Asp His Arg His Pro Ser Phe Ser Ser Thr Leu Leu Asp Gln
                20                  25                  30

Ile Tyr Asn Ser Ile Asp Ser Ser Ser Ala Val Asn Arg Arg Ala Val
            35                  40                  45

Ala Gly Asp Ser Val Arg Ser Arg Asn Leu Lys Thr Ala Glu Pro Val
    50                  55                  60

Phe Phe Lys His Trp Ser Ser Ser Ser Ser Asp Ser Ser Gly Phe
65                  70                  75                  80

Ser Ser Ser Glu Ser Asp Ser Phe Tyr Arg Arg Ser Arg Ser Ser Arg
                85                  90                  95

Ser Pro Pro Glu Ile Pro His Pro Lys Pro Ile Arg Thr Thr Val Glu
            100                 105                 110

Arg Leu Glu Arg Pro Asn Asn Asn Asn Asn Asn Asn Asn Lys Val
            115                 120                 125

Lys Ser Lys Ala Leu Lys Met Tyr Ser Asp Leu Lys Lys Val Lys Gln
    130                 135                 140

Pro Ile Ser Pro Gly Arg Arg Leu Ala Thr Phe Leu Asn Ser Ile Phe
145                 150                 155                 160

Thr Gly Asn Ser Lys Lys Pro Asn Lys Thr Ala Thr Ser Ser Ser Thr
                165                 170                 175

Thr Cys Ser Ser Ala Ser Ser Phe Ser Lys Ser Cys Leu Ser Lys Thr
            180                 185                 190

Pro Ser Ser Ser Glu Lys Ser Lys Arg Ser Val Arg Phe Cys Glu Ser
```

```
                195                 200                 205
Thr Arg Gln Arg Gln Asn Phe Asp Thr Phe Glu Ser Arg Val Met Glu
    210                 215                 220

Glu Asn Arg Arg Val Ile Glu Ala Ala Lys Glu Leu Ile Arg Thr Tyr
225                 230                 235                 240

Gln Lys Asn Lys Asp Val Val Asn Ile Ile Gly Lys Glu Glu Glu Asp
                245                 250                 255

Asp Glu Glu Asp Asp Asp Gly Gly Ser Cys Ala Ser Ser Asp Leu
        260                 265                 270

Phe Glu Leu Asp His Leu Ser Val Ile Gly Ile Asp Ser Tyr Arg Glu
                275                 280                 285

Glu Leu Pro Val Tyr Glu Thr Thr Arg Phe Asn Thr Asn Arg Ile Ile
    290                 295                 300

Ser Arg
305

<210> SEQ ID NO 10
<211> LENGTH: 310
<212> TYPE: PRT
<213> ORGANISM: Oryza sativa

<400> SEQUENCE: 10

Met Glu Arg Trp Ala Ala Pro Lys Val Thr Ala Gly Ser Ala Arg Arg
1               5                   10                  15

Tyr Val Ala Asp Gln Pro Ser Phe Ser Ser Thr Leu Leu Asp Ala Ile
                20                  25                  30

Tyr Lys Ser Met Asp Glu Gln Pro Gly His Gly Gly Ala Thr Gly
            35                  40                  45

Val Glu Ala Val Ala Ala Ala Lys Lys Gln His Glu Ala Ala Leu
    50                  55                  60

His Tyr Gly Asn Tyr Tyr Lys Pro Ser Leu Ala Gly Ser Tyr Arg Ala
65                  70                  75                  80

Arg Ala Pro Gly Pro His Ala Thr Thr Ser Ser Ser Glu Cys Ser
                85                  90                  95

Ser Tyr Gly Gly Phe Ser Ser Glu Ala Glu Ser Ser His His Arg
            100                 105                 110

Arg Leu Arg Pro Ile Arg Thr Thr Val Pro Gly Gly Ala Pro Gly Pro
    115                 120                 125

Ala Pro Glu Lys Lys Ala Lys Lys Pro Gly Ala Ser Ile Arg Ala Lys
130                 135                 140

Leu Arg Asp Leu Arg Lys Pro Ala Ser Pro Gly Ala Arg Leu Ala Gly
145                 150                 155                 160

Phe Leu Asn Ser Ile Phe Ala Gly Lys Arg Ala Pro Ala Thr Pro Pro
                165                 170                 175

Ser Ala Thr Ala Gly Ala Glu Ser Ala Cys Ser Thr Ala Ser Ser Tyr
            180                 185                 190

Ser Arg Ser Cys Leu Ser Lys Thr Pro Ser Thr Arg Gly Gln Ala Lys
    195                 200                 205

Arg Thr Val Arg Phe Leu Asp Ser Asp Thr Glu Ser Leu Ala Ser Ser
210                 215                 220

Thr Val Val Asp Arg Arg Val Pro Val Glu Ala Val Gln Gln Met
225                 230                 235                 240

Leu Leu Gln Arg Met Glu Met Glu Ser Asp Glu Asp Asp Asp Glu Ser
                245                 250                 255
```

```
Ser Asp Ala Ser Ser Asp Leu Phe Glu Leu Glu Asn Phe Ala Ala Ile
            260                 265                 270

Ala Pro Ala Gly Ala Ala Tyr Arg Asp Glu Leu Pro Val Tyr Glu Thr
        275                 280                 285

Thr Arg Val Ala Leu Asn Arg Ala Ile Gly His Gly Tyr Gly His Gly
    290                 295                 300

Arg Ser Ala Arg Val Val
305             310

<210> SEQ ID NO 11
<211> LENGTH: 337
<212> TYPE: PRT
<213> ORGANISM: Oryza sativa

<400> SEQUENCE: 11

Met Arg Asp Met Glu Met Arg Trp Ala Ala Pro Ala Pro Ala Ala Arg
1               5                   10                  15

Gly Arg Gly Arg Ala Arg Arg Ala Pro Asp Gln Pro Ser Phe Ser
            20                  25                  30

Ser Thr Leu Leu Asp Ala Ile Cys Asp Ser Met Asp Glu Gly Gly Glu
        35                  40                  45

Asp Gly Arg Thr Arg Asn Ala Ala Ser Ala Ala Lys Lys Arg Gln
    50                  55                  60

Glu Ala Ala Asn Ser Tyr His Tyr Tyr Cys Tyr Lys Pro Ser Leu
65                  70                  75                  80

Ala Ala Ser Tyr Arg Ala Ala Pro Ala Leu Gly Ser Thr Ala Asp Cys
                85                  90                  95

Pro Gly Arg Gly Tyr Phe Ser Ser Glu Val Glu Tyr Ser Leu Arg
            100                 105                 110

Arg Leu Arg Pro Ile Arg Thr Ser Ala Ala Gly Ala Gly Asp Gly
        115                 120                 125

Ala Ala Val Ala Arg Lys Gln Arg His Glu Gln Pro Asp Val Glu Lys
    130                 135                 140

Thr Ala Lys Thr Lys Pro Gly Ser Ala Ser Arg Ala Cys Arg Arg
145                 150                 155                 160

Pro Ala Ser Pro Gly Ala Arg Leu Ala Ser Leu Leu Asn Ser Ile Phe
                165                 170                 175

Ser Gly Lys Arg Pro Ser Ala Gln Arg Pro Ala Cys Ser Pro Asp Tyr
            180                 185                 190

Pro Glu Pro Ala Cys Ser Thr Ala Pro Pro Ser Ser Ser Ser Tyr
        195                 200                 205

Ala Arg Arg Pro Cys His Ala Lys Thr Pro Arg Thr Pro Pro Thr Thr
    210                 215                 220

Thr Thr Thr Ala Arg Ala Arg Pro Ser Arg Ser Arg Thr Val Arg Phe
225                 230                 235                 240

Leu Asp Ile Asp Gly Lys Val Ala Val Ala Ala Val Ala Gly Cys
                245                 250                 255

Arg Arg Ile Pro Val Met Glu Val Glu Ala Asp Thr Asp Gly Gly
            260                 265                 270

Glu Glu Ser Ser Asp Ala Ser Ser Asp Leu Phe Glu Leu Asp Ser Leu
        275                 280                 285

Ala Ala Ile Ala Pro Ala Gly Gly Arg Asp Gly Ser Tyr Gly Asp Glu
    290                 295                 300

Leu Pro Val Tyr Gly Thr Thr Gly Val Gly Ile Arg Arg Asp Ile Gly
305                 310                 315                 320
```

Arg Arg Arg Pro Tyr Gly His Ala Pro Cys Arg Ser Trp Ser Arg Ala
            325                 330                 335

Val

<210> SEQ ID NO 12
<211> LENGTH: 311
<212> TYPE: PRT
<213> ORGANISM: Zea mays

<400> SEQUENCE: 12

Met Glu Arg Trp Arg Asp Lys Asp Lys Gly Ala Ala Pro Ala Pro
1               5                   10                  15

Gly Arg Ala Arg Arg Tyr Gly Asp Gln Pro Ser Phe Ser Ser Thr Leu
                20                  25                  30

Leu Asn Ala Ile Tyr Lys Ser Met Asp Glu Pro Asp Asp Gly Val Thr
            35                  40                  45

Ser Ser Ser Ser Thr Ala Ala Lys Lys Gln Asn Gln Asp Leu Arg His
50                  55                  60

Ser Cys Tyr Tyr Tyr Lys Ala Ser Leu Ala Ala Gly Ser Tyr Arg Gly
65                  70                  75                  80

Ser Ser Arg Ala Ala Ala Pro Arg Gly Pro Gln Ala Ala Thr Thr Ser
                85                  90                  95

Ser Ser Ser Asp Gln Cys Ser Ser Tyr Gly Gly Phe Ser Ser Glu
            100                 105                 110

Ala Glu Ser Ser Gln His Arg Arg Leu Arg Pro Ile Arg Thr Ser Leu
            115                 120                 125

Ala Thr Thr Ala Val Ala Val Ala Ala Pro Ala Leu Ala Pro Glu Lys
            130                 135                 140

Lys Lys Ala Gly Val Ser Ile Arg Ala Arg Leu Arg Asp Leu Arg Arg
145                 150                 155                 160

Lys Pro Ala Ser Pro Gly Pro Ala Arg Leu Ala Gly Phe Leu Asn
                165                 170                 175

Ala Ile Phe Ser Gly Arg Arg Ala Pro Pro Ser Ala Ser Ser Cys Ser
                180                 185                 190

Arg Ser Cys Leu Ser Glu Thr Pro Ser Thr Arg Gly Gln Pro Lys Arg
            195                 200                 205

Thr Val Arg Phe Leu Asp Ser Asp Gly Gly Glu Arg Arg Thr
            210                 215                 220

Val Pro Val Gly Val Ala Pro Glu Leu Glu Gln Met Leu Leu His Arg
225                 230                 235                 240

Met Glu Val Asp Ser Gly Asp Asp Asp Glu Ser Ser Asp Ala
                245                 250                 255

Ser Ser Asp Leu Phe Asp Leu Glu Asn Phe Ala Ala Val Asp Pro Asp
            260                 265                 270

Gly Gly Ala Ala Tyr Ser Asp Glu Leu Pro Val Tyr Glu Thr Thr Arg
            275                 280                 285

Leu Val Leu Gly His Arg Ala Ile Gly His Gly Tyr Ala Arg Thr Gly
            290                 295                 300

Gly Val Pro Thr Arg Val Val
305                 310

<210> SEQ ID NO 13
<211> LENGTH: 312
<212> TYPE: PRT
<213> ORGANISM: Zea mays

<400> SEQUENCE: 13

```
Met Glu Arg Pro Trp Arg Asp Lys Asp Lys Gly Ala Ala Pro Ala
1               5                   10                  15

Ala Gly Arg Ala Arg Arg Tyr Gly Asp Gln Pro Ser Phe Ser Ser Thr
            20                  25                  30

Leu Leu Asp Ala Ile Tyr Arg Ser Met Asp Glu Pro Asp Asp Gly Val
        35                  40                  45

Thr Ser Ser Ser Ser Thr Ala Lys Lys Gln Asn Gln Asp Leu Arg
    50                  55                  60

His Ser Cys Tyr Tyr Tyr Lys Ala Ser Leu Ala Ala Gly Ser Tyr Arg
65                  70                  75                  80

Gly Ser Ser Arg Ala Ala Ala Pro Arg Gly Pro Gln Ala Ala Thr Thr
                85                  90                  95

Ser Ser Ser Ser Asp Gln Cys Ser Ser Tyr Gly Gly Phe Ser Ser Ser
            100                 105                 110

Glu Ala Glu Ser Ser Gln His Arg Arg Leu Arg Pro Ile Arg Thr Ser
        115                 120                 125

Leu Ala Thr Thr Ala Val Ala Val Ala Ala Pro Ala Leu Ala Pro Glu
    130                 135                 140

Lys Lys Lys Ala Gly Val Ser Ile Arg Ala Arg Leu Arg Asp Leu Arg
145                 150                 155                 160

Arg Lys Pro Ala Ser Pro Gly Pro Gly Ala Arg Leu Ala Gly Phe Leu
                165                 170                 175

Asn Ala Ile Phe Ser Gly Arg Arg Ala Pro Pro Ser Ala Ser Ser Cys
            180                 185                 190

Ser Arg Ser Cys Leu Ser Glu Thr Pro Ser Thr Arg Gly Gln Pro Lys
        195                 200                 205

Arg Thr Val Arg Phe Leu Asp Ser Asp Gly Gly Glu Arg Arg Arg
    210                 215                 220

Thr Val Pro Val Gly Val Ala Pro Glu Leu Glu Gln Met Leu Leu His
225                 230                 235                 240

Arg Met Glu Val Asp Ser Gly Asp Asp Asp Asp Glu Ser Ser Asp
                245                 250                 255

Ala Ser Ser Asp Leu Phe Asp Leu Glu Asn Phe Ala Ala Val Asp Pro
            260                 265                 270

Asp Gly Gly Ala Ala Tyr Ser Asp Glu Leu Pro Val Tyr Glu Thr Thr
        275                 280                 285

Arg Leu Val Leu Gly His Arg Ala Ile Gly His Gly Tyr Ala Arg Thr
    290                 295                 300

Gly Gly Val Pro Thr Arg Val Val
305                 310

<210> SEQ ID NO 14
<211> LENGTH: 316
<212> TYPE: PRT
<213> ORGANISM: Zea mays

<400> SEQUENCE: 14

Met Glu Arg Trp Gly Asp Lys Asp Arg Gly Ala Ala Val Pro Ala Pro
1               5                   10                  15

Gly Arg Leu Arg Arg Tyr Ala Asp Gln Pro Ser Phe Ser Ser Ser Leu
            20                  25                  30

Leu Asp Ala Ile Tyr Lys Ser Met Asp Glu Pro Gly Asp Gly Ala Thr
        35                  40                  45
```

```
Ser Ala Ala Ala Gly Ala Thr Lys Met Gln Ser His Gln Asp Leu
    50              55                  60

His Tyr Ser Tyr Tyr Lys Thr Ser Leu Ala Gly Ser Tyr Arg Gly
65              70                  75                  80

Ser Arg Ala Ala Ala Ala His Ala Ala Thr Thr Thr Ser Ser Ser
            85                  90                  95

Ser Glu Cys Ser Ser Tyr Gly Gly Phe Ser Ser Glu Ala Glu Ser
        100                 105                 110

Ser Gln His Arg Arg Leu Arg Pro Ile Arg Thr Ser Val Gly Ala Ala
        115                 120                 125

Ala Ser Pro Ala Pro Ala Pro Glu Lys Lys Lys Ala Gly Ala Asn
    130                 135                 140

Ile Arg Ala Lys Leu Arg Asp Leu Arg Lys Pro Ala Ser Pro Gly Ala
145                 150                 155                 160

Arg Leu Ala Gly Phe Leu Asn Thr Ile Phe Ser Gly Arg Arg Ala Pro
                165                 170                 175

Ala Thr Pro Pro Ser Arg Gly Ala Glu Ser Ser Ala Cys Ser Thr Ala
            180                 185                 190

Ser Ser Tyr Ser Arg Ser Cys Leu Ser Lys Thr Pro Ser Thr Arg Gly
        195                 200                 205

Gln Pro Lys Arg Thr Val Arg Phe Leu Asp Ser Asp Gly Glu Ala
    210                 215                 220

Ala Ala Ala Ala Pro Gly Gly Glu Arg Arg Val Gln Val Gly Val
225                 230                 235                 240

Ala Glu Leu Glu Arg Met Leu Leu His Arg Met Glu Met Asp Ser Asp
                245                 250                 255

Glu Asp Asp Glu Asp Glu Glu Gly Ser Asp Ala Ser Ser Asp Leu Phe
            260                 265                 270

Asp Leu Glu Asn Phe Ala Ala Gly Ala Pro Asp Ala Ala Ala Ala Tyr
        275                 280                 285

Arg Asp Glu Leu Pro Val Tyr Glu Thr Thr Arg Val Val Leu Gly His
    290                 295                 300

Arg Ala Ile Gly His Gly Arg Ser Ala Arg Val Val
305                 310                 315

<210> SEQ ID NO 15
<211> LENGTH: 336
<212> TYPE: PRT
<213> ORGANISM: Sorghum bicolor

<400> SEQUENCE: 15

Met Glu Arg Trp Pro Pro Val Pro Ala Pro Glu Arg Pro Arg Arg
1               5                   10                  15

Pro Gly Gln Pro Ser Phe Ser Ser Thr Leu Leu Asp Ala Ile Cys Asp
                20                  25                  30

Ser Leu Asp Glu Gln Ala Gly Gly Gln Gly Ala Ala Glu Arg Ala
        35                  40                  45

Ala Glu Ala Pro Thr Pro Gly Ser Ala Lys Lys Gln Gln Gln Ala Ala
    50                  55                  60

Leu His Tyr Tyr Tyr Tyr Lys Pro Ser Leu Ala Ala Ser His Arg
65                  70                  75                  80

Ala Ala Arg Ala Ala Pro Ala Pro Ala Asp Asp Cys Ser Ser Gly Arg
                85                  90                  95

Gly Tyr Phe Ser Ser Ser Glu Val Glu Tyr Ser Leu Arg Arg Leu Arg
```

```
                    100                 105                 110
Pro Ile Arg Thr Ser Gly Gly Val Gly Pro Ala Ser Val Ala Pro
            115                 120                 125

Ala Glu Lys Gln Gln Ala Val Pro Pro Gly Ser Ala Thr Ala Arg Arg
    130                 135                 140

Ala Arg Lys Pro Ser Ala Ala Pro Ala Ser His Gly Gly Cys Arg Arg
145                 150                 155                 160

Pro Ala Ser Pro Gly Ala Arg Leu Ala Ser Leu Leu Asn Ala Ile Phe
                165                 170                 175

Ser Gly Lys Arg His Ser Ala Arg Gln His Pro Ala Pro Ala Asp Asp
            180                 185                 190

Glu Pro Thr Ala Cys Ser Thr Ala Pro Ser Ser Ala Arg Pro Cys Leu
        195                 200                 205

Ala Lys Thr Pro Pro Ser Ala Thr Ala Arg Ala Arg Ala Thr His Ser
    210                 215                 220

Arg Arg Ser Arg Thr Val Arg Phe Leu Asp Ile Glu Gly Glu Val Ala
225                 230                 235                 240

Val Ala Ala Ala Ala Gly Cys Arg Arg Phe Pro Val Val Glu Val
                245                 250                 255

Glu Gly Ser Asp Gly Gly Glu Ser Ser Asp Ala Ser Ser Asp Leu
            260                 265                 270

Phe Glu Leu Glu Asn Leu Ala Ala Leu Ala Pro Ala Asn Gly Gly Ser
        275                 280                 285

Gly Cys Arg Arg Thr Cys Glu Asp Glu Leu Pro Val Tyr Gly Thr Thr
    290                 295                 300

Gly Ala Gly Leu Ala Gln Asp Ile Gly Leu Val Arg Arg Arg Pro Phe
305                 310                 315                 320

Gly Tyr Val Ser His Gly Arg Ser Cys Arg Gly Leu Phe Asp Phe Lys
                325                 330                 335

<210> SEQ ID NO 16
<211> LENGTH: 223
<212> TYPE: PRT
<213> ORGANISM: Sorghum bicolor

<400> SEQUENCE: 16

Met Glu Arg Trp Gly Asp Lys Asp Lys Arg Ala Ala Gly Ala Ala Pro
1               5                   10                  15

Gly Arg Ala Arg Arg Tyr Ala Asp Gln Pro Ser Phe Ser Ser Thr Leu
                20                  25                  30

Leu Asp Ala Ile Tyr Lys Ser Met Asp Glu Pro Asp Asp Gly Val Thr
            35                  40                  45

Ser Ser Gly Ala Ala Thr Ala Ala Thr Lys Lys Gln Asn His Asp
    50                  55                  60

Leu His Tyr Ser Tyr Tyr Tyr Lys Ala Ser Leu Ala Gly Ser Tyr Arg
65                  70                  75                  80

Gly Ser Ser Arg Ala Ala Ala Pro Gly Pro His Ala Ala Thr Thr Ser
                85                  90                  95

Ser Ser Ser Glu Cys Ser Ser Tyr Gly Gly Phe Ser Ser Ser Glu Ala
            100                 105                 110

Glu Ser Ser Gln His Arg Arg Leu Arg Pro Ile Arg Thr Ser Ala Ala
        115                 120                 125

Ala Gly Ala Ala Ala Thr Ala Pro Ala Pro Ala Leu Ala Pro Glu Gln
    130                 135                 140
```

```
Lys Lys Lys Ala Ala Lys Ala Gly Ala Asn Ile Arg Ala Lys Leu
145                 150                 155                 160

Arg Glu Leu Arg Lys Pro Ala Ser Pro Gly Ala Ser Pro Gly Ala Arg
            165                 170                 175

Leu Ala Gly Phe Leu Asn Ala Ile Phe Asn Gly Arg Arg Ala Pro Gln
            180                 185                 190

Thr Ala Tyr Ala Tyr Ser Arg Ser Cys Leu Ser Lys Asn Pro Ser Ile
        195                 200                 205

Arg Gly Gln Pro Lys Arg Thr Val Gln Ile Leu Glu Ser Asp Asp
    210                 215                 220
```

<210> SEQ ID NO 17
<211> LENGTH: 327
<212> TYPE: PRT
<213> ORGANISM: Brachypodium distachyon

<400> SEQUENCE: 17

```
Met Glu Arg Arg Gly Glu Lys Gly Ala Ala Ala Arg Ala Arg Arg
1               5                   10                  15

Pro Gln Gly Ala Ala Glu Gln Pro Ser Phe Ser Ser Thr Leu Leu Asp
            20                  25                  30

Ala Ile Tyr Lys Ser Met Asp Glu Pro Gly His Asp Ala Val Ser Lys
        35                  40                  45

Lys Lys Gln Gln Glu Lys Glu Glu Ala Leu His Tyr Ser Tyr Tyr Tyr
    50                  55                  60

Arg Pro Ser Leu Ala Gly Ser Tyr Arg Ala Arg Ala Pro Gly Pro Ala
65                  70                  75                  80

His Ala Thr Thr Thr Thr Ser Ser Ser Asp Cys Ser Ser Tyr Gly
            85                  90                  95

Gly Phe Ser Ser Ser Glu Ala Glu Thr Ser Ser Gly Arg His His His
            100                 105                 110

Arg Arg Leu Arg Pro Ile Arg Thr Ala Ala Ala Pro Ala Pro Pro
        115                 120                 125

Ala Pro Glu Lys Lys Ala Ser Lys Lys Gln Gln Val Ala Pro Gly Ala
    130                 135                 140

Ser Ile Arg Ala Lys Leu Arg Asp Leu Arg Lys Ala Pro Ala Ser Pro
145                 150                 155                 160

Gly Ala Arg Leu Ala Gly Phe Leu Asn Thr Ile Phe Ala Gly Gly
            165                 170                 175

Gly Lys Arg Ala Pro Gln Thr Pro Pro Ser Ala Ser Ala Ala Ala Glu
        180                 185                 190

Tyr Ala Cys Ser Thr Ala Ser Ser Ala Ala Ser Tyr Ser Arg Ser Cys
    195                 200                 205

Leu Ser Lys Thr Pro Ser Thr Arg Gly Gly Gly Gln Gln Gln Ala
    210                 215                 220

Gly Arg Thr Val Arg Phe Val Asp Ser Ala Ala Glu Ala Pro Ala Thr
225                 230                 235                 240

Val Pro Gly Arg Arg Met Pro Ala Arg Ala Val Glu Gln Met Leu Leu
            245                 250                 255

Arg Arg Met Glu Met Glu Ser Asp Glu Glu Asp Glu Glu Ser Ser Asp
        260                 265                 270

Ala Ser Ser Asp Leu Phe Glu Leu Glu Asn Phe Thr Ala Ala Pro Pro
    275                 280                 285

Gly Ala Ala Gly Tyr Arg Asp Glu Leu Pro Val Tyr Glu Thr Thr Arg
    290                 295                 300
```

-continued

```
Val Val Leu Asn Arg Gly Ser Ile Gly Gly His His Gly Tyr Gly His
305                 310                 315                 320

Gly Arg Ser Ala Arg Val Val
                325

<210> SEQ ID NO 18
<211> LENGTH: 292
<212> TYPE: PRT
<213> ORGANISM: Medicago truncatula

<400> SEQUENCE: 18

Met Ser Leu Ala Gly Leu Ile Ile Asp Gln Glu Met Asn His Asn Lys
1               5                   10                  15

Lys Ser Phe His Arg Arg Asn Asp Ser Gly Glu Leu Asp Val Phe Glu
                20                  25                  30

Ala Ser Arg Tyr Phe Ser Gly Tyr Asn Glu Val Ile Gly Tyr Asn Asn
            35                  40                  45

Ser Ser Thr Phe Thr Gln Lys Ile Met Arg Glu Arg Asn Gly Tyr
        50                  55                  60

Lys Gly Arg Ile Ser Leu Asp Met Pro Met Arg Ser Leu Leu Pro Gln
65                  70                  75                  80

Gln Phe His Gly Gly Ile Asp Gln Lys Gln Met Lys Glu Lys Lys His
                85                  90                  95

Asn Lys Gln Pro Ser Ser Pro Gly Gly Arg Leu Ala Ser Phe Leu Asn
                100                 105                 110

Ser Leu Phe Asn Gln Ser Thr Ser Lys Lys Ser Lys Ser Ser
            115                 120                 125

Gln Ser Met Lys Asp Glu Asp Glu Ser Pro Gly Gly Arg Arg Arg Arg
130                 135                 140

Arg Ser Ser Ile Ser His Phe Arg Ser Ser Thr Ala Asp Ser Arg
145                 150                 155                 160

Ser Ile Tyr Ser Leu Asn Ser Gly Phe Arg Thr Pro Pro Tyr Val Asn
                165                 170                 175

Thr Pro Thr Lys Gly Cys Arg Glu Phe Lys Thr Leu Leu Ser Asp Gln
                180                 185                 190

Lys Asn Glu Val Ser Leu Lys Lys Ser Ser Thr Thr Leu Gln Asn Glu
            195                 200                 205

Leu Cys Trp Asp Asp Lys Lys Lys Arg Asp Ser Asn Leu Lys Gln Phe
210                 215                 220

Val Glu Lys Lys Tyr Tyr Glu Glu Glu Lys Arg Glu Val Arg Lys Phe
225                 230                 235                 240

Asn Glu Val Asp Asp Gly Ala Glu Ser Asp Ser Ser Ser Asp Leu Phe
                245                 250                 255

Glu Leu Gln Asn Tyr Glu Leu Ser His Tyr Ser Ser Gly Leu Pro Val
            260                 265                 270

Tyr Glu Thr Thr Asn Met Asp Asn Ile Lys Arg Gly Ser Thr Ile Ser
        275                 280                 285

Asn Val Pro Leu
    290

<210> SEQ ID NO 19
<211> LENGTH: 374
<212> TYPE: PRT
<213> ORGANISM: Medicago truncatula

<400> SEQUENCE: 19
```

```
Met Tyr Lys Phe Glu Asn Thr His Ile Glu Lys Arg Phe His Asn Asn
1               5                   10                  15

Phe Glu Asn His Ser Phe Ser Ser Thr Leu Leu Asp Gln Ile Tyr Arg
            20                  25                  30

Ser Ile Asp Glu Gly Asp Arg Lys Val Ser Asp Met Lys Phe Tyr Thr
        35                  40                  45

Glu Thr Thr Phe Gln Lys Gln Ser Lys Thr Asn Ala Lys Phe Asn Arg
50                  55                  60

Val Phe Glu Glu Gln Gln Pro Tyr Leu Arg Gly Val Cys Lys Glu Lys
65                  70                  75                  80

Glu Lys Ile Thr Thr Gln Ile Asp Arg Lys Leu His Leu Asp His Glu
                85                  90                  95

Ile His Asp Gln Asp Val Met Phe Phe Ser Ser Thr Ser Ser Ser Ser
            100                 105                 110

Asp Ser Ser Gly Leu Leu Ser Ser Ser Glu Thr Glu Ser Met Tyr
        115                 120                 125

Lys Ala Lys Ser Arg Gly Gly Ser Cys Phe Ala Pro Ser Arg Pro Lys
130                 135                 140

Pro Val Lys Thr Thr Val Pro Pro Glu Arg Arg Ile Ile Ala Asn Asp
145                 150                 155                 160

Glu Asp Thr Leu Ile Lys Ser Lys Ser Arg Ala Leu Lys Ile Tyr Asn
                165                 170                 175

Asn Leu Lys Lys Val Lys Gln Pro Ile Ser Pro Gly Gly Lys Leu Thr
            180                 185                 190

Ser Phe Leu Asn Ser Leu Phe Ile Asn Thr Lys Lys Thr Lys Thr Val
        195                 200                 205

Ser Ser Tyr Glu Asp Ser Asn Ala Glu Arg Lys Gly Lys Pro Gly Gln
210                 215                 220

Ala Ser Thr Thr Cys Ser Ser Ala Ser Ser Tyr Ser Arg Ser Cys Leu
225                 230                 235                 240

Ser Lys Asn Ser Ser Lys Ser Arg Asp Lys Leu His Asn Gly Asp Lys
                245                 250                 255

Arg Thr Val Arg Phe Tyr Pro Val Ser Val Ile Val Asp Glu Asp Asn
            260                 265                 270

Arg Ala Cys Gly His Lys Tyr Leu Asn Lys Gly Val Thr Lys Lys Asn
        275                 280                 285

Glu Glu Val Val Asp Lys Ser Lys Lys Glu Glu Val Ala Arg Glu
290                 295                 300

Phe Leu Arg Glu Tyr His Leu Asn His Lys Ile Leu Arg Asp Phe Ser
305                 310                 315                 320

Met Lys Lys Asn Glu Glu Val Asp Asp Val Ser Ser Cys Ser Ser
                325                 330                 335

Ser Asp Leu Phe Glu Leu Asp His Leu Asp Val Met Gly Asn Asp Arg
            340                 345                 350

Tyr Cys Glu Asp Leu Pro Val Phe Glu Thr Thr His Val Ser Thr Asn
        355                 360                 365

Arg Ala Ile Arg Ile Met
    370

<210> SEQ ID NO 20
<211> LENGTH: 453
<212> TYPE: PRT
<213> ORGANISM: Populus trichocarpa
```

-continued

```
<400> SEQUENCE: 20

Met Asp Arg Trp Glu Lys Pro Leu Arg Asp Asp Arg Tyr Arg His Gln
1               5                   10                  15

Arg Glu Asn Pro Ser Phe Ser Ser Thr Leu Leu Asp Ala Ile Tyr Arg
            20                  25                  30

Ser Ile Asp Glu Asn Gly Ser Gly Lys Gly Glu Glu Gln Leu Ile
        35                  40                  45

Tyr Phe Arg Glu Thr Met Arg Lys Lys His Glu Asn Asn Gly Ile Lys
50                  55                  60

Asp Gly Glu Met Thr Ser Leu Gln Arg Ala Cys Met Ile Asp Lys Trp
65                  70                  75                  80

Met Glu Lys Lys Val Ser His Glu Lys Val Ala Val Arg Arg Lys Ser
                85                  90                  95

Met Ala Asp Phe Glu Asn Lys Ser Arg Lys Asp Val Asp Ser Val Leu
            100                 105                 110

Leu Asn Ser Ser Ser Thr Ser Ser Glu Ser Ser Cys Gly Gly Gly Phe
        115                 120                 125

Ser Ser Ser Glu Ser Glu Ser Ile Tyr Gly Val Asn Ser Ser Arg Ser
130                 135                 140

Ser Thr Thr Ser Tyr Thr Met Gln Arg Pro Lys Pro Ile Arg Thr Ser
145                 150                 155                 160

Ile Ser Ala Arg Pro Glu Lys Tyr Gln Arg Arg Glu Asp His His Gln
                165                 170                 175

Ile Asp Met Tyr His Asn His Glu Arg Asn Tyr Ala Pro Asn Gln Lys
            180                 185                 190

Ala Lys His Glu Gly Ser Phe Val Lys Thr Lys Ser Lys Ala Leu Lys
        195                 200                 205

Ile Tyr Gly Asp Leu Lys Lys Val Lys Gln Pro Ile Ser Pro Gly Gly
210                 215                 220

Arg Leu Ala Ser Phe Leu Asn Ser Leu Phe Thr Ala Gly Asn Ala Lys
225                 230                 235                 240

Lys Ala Lys Ile Ser Thr Ser Gly Gly Arg Tyr Glu Glu Arg Lys Leu
                245                 250                 255

Lys Ser Glu Gln Ala Ser Thr Cys Ser Ser Ala Ser Ser Phe Ser Arg
            260                 265                 270

Ser Cys Leu Ser Lys Thr Pro Ser Ser Arg Gly Gly Lys Leu Ser Ser
        275                 280                 285

Asn Asn Gly Ala Lys Arg Ser Val Arg Phe Tyr Pro Val Ser Val Ile
290                 295                 300

Val Asp Glu Asp Cys Arg Pro Cys Gly His Lys Ser Leu Tyr Gly Ser
305                 310                 315                 320

Asp Cys Gln Glu Leu Ser Ser Thr Leu Val Ala Ala Thr Val Thr Thr
                325                 330                 335

Asp Thr Arg Asn Asn Val Pro Thr Ser Gly Glu Glu Leu Lys Phe His
            340                 345                 350

Val Thr Asn Glu Asn Arg Arg Ile Glu Glu Val Ala Arg Asn Leu Leu
        355                 360                 365

Lys Asn Tyr Gln Arg Lys Lys Glu Glu Gln Phe Asp His Met Ser Thr
370                 375                 380

Asp Leu Cys Asn Asp Asn Asn His Glu Val Met Ser Ser Asp Glu Glu
385                 390                 395                 400

Glu Glu Glu Glu Ser Asp Val Ala Ser Cys Ala Ser Ser Asp Leu Phe
                405                 410                 415
```

```
Glu Leu Asp Asn Leu Ser Ala Ile Gly Ile Glu Arg Tyr Arg Glu Glu
            420                 425                 430

Leu Pro Val Tyr Glu Thr Thr His Leu Gly Thr Asn Arg Ala Ile Ala
            435                 440                 445

Asn Gly Leu Ile Leu
        450

<210> SEQ ID NO 21
<211> LENGTH: 380
<212> TYPE: PRT
<213> ORGANISM: Populus trichocarpa

<400> SEQUENCE: 21

Met Asp Arg Trp Glu Lys Pro Leu Arg Asp Arg Tyr Arg His Gln
1               5                   10                  15

Arg Gln Asn Pro Ser Phe Ser Ser Thr Leu Leu Asp Val Ile Tyr Arg
            20                  25                  30

Ser Ile Asp Glu Ser Gly Asn Gly Lys Gly Glu Glu Gln Leu Ile
        35                  40                  45

Phe Tyr Arg Glu Thr Met Arg Lys Lys His Glu Ile Asn His Gly Phe
    50                  55                  60

Lys Gly Glu Glu Met Thr Ser Leu Gln Arg Ala Cys Met Ile Glu Asn
65                  70                  75                  80

Ser Ser Ser Ser Glu Ser Ser Cys Gly Gly Val Phe Ser Ser Ser Glu
                85                  90                  95

Ser Glu Ser Ile Tyr Gly Val Asn Ser Ser Arg Ser Ser Thr Thr Ser
            100                 105                 110

Tyr Thr Met Gln Arg Pro Lys Pro Val Arg Thr Ser Ile Ser Ala Arg
        115                 120                 125

Pro Glu Lys Tyr Gln Arg Arg Glu Asp Leu His Gln Thr Asp Thr Phe
    130                 135                 140

Gln His His Glu Arg Asn Tyr Ala Pro Asn Gln Lys Ala Lys Pro Glu
145                 150                 155                 160

Gly Ser Phe Val Lys Thr Lys Ser Lys Ala Leu Lys Ile Tyr Gly Asp
                165                 170                 175

Leu Lys Lys Val Lys Gln Pro Ile Ser Pro Gly Arg Arg Leu Ala Ser
            180                 185                 190

Phe Leu Asn Ser Leu Phe Thr Thr Gly Asn Ala Lys Lys Ala Lys Ile
        195                 200                 205

Thr Thr Pro Gly Gly Ser Tyr Glu Glu Arg Lys Leu Lys Ser Glu Gln
    210                 215                 220

Ala Ser Thr Cys Ser Ser Ala Ser Ser Phe Ser Arg Ser Cys Leu Ser
225                 230                 235                 240

Lys Thr Pro Ser Ser Arg Gly Gly Lys Leu Ser Ser Asn Asn Gly Ala
                245                 250                 255

Lys Arg Ser Val Arg Phe Tyr Pro Val Ser Val Ile Val Asp Glu Asp
            260                 265                 270

Cys Arg Pro Cys Gly His Lys Asn Leu Tyr Gly Ser Asp Arg Gln Glu
        275                 280                 285

Met Ser Lys Leu Lys Leu His Val Met Asn Glu Asn Arg Arg Ile Glu
    290                 295                 300

Glu Val Ala Arg Asp Leu Leu Lys Asn Tyr Gln Lys Lys Lys Glu Glu
305                 310                 315                 320

His Glu Glu Glu Glu Glu Glu Ser Asp Asp Asp Asp Ile Ala Ser
```

```
                325                 330                 335
Cys Ala Ser Ser Asp Leu Phe Glu Leu Asp Asn Leu Ser Val Val Gly
            340                 345                 350

Ile Glu Arg Tyr Arg Glu Glu Leu Pro Val Tyr Glu Thr Thr His Leu
            355                 360                 365

Gly Thr Asn Arg Ala Ile Ala Thr Gly Leu Phe Leu
            370                 375                 380

<210> SEQ ID NO 22
<211> LENGTH: 311
<212> TYPE: PRT
<213> ORGANISM: Glycine max

<400> SEQUENCE: 22

Met Tyr Thr Thr Lys Arg Glu Gln Gln Arg Leu Arg Phe Gln Asn His
1               5                   10                  15

Ala Lys Lys Pro Ser Phe Ser Ser Ile Leu Leu Asp Gln Ile Tyr Arg
            20                  25                  30

Ser Ile Asp Glu Gly Asn Asp Met Lys Leu Tyr Asn Glu Thr Met Ala
        35                  40                  45

Lys Gln Gln Asn Arg Gly Lys Ser Arg Trp His His His Asn His
    50                  55                  60

Glu His Asp Gln Glu Val Met Phe Phe Ser Ser Thr Ser Ser Ser Ser
65                  70                  75                  80

Asp Ser Ser Ser Gly Leu Leu Ser Ser Ser Asp Thr Glu Ser Leu Tyr
                85                  90                  95

Gly Met Arg Ser Lys Ser Arg Val Ser Cys Phe Ala Pro Ser Arg Pro
            100                 105                 110

Lys Pro Val Val Thr Ser Ala Ser Asn Glu Val Gly Leu Ile Lys Ser
        115                 120                 125

Glu Ser Arg Ala Leu Lys Ile Tyr Asn Asn Leu Lys Lys Val Lys Gln
    130                 135                 140

Pro Ile Ser Pro Gly Gly Lys Leu Ser Asn Phe Leu Asn Ser Leu Phe
145                 150                 155                 160

Ala Thr Gly Gly Ser Val Lys Lys Thr Lys Thr Tyr Asp Asp Asp Ala
                165                 170                 175

Lys Ala Ser Thr Lys Ser Gly Gln Asp Ser Thr Cys Ser Ser Ala Ser
            180                 185                 190

Ser Phe Ser Arg Thr Asn Cys Val Thr Gly Leu Ser Glu Arg Cys Val
        195                 200                 205

Ser Thr Pro Gly His Ser Arg Asn Gly Ser Lys Asn Gln Glu Asp Glu
    210                 215                 220

Glu Leu Arg Val Val Asp Arg Ser Arg Val Glu Glu Ala Ala Arg
225                 230                 235                 240

Glu Phe Leu Lys Glu Tyr His Arg Ser Gln Lys Lys Ser Asp Phe Thr
                245                 250                 255

Asn Leu Asp Val Glu Asp Asp Gly Asp Ala Ser Ser Cys Ser Ser Ser
            260                 265                 270

Asp Leu Phe Glu Leu Asp His Leu Ala Val Met Gly Asn Asp Arg Tyr
        275                 280                 285

Gly Asp Glu Leu Pro Val Tyr Glu Thr Thr Tyr Val Ser Thr Asn Arg
    290                 295                 300

Ala Ile Ala Asn Gly Leu Ile
305                 310
```

<210> SEQ ID NO 23
<211> LENGTH: 430
<212> TYPE: PRT
<213> ORGANISM: Glycine max

<400> SEQUENCE: 23

```
Met Asp Lys Trp Asp Asn Lys Pro Ser Arg Lys Gln His His Arg Glu
1               5                   10                  15

Asn Pro Ser Phe Ser Ser Thr Leu Leu Asp Val Ile Tyr Arg Ser Ile
            20                  25                  30

Asp Glu Asp Pro Thr Asp Glu Lys Glu Glu Ala Gln Leu Ile Phe Tyr
        35                  40                  45

Arg Glu Thr Met Arg Asn Gln Lys Gln Ser Asn Cys Phe Arg Glu Glu
    50                  55                  60

Lys Pro Glu Ala Glu Lys His Asn Ser Arg Arg Ala Arg Lys Val Glu
65                  70                  75                  80

Asn Trp Met Glu Lys Lys Ala Asn Glu Lys Val Val Met Gly Arg Asn
                85                  90                  95

Ser Leu Thr Glu Phe Glu Arg Arg Thr Arg Ser Asn Ser Ile Ser Asn
            100                 105                 110

Thr Leu Ser Met Tyr Ser Ser Ser Thr Ser Ser Glu Ser Ser Ser Val
        115                 120                 125

Gly Gly Phe Ser Ser Ser Glu Ser Glu Ser Phe Tyr Gly Val Gln Arg
    130                 135                 140

Pro Lys Pro Ile Lys Thr Ser Val Ser Asp Lys Thr Lys Thr Lys Thr
145                 150                 155                 160

Thr Phe Asp Ala Ser Leu His Ser His Asn Phe Arg Ser His Ser Ser
                165                 170                 175

Gln Ser Gln Lys Pro Lys His Glu Asn Gly Ser Gly Lys Thr Lys Ser
            180                 185                 190

Lys Ala Leu Lys Ile Leu Tyr Gly Glu Leu Lys Ala Lys Gln Pro
        195                 200                 205

Ile Ser Pro Gly Ala Lys Leu Ala Ser Phe Leu Asn Ser Leu Phe Thr
    210                 215                 220

Ser Ser Gly Asn Ala Lys Lys Ala Lys Val Ser Thr Thr Thr Thr Thr
225                 230                 235                 240

Thr Thr Thr Ser Thr Tyr Arg Pro Val Leu Ile Pro Val Ala Thr Asp
                245                 250                 255

Arg Thr Ala Asp Thr Lys Ser Ala Ala Gln Gln Gln Gln Pro Gly
            260                 265                 270

Ser Thr Cys Ser Ser Ala Ser Ser Phe Ser Arg Ser Cys Leu Ser Lys
        275                 280                 285

Thr Pro Ser Ser Arg Ser Gly Ala Lys Arg Ser Val Arg Phe Cys Pro
    290                 295                 300

Val Ser Val Ile Val Asp Glu Asp Cys Arg Pro Cys Gly His Lys Asn
305                 310                 315                 320

Leu His Glu Gly Glu Glu Ser Asn Gly Lys Asn Arg Ser Glu Glu Leu
                325                 330                 335

Arg Leu His Val Met Gln Glu Ser Arg Arg Val Glu Glu Leu Ala Arg
            340                 345                 350

Asp Leu Leu Lys Asn Tyr Gln Lys Lys Ser Glu Val Glu Phe Asp Asp
        355                 360                 365

Val Met His Tyr Glu Asp Glu Glu Glu Glu Asp Asp Asp Val
    370                 375                 380
```

```
Ala Ser Cys Ser Ser Asp Leu Phe Glu Leu Asp Asn Leu Ser Ala
385                 390                 395                 400

Ile Gly Ile Glu Arg Tyr Arg Glu Glu Leu Pro Val Tyr Glu Thr Thr
                405                 410                 415

His Phe Asn Thr Asn Arg Ala Ile Ala Asn Gly Phe Ile Leu
                420                 425                 430

<210> SEQ ID NO 24
<211> LENGTH: 431
<212> TYPE: PRT
<213> ORGANISM: Glycine max

<400> SEQUENCE: 24

Met Asp Lys Trp Asp Asn Lys Pro Ser Arg Lys Gln His His Arg Glu
1               5                   10                  15

Asn Pro Ser Phe Ser Ser Thr Leu Leu Asp Val Ile Tyr Arg Ser Ile
                20                  25                  30

Asp Glu Asp Pro Thr Glu Glu Lys Glu Ala Gln Leu Ile Phe Tyr
            35                  40                  45

Arg Glu Thr Met Arg Lys Gln Lys Gln Gly Asn Cys Phe Arg Glu Glu
50                  55                  60

Lys Pro Glu Ala Glu Lys His Asn Ser Arg Arg Ala Arg Lys Val Glu
65                  70                  75                  80

Asn Trp Met Glu Lys Arg Ala Ser Glu Lys Val Leu Met Gly Arg Asn
                85                  90                  95

Ser Leu Thr Glu Phe Glu Arg Arg Thr Arg Ser Asn Ser Ile Ser Asn
                100                 105                 110

Thr Leu Ser Met Tyr Ser Ser Thr Ser Glu Ser Ser Val
            115                 120                 125

Gly Gly Phe Ser Ser Ser Glu Ser Glu Ser Phe Tyr Tyr Gly Val Gln
            130                 135                 140

Arg Pro Lys Pro Ile Lys Thr Ser Val Ser Asp Lys Thr Lys Thr Lys
145                 150                 155                 160

Thr Asn Phe Asp Ala Ser Leu His Ser His Asn Phe Arg Ser His Ser
                165                 170                 175

Ser Gln Ser Gln Lys Pro Lys His Glu Asn Gly Phe Gly Lys Thr Lys
            180                 185                 190

Ser Lys Ala Leu Lys Ile Leu Tyr Gly Glu Leu Lys Lys Ala Lys Gln
        195                 200                 205

Pro Ile Ser Pro Gly Ala Lys Leu Ala Ser Phe Leu Asn Ser Leu Phe
210                 215                 220

Thr Ser Thr Gly Asn Ala Lys Lys Ala Lys Val Ser Thr Thr Thr Thr
225                 230                 235                 240

Ser Thr Tyr Arg Pro Val Leu Ile Pro Ile Ala Thr Asp Arg Val Ala
                245                 250                 255

Asp Thr Lys Ser Val Ser Ala Ala Gln Gln Pro Gly Ser Thr Cys
            260                 265                 270

Ser Ser Ala Ser Ser Phe Ser Arg Ser Cys Leu Ser Lys Thr Pro Ser
        275                 280                 285

Ser Arg Ser Gly Ala Lys Arg Ser Val Arg Phe Cys Pro Val Ser Val
        290                 295                 300

Ile Val Asp Glu Asp Cys Arg Pro Cys Gly His Lys Asn Leu His Glu
305                 310                 315                 320

Gly Glu Glu Ser Leu Val Asp Ser Arg Gly Lys Asn Arg Ser Glu Glu
```

```
                      325                 330                 335
Leu Arg Leu His Val Met Gln Glu Ser Arg Val Glu Glu Leu Ala
            340                 345                 350

Arg Asp Leu Leu Lys Asn Tyr Gln Lys Lys Ser Glu Val Glu Phe Asp
                355                 360                 365

Asp Val Met His Tyr Glu Asp Glu Glu Glu Glu Asp Asp Asp
370                 375                 380

Val Ala Ser Cys Ala Ser Ser Asp Leu Phe Glu Leu Asp Asn Leu Ser
385                 390                 395                 400

Ala Ile Gly Ile Glu Arg Tyr Arg Glu Glu Leu Pro Val Tyr Glu Thr
                405                 410                 415

Thr His Phe Asn Thr Asn Arg Ala Ile Ala Asn Gly Phe Ile Leu
                420                 425                 430

<210> SEQ ID NO 25
<211> LENGTH: 327
<212> TYPE: PRT
<213> ORGANISM: Setaria italica

<400> SEQUENCE: 25

Met Glu Arg Trp Gly Glu Lys Gly Ala Ala Pro Ala Pro Gly Arg Ala
1               5                   10                  15

Arg Arg Tyr Ala Asp Gln Pro Ser Phe Ser Ser Thr Leu Leu Asp Ala
                20                  25                  30

Ile Tyr Lys Ser Met Asp Glu Pro Asp Ala Ala Ala Ala Thr Thr
            35                  40                  45

Lys Lys Gln Ser Gln Asp Leu His Tyr Ser Tyr Tyr Tyr Lys Ala Ser
    50                  55                  60

Leu Ala Gly Ser Tyr Arg Ala Gly Arg Ala Ala Ser Ala Val Ala Thr
65                  70                  75                  80

Pro Gly Pro His Ala Thr Thr Ser Ser Ser Glu Cys Ser Ser Tyr
                85                  90                  95

Gly Gly Phe Ser Ser Ser Glu Ala Glu Ser Ser Gln His Arg Arg Leu
                100                 105                 110

Arg Pro Ile Arg Thr Ser Val Ala Ala Ala Gly Glu Ala Pro Ala Pro
            115                 120                 125

Ala Pro Glu Lys Thr Lys Lys Ala Ala Lys Asn Lys Pro Gly Ala Asn
130                 135                 140

Ile Arg Ala Lys Leu Arg Asp Leu Arg Lys Pro Ala Ser Pro Gly Ala
145                 150                 155                 160

Arg Leu Ala Gly Phe Leu Asn Ala Ile Phe Asn Gly Lys Arg Ala Pro
                165                 170                 175

Pro Thr Pro Pro Ser Ala Ser Arg Ala Ala Ala Ser Glu Ser Ala
                180                 185                 190

Cys Ser Ser Ala Ser Ser Tyr Ser Arg Ser Cys Leu Ser Lys Thr Pro
                195                 200                 205

Ser Thr Arg Gly Gln Pro Lys Arg Thr Val Arg Phe Met Asp Ser Asp
                210                 215                 220

Thr Glu Ala Ala Ala Val Pro Ala Ala Gly Thr Glu Arg Arg
225                 230                 235                 240

Val Gln Val Gly Val Val Glu Leu Glu Arg Met Leu Leu His Arg Met
                245                 250                 255

Glu Met Asp Ser Asp Glu Asp Asp Glu Ser Ser Asp Ala Ser Ser Asp
                260                 265                 270
```

Leu Phe Glu Leu Glu Asn Phe Ala Val Ala Pro Ala Gly Gly
            275                 280                 285

Ala Gly Ala Tyr Arg Asp Glu Leu Pro Val Tyr Glu Thr Thr Arg Val
        290                 295                 300

Val Leu Asn Arg Ala Ile Gly His Gly His Gly His Gly Tyr Ala His
305                 310                 315                 320

Gly Arg Ser Thr Arg Val Val
                325

<210> SEQ ID NO 26
<211> LENGTH: 325
<212> TYPE: PRT
<213> ORGANISM: Setaria italica

<400> SEQUENCE: 26

Met Glu Arg Trp Ala Pro Ala Pro Ala Arg Glu Arg Pro Arg
1               5                   10                  15

Arg Arg Ala Gly Gln Pro Ser Phe Ser Ser Thr Leu Leu Asp Ala Ile
            20                  25                  30

Cys Asp Ser Leu Asp Glu Gln Pro Gly Gly Gly Gly Ala Gly Thr Thr
            35                  40                  45

Ala Ala Ala Ala Arg Ser Ala Gly Ser Ala Lys Lys Gln Gln Glu Ala
50                  55                  60

Ala Met His Tyr Tyr Tyr Lys Pro Ser Leu Ala Ala Ser His Arg
65                  70                  75                  80

Ala Ala Pro Pro Pro Ala Asp Asp Cys Ser Gly Arg Gly Tyr Phe Ser
                85                  90                  95

Ser Ser Glu Val Glu Tyr Ser Leu Arg Arg Leu Arg Pro Ile Arg Thr
            100                 105                 110

Ser Gly Gly Val Gly Ala Ala Ser Val Ala Pro Ala Glu Lys Gln His
            115                 120                 125

Gln Gln Gln Pro Pro Ala Thr Asp Lys Ala Lys Gly Ala Arg Lys Pro
130                 135                 140

Ala Ala Ala Ser Ala Arg Gly Gly Cys Arg Arg Pro Ala Ser Pro Gly
145                 150                 155                 160

Ala Arg Leu Ala Ser Leu Ile Asn Ala Ile Phe Ser Gly Lys Arg His
                165                 170                 175

Ser Ala Arg Gln His Pro Ala Pro Ala Asp Glu Glu Pro Ala Cys Ser
            180                 185                 190

Thr Ala Pro Ser Thr Ala Arg Pro Cys Leu Asn Lys Thr Pro Pro Ser
            195                 200                 205

Ala Arg Ala Ala Arg Ala Arg Ala Ser Arg Ser Arg Ile Arg Thr Val
210                 215                 220

Arg Phe Leu Asp Ile Asp Gly Glu Val Ala Val Ala Ala Ala Ala Ser
225                 230                 235                 240

Gly Cys Arg Arg Val Pro Val Val Glu Val Glu Asp Ser Asp Gly Gly
                245                 250                 255

Glu Glu Ser Ser Asp Ala Ser Ser Asp Leu Phe Glu Leu Asp Asn Leu
            260                 265                 270

Ala Ala Ile Ala Pro Ala Thr Gly Gly His Cys Arg Arg Ala Cys
            275                 280                 285

Ala Asp Glu Leu Pro Val Tyr Gly Thr Thr Gly Ala Gly Leu Arg His
            290                 295                 300

Asp Ile Gly Arg Arg Leu Pro Phe Gly Tyr Ser Ser His Gly Arg Ser
305                 310                 315                 320

Cys Ser Arg Val Ile
                325

<210> SEQ ID NO 27
<211> LENGTH: 400
<212> TYPE: PRT
<213> ORGANISM: Vitis vinifera

<400> SEQUENCE: 27

Met Gly Ala Asn Leu Ala Gly Val Glu Val Gly Phe Val Val His Ala
1               5                   10                  15

Leu Glu Gly Asp Ile Arg Ala Ser Ala Gly Glu Arg His Arg Ala Leu
            20                  25                  30

Phe Ser Leu Leu Ser Pro Gln Ala Trp Leu Leu Ala Phe Ile Ser Leu
        35                  40                  45

Leu Arg Ala Ile Lys His Pro Ser Met Ala Val Ser Ala Leu Phe Pro
    50                  55                  60

Phe Ser Phe Ala Phe Thr Gln Gly Ser Ser Ile Ile Arg Asn Ala Ala
65                  70                  75                  80

Phe Gln Leu Ser Arg Val Phe Ser Arg Phe Leu Ala Trp Ala Leu Gly
                85                  90                  95

Phe Phe Tyr Lys Glu Met Gln Arg Trp Asp Lys Ser Leu Arg Glu Asp
            100                 105                 110

Arg Tyr Arg Asn Gly Arg Glu Asn Pro Ser Phe Ser Thr Leu Leu
        115                 120                 125

Asp Ala Ile Tyr Arg Ser Ile Asp Glu Gly Gly Glu Gly Glu Glu
    130                 135                 140

Leu Val Leu Tyr Arg Glu Thr Met Arg Lys Lys His Thr Ile Met Ile
145                 150                 155                 160

Glu Lys Trp Met Glu Lys Lys Val Ser Glu Lys Val Val Arg Arg
                165                 170                 175

Lys Ser Met Ala Asp Phe Glu Arg Arg Ser Arg Asn Asp Arg Asp Ser
            180                 185                 190

Phe Phe Leu Asn Ser Thr Ser Ser Ser Asp Ser Ser Ser Gly Gly
        195                 200                 205

Gly Phe Ser Ser Ser Glu Ala Glu Ser Val Arg Asn Tyr Ile Ala Ser
    210                 215                 220

Gln Lys Pro Lys His Glu Gly Gly Phe Val Lys Thr Lys Ser Arg Ala
225                 230                 235                 240

Leu Lys Ile Tyr Gly Asp Leu Lys Lys Val Lys Gln Pro Ile Ser Pro
                245                 250                 255

Gly Gly Arg Leu Ala Ser Phe Leu Asn Ser Leu Phe Thr Thr Gly Thr
            260                 265                 270

Ala Lys Lys Ala Lys Ile Ser Ser Ser Glu Asp Ser Thr Pro Glu Arg
        275                 280                 285

Lys Ser Lys Ser Gly His Thr Thr Cys Ser Ser Ala Ser Ser Phe
    290                 295                 300

Ser Arg Ser Cys Leu Ser Lys Thr Pro Ser Ser Arg Ser Lys Leu Ser
305                 310                 315                 320

Asn Gly Thr Lys Arg Ser Val Arg Phe Tyr Pro Val Ser Val Ile Lys
                325                 330                 335

Asn Glu Ser Tyr Leu Arg Glu Ala Ala Asn His Glu Asp Ser Asp Asp
            340                 345                 350

Asp Ala Ala Ser Cys Ala Ser Ser Asp Leu Phe Glu Leu Asp Asn Leu

```
              355                 360                 365
Ser Ala Ile Gly Ile Asp Arg Tyr Arg Glu Glu Leu Pro Val Tyr Glu
            370                 375                 380

Thr Thr Arg Met Asp Thr Asn Arg Ala Ile Ala Ser Gly Leu Ile Leu
385                 390                 395                 400
```

<210> SEQ ID NO 28
<211> LENGTH: 52
<212> TYPE: DNA
<213> ORGANISM: Artificial Sequence
<220> FEATURE:
<223> OTHER INFORMATION: Primer
<220> FEATURE:
<221> NAME/KEY: N_region
<222> LOCATION: (42)..(47)
<220> FEATURE:
<221> NAME/KEY: misc_feature
<222> LOCATION: (42)..(47)
<223> OTHER INFORMATION: n is a, c, g, or t

<400> SEQUENCE: 28
cacgacacgc tactcaacac accacctcgc acagcgtcct annnnnngca tg          52

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
cacgacacgc tactcaacac                                              20

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
actcaacaca ccacctcgca cagc                                         24

<210> SEQ ID NO 31
<211> LENGTH: 29
<212> TYPE: DNA
<213> ORGANISM: Artificial Sequence
<220> FEATURE:
<223> OTHER INFORMATION: Primer

<400> SEQUENCE: 31
acaatgctga gggattcaaa ttctaccca                                    29

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
tactgaatta acgccgaatt gaattc                                       26

<210> SEQ ID NO 33
<211> LENGTH: 23
<212> TYPE: DNA

```
<213> ORGANISM: Artificial Sequence
<220> FEATURE:
<223> OTHER INFORMATION: Primer

<400> SEQUENCE: 33
cgactggagc acgaggacac tga                                          23

<210> SEQ ID NO 34
<211> LENGTH: 24
<212> TYPE: RNA
<213> ORGANISM: Artificial Sequence
<220> FEATURE:
<223> OTHER INFORMATION: Primer

<400> SEQUENCE: 34
cgacuggagc acgaggacac ugac                                         24

<210> SEQ ID NO 35
<211> LENGTH: 20
<212> TYPE: RNA
<213> ORGANISM: Artificial Sequence
<220> FEATURE:
<223> OTHER INFORMATION: Primer

<400> SEQUENCE: 35
auggacugaa ggaguagaaa                                              20

<210> SEQ ID NO 36
<211> LENGTH: 26
<212> TYPE: DNA
<213> ORGANISM: Artificial Sequence
<220> FEATURE:
<223> OTHER INFORMATION: Primer

<400> SEQUENCE: 36
cttggccgcc gcagccaccg cctcca                                       26

<210> SEQ ID NO 37
<211> LENGTH: 24
<212> TYPE: DNA
<213> ORGANISM: Artificial Sequence
<220> FEATURE:
<223> OTHER INFORMATION: Primer

<400> SEQUENCE: 37
agaacccgcc gtagctagaa cact                                         24

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gcgaagatgg agttgaggaa                                              20

<210> SEQ ID NO 39
<211> LENGTH: 19
<212> TYPE: DNA
<213> ORGANISM: Artificial Sequence
<220> FEATURE:
<223> OTHER INFORMATION: Primer

<400> SEQUENCE: 39
gatggagagc gacgaggac                                               19
```

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
gcaatggcgg cgaagttc                                                    18

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
accacttcga ccgccactac t                                                21

<210> SEQ ID NO 42
<211> LENGTH: 19
<212> TYPE: DNA
<213> ORGANISM: Artificial Sequence
<220> FEATURE:
<223> OTHER INFORMATION: Primer

<400> SEQUENCE: 42
acgcctaagc ctgctggtt                                                   19

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
tggcatctct cagcacattc c                                                21

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
tgcacaatgg atgggtcaga                                                  20

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
ggtttggacc ttctctctaa aatgc                                            25

<210> SEQ ID NO 46
<211> LENGTH: 24
<212> TYPE: DNA
<213> ORGANISM: Artificial Sequence
<220> FEATURE:

```
<223> OTHER INFORMATION: Primer

<400> SEQUENCE: 46
agagcctgtc tagctgtgat cctt                                          24

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
tgttggtggc tgccgatat                                                19

<210> SEQ ID NO 48
<211> LENGTH: 17
<212> TYPE: DNA
<213> ORGANISM: Artificial Sequence
<220> FEATURE:
<223> OTHER INFORMATION: Primer

<400> SEQUENCE: 48
cgccaggtgc acccttt                                                  17

<210> SEQ ID NO 49
<211> LENGTH: 18
<212> TYPE: DNA
<213> ORGANISM: Artificial Sequence
<220> FEATURE:
<223> OTHER INFORMATION: Primer

<400> SEQUENCE: 49
gcaaggcacc tgcagctt                                                 18

<210> SEQ ID NO 50
<211> LENGTH: 22
<212> TYPE: DNA
<213> ORGANISM: Artificial Sequence
<220> FEATURE:
<223> OTHER INFORMATION: Primer

<400> SEQUENCE: 50
aggcagcctt tgtacagatc ct                                            22

<210> SEQ ID NO 51
<211> LENGTH: 18
<212> TYPE: DNA
<213> ORGANISM: Artificial Sequence
<220> FEATURE:
<223> OTHER INFORMATION: Primer

<400> SEQUENCE: 51
ccgtcgctcg cattcgta                                                 18

<210> SEQ ID NO 52
<211> LENGTH: 18
<212> TYPE: DNA
<213> ORGANISM: Artificial Sequence
<220> FEATURE:
<223> OTHER INFORMATION: Primer

<400> SEQUENCE: 52
tcatgtgcct ggtggtga                                                 18
```

```
<210> SEQ ID NO 53
<211> LENGTH: 19
<212> TYPE: DNA
<213> ORGANISM: Artificial Sequence
<220> FEATURE:
<223> OTHER INFORMATION: Primer

<400> SEQUENCE: 53
gcttctttca gagggtcat                                                  19

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
gcatttcaag tacacgaggt                                                 20

<210> SEQ ID NO 55
<211> LENGTH: 21
<212> TYPE: DNA
<213> ORGANISM: Artificial Sequence
<220> FEATURE:
<223> OTHER INFORMATION: Primer

<400> SEQUENCE: 55
aaggctgtgg cttgattgac a                                               21

<210> SEQ ID NO 56
<211> LENGTH: 23
<212> TYPE: DNA
<213> ORGANISM: Artificial Sequence
<220> FEATURE:
<223> OTHER INFORMATION: Primer

<400> SEQUENCE: 56
ttaggcccaa ttttgctatt ttg                                             23

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
tgaccaacta caacgtggtc cc                                              22

<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
gccagtgtat gttttgccga ag                                              22

<210> SEQ ID NO 59
<211> LENGTH: 22
<212> TYPE: DNA
<213> ORGANISM: Artificial Sequence
<220> FEATURE:
<223> OTHER INFORMATION: Primer
```

<400> SEQUENCE: 59
ctttgagtgg ttggagtggt gg					22

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
gcagccttct tggagatgga a					21

<210> SEQ ID NO 61
<211> LENGTH: 21
<212> TYPE: DNA
<213> ORGANISM: Artificial Sequence
<220> FEATURE:
<223> OTHER INFORMATION: Primer

<400> SEQUENCE: 61
gtcggtctgt gttgcgattt g					21

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
cctccatttc ccacacagct t					21

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
acggtgatca tcacggacat					20

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
tcgaagtggt acagcgacac t					21

<210> SEQ ID NO 65
<211> LENGTH: 30
<212> TYPE: DNA
<213> ORGANISM: Artificial Sequence
<220> FEATURE:
<223> OTHER INFORMATION: Primer

<400> SEQUENCE: 65
tctagaatgg agaggtgggc ggcgcccaag					30

<210> SEQ ID NO 66
<211> LENGTH: 28

```
<212> TYPE: DNA
<213> ORGANISM: Artificial Sequence
<220> FEATURE:
<223> OTHER INFORMATION: Primer

<400> SEQUENCE: 66
ctgcagtcag acaactctgg cgctccgt                                    28

<210> SEQ ID NO 67
<211> LENGTH: 26
<212> TYPE: DNA
<213> ORGANISM: Artificial Sequence
<220> FEATURE:
<223> OTHER INFORMATION: Primer

<400> SEQUENCE: 67
ctcgagcagc cgtctttctc atccac                                      26

<210> SEQ ID NO 68
<211> LENGTH: 26
<212> TYPE: DNA
<213> ORGANISM: Artificial Sequence
<220> FEATURE:
<223> OTHER INFORMATION: Primer

<400> SEQUENCE: 68
ggatccgcga agatggagtt gaggaa                                      26

<210> SEQ ID NO 69
<211> LENGTH: 26
<212> TYPE: DNA
<213> ORGANISM: Artificial Sequence
<220> FEATURE:
<223> OTHER INFORMATION: Primer

<400> SEQUENCE: 69
ggatccgctt gtcattgctg tacatg                                      26

<210> SEQ ID NO 70
<211> LENGTH: 26
<212> TYPE: DNA
<213> ORGANISM: Artificial Sequence
<220> FEATURE:
<223> OTHER INFORMATION: Primer

<400> SEQUENCE: 70
gaattcagga aacaaacgcc aagaag                                      26

<210> SEQ ID NO 71
<211> LENGTH: 30
<212> TYPE: DNA
<213> ORGANISM: Artificial Sequence
<220> FEATURE:
<223> OTHER INFORMATION: Primer

<400> SEQUENCE: 71
tctagaatgg agaggtgggc ggcgcccaag                                  30

<210> SEQ ID NO 72
<211> LENGTH: 29
<212> TYPE: DNA
<213> ORGANISM: Artificial Sequence
<220> FEATURE:
<223> OTHER INFORMATION: Primer

<400> SEQUENCE: 72
```

```
actagtgaca actctggcgc tccgtccat                                    29

<210> SEQ ID NO 73
<211> LENGTH: 30
<212> TYPE: DNA
<213> ORGANISM: Artificial Sequence
<220> FEATURE:
<223> OTHER INFORMATION: Primer

<400> SEQUENCE: 73
gaattcgctt gtcattgctg tacatgctgt                                   30

<210> SEQ ID NO 74
<211> LENGTH: 30
<212> TYPE: DNA
<213> ORGANISM: Artificial Sequence
<220> FEATURE:
<223> OTHER INFORMATION: Primer

<400> SEQUENCE: 74
ggatcccaca cacatgttcc cattaggttt                                   30

<210> SEQ ID NO 75
<211> LENGTH: 440
<212> TYPE: DNA
<213> ORGANISM: Artificial Sequence
<220> FEATURE:
<223> OTHER INFORMATION: RNAi

<400> SEQUENCE: 75
cagccgtctt tctcatccac gctgctcgac gcgatataca agtcgatgga cgagcagccg    60
ggtcacggcg gcggcgccac cggggtggag gcggtggctg cggcggccaa gaagcagcac   120
gaggcggccc tgcactatgg gaactactac aagccgtcgc tcgcggggag ctaccgggcg   180
cgcgcgccgg gtccgcacgc cacgacgtcg agctcgtcgg agtgttctag ctacggcggg   240
ttctcgtcgt ccgaggcgga gtcgtcgcac caccgacgcc tccgccccat ccgcacgact   300
gtccccggtg gtgcgccggg gcccgcgccg gagaagaagg ccaagaagcc cggggcctcc   360
atacgcgcca agctcaggga cctccgcaag ccggcttccc ccggcgcgcg cctcgcgggc   420
ttcctcaact ccatcttcgc                                              440
```